US008178298B2

(12) United States Patent
Scott et al.

(10) Patent No.: US 8,178,298 B2
(45) Date of Patent: *May 15, 2012

(54) PATCHED POLYPEPTIDES AND USES RELATED THERETO

(75) Inventors: Matthew P. Scott, Stanford, CA (US); Lisa V. Goodrich, Menlo Park, CA (US); Ronald L. Johnson, Derwood, MD (US); Ervin Epstein, Jr., Orinda, CA (US)

(73) Assignees: The Regents of the University of California, Oakland, CA (US); The Board of Trustees of the Leland Stanford Junior University, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/685,274

(22) Filed: Jan. 11, 2010

(65) Prior Publication Data

US 2010/0221724 A1 Sep. 2, 2010

Related U.S. Application Data

(63) Continuation of application No. 11/894,801, filed on Aug. 20, 2007, now Pat. No. 7,659,371, which is a continuation of application No. 10/421,446, filed on Apr. 22, 2003, now Pat. No. 7,465,552, which is a continuation of application No. 09/724,631, filed on Nov. 28, 2000, now Pat. No. 6,551,782, which is a continuation of application No. 08/918,658, filed on Aug. 22, 1997, now Pat. No. 6,429,354, which is a continuation-in-part of application No. 08/656,055, filed on May 31, 1996, now Pat. No. 6,027,882, which is a continuation-in-part of application No. 08/540,406, filed on Oct. 6, 1995, now Pat. No. 5,837,538, which is a continuation-in-part of application No. 08/319,745, filed on Oct. 7, 1994, now abandoned.

(51) Int. Cl.
*C12Q 1/68* (2006.01)
*C12P 19/34* (2006.01)

(52) U.S. Cl. .................. 435/6.1; 435/6.11; 435/6.12

(58) Field of Classification Search .................. None
See application file for complete search history.

(56) References Cited

U.S. PATENT DOCUMENTS

| | | | |
|---|---|---|---|
| 5,023,180 A | 6/1991 | Appelbaum et al. | |
| 5,789,543 A | 8/1998 | Ingham et al. | |
| 5,798,209 A | 8/1998 | Chan | |
| 5,837,538 A | 11/1998 | Scott et al. | |
| 5,844,079 A | 12/1998 | Ingham et al. | |
| 5,935,810 A | 8/1999 | Friedman et al. | |
| 6,027,882 A * | 2/2000 | Scott et al. | 435/6 |
| 6,165,747 A | 12/2000 | Ingham et al. | |
| 6,172,200 B1 | 1/2001 | Scott et al. | |
| 6,261,786 B1 | 7/2001 | Marigo et al. | |
| 6,271,363 B1 | 8/2001 | Ingham et al. | |
| 6,384,192 B1 | 5/2002 | Ingham et al. | |
| 6,429,354 B1 | 8/2002 | Scott et al. | |
| 6,551,782 B1 * | 4/2003 | Scott et al. | 435/6 |
| 6,576,237 B1 | 6/2003 | Ingham et al. | |
| 6,607,913 B1 | 8/2003 | Ingham et al. | |
| 6,610,507 B2 | 8/2003 | Scott et al. | |
| 6,610,656 B1 | 8/2003 | Ingham et al. | |
| 6,630,148 B1 | 10/2003 | Ingham et al. | |
| 6,664,075 B2 | 12/2003 | Ingham et al. | |
| 6,884,775 B1 | 4/2005 | Tabin et al. | |
| 6,921,646 B2 | 7/2005 | Scott et al. | |
| 6,946,257 B1 | 9/2005 | Scott et al. | |
| 7,060,450 B1 | 6/2006 | Tabin et al. | |
| 7,144,732 B2 | 12/2006 | Ingham et al. | |

FOREIGN PATENT DOCUMENTS

WO  WO 96/11260  4/1996

OTHER PUBLICATIONS

Schuske et al., "patched Overexpression Causes Loss of wingless Expression in *Drosophila* Embryos," Developmental Biology, Jul. 1994, vol. 163, pp. 300-311.*
Namba et al., "Lack of PTC geen (ret proto-oncogene rearrangement) in Human thyroid tumors," Endocrinol. Jpn., Dec. 1991, vol. 38, No. 6, pp. 627-632, Abstract Only.*
Akimaru, H. et al., "*Drosophila* CBP is a co-activator of cubitus interruptus in hedgehog signaling", Nature 386 (6626): 735-738 (1997).
Akiyama, H. et al., "Cloning of a mouse smoothened cDNA and expression patterns of hedgehog signaling molecules during chondrogenesis and cartilage differentiation in conal mouse EC cells, ATDC5", Biophys Res. Comm., 235(1): 142-147 (1997).
Alberts, eds., Molecular Biology of the Cell, G-10 (1994).
Alcedo, J. and Noll, M., "Hedgehog and its patched-smoothened receptor complex: a novel signaling mechanism at the cell surface", Biol. Chem., 378 (7): 583-590 (1997).
Alcedo, J. et al., "The *Drosophila* smoothened gene encodes a seven-pass membrane protein, a putative receptor for the hedgehog signal", Cell, 86 (2): 221-232 (1996).
Alexandre, C. et al., "Transcriptional activation of hedgehog target genes in *Drosophila* is mediated directly by the cutitus interrptus protein, a member of the GLI family of zinc finger DNA-binding proteins", Genes Dev., 19 (16): 2003-2013 (1996).
Altaba et al (Cell 90:193-196, 1997).

(Continued)

*Primary Examiner* — Young J Kim
(74) *Attorney, Agent, or Firm* — Ropes & Gray LLP

(57) ABSTRACT

Methods for isolating patched genes, including the mouse and human patched genes, as well as invertebrate patched genes and sequences, are provided. Decreased expression of patched is associated with the occurrence of human cancers, particularly basal cell carcinomas of the skin. The patched and hedgehog genes are useful in creating transgenic animal models for these human cancers. The patched nucleic acid compositions find use in identifying homologous or related proteins and the DNA sequences encoding such proteins; in producing compositions that modulate the expression or function of the protein; and in studying associated physiological pathways. In addition, modulation of the gene activity in vivo is used for prophylactic and therapeutic purposes, such as treatment of cancer, identification of cell type based on expression, and the like. The DNA is further used as a diagnostic for a genetic predisposition to cancer, and to identify specific cancers having mutations in this gene.

5 Claims, 7 Drawing Sheets

OTHER PUBLICATIONS

Bale, A., "Variable expressivity of patched mutations in flies and humans", Am. J. Human Genet., 60 (1): 10-12 (1997).

Bellusci, S. et al., "Involvement of Sonic hedgehog (Shh) in mouse embryonic lung growth and morphogenesis", Development, 124 (1): 53-63 (1997).

Bhat, K. and Schedl, P., "Requirement for engrailed and invected genes reveals novel regulatory interactions between engrailed/invected, patched,, gooseberry and wingless during Drosophila neurogenesis", Development, 124 (9)L 1675-1688 (1997).

Bitgood, M. et al., "Sertoli cell signaling by Desert hedgehog regulates the male germline", Curr. Biol., 6 (3): 298-304 (1996).

Bokor, P. et al., "The roles of hedgehog, wingless and lines in patterning the dorsal epidermis in Drosophila", Development, 122 (4): 1083-1092 (1996).

Bowie et al., "Deciphering the Message in Protein Sequences: Tolerance to Amino Acid Substitutions", Science 247: 1306-1310 (1990).

Burke, R., and Basler K.,"Hedgehog signaling in Drosophila eye and limb development-conserved machinery, divergent roles?", Curr. Opin. Neurobiol., 7(1): 55-61 (1997).

Buscher, D. et al., "Evidence for Genetic Control of Sonic Hedgehog by Gli3 in Mouse Limb Development", Mech. Dev., 62 (2):175-182 (1997).

Cadigan, K. et al., "Localized expression of sloppy paired protein maintains the polarity of Drosophila parasegments", Genes Dev., 8 (8): 899-913 (1994).

Chang-Claude et al., "The patched polymorphism Pro1315Leu (C3944T) may modulate the association between use of oral contraceptives and breast cancer risk," Int. J. Cancer, vol. 103, pp. 779-783 (2003).

Chanut, F. and Heberlein, U., "Role of the morphogenetic furow in establishing polarity in the Drosophila eye", Development, 121 (12): 4085-1094 (1995).

Chavrier et al., "The complexity of the Rab and Rho GTP-binding protein subfamilies revealed by a PCR cloning approach", Gene 112: 261-264 (1992).

Chen, E. et al., "Compartmental organization of the Drosophila genital imaginal disks", Development, 124 (1): 205-218 (1997).

Chen, Y. et al., "Dual roles for patched in sequestering and transducing Hedgehog", Cell, 87(3): 553-563 (1996).

Concordet, J. et al., "Spatial regulation of a zebrafish patched homoloogue reflects the roles of sonic hedgehog and protein kinase A in neural tube and somite patterning", Development, 122 (9): 2835-2846 (1996).

Dhawan et al., "Systematic Delivery of Human Growth Hormone by Injection of Genetically Engineered Myoblasts", Science 254: 1509-1512 (1991).

Dominguez, M. et al., "Sending and receiving the hedgehog signal: control by the Drosophila Gli protein cubitus interruptus", Science, 272 (5268): 1621-1625 (1996).

Echelard, Y. et al., "Sonic hedgehog, a member of a family of putative signaling molecules, is implicated in the regulation of CNS polarity", Cell, 75: 1417-1430 (1993).

Epps, J. et al., "Oroshigane, a new segment polarity gene of Drosophila melanogaster, functions in hedgehog signal transduction", Genetics 145 (4): 1041-1052 (1997).

Epstein, D. et al., "Antagonizing cAMP-dependent protein kinase A in the dorsal CNS activates a conserved Sonic hedgehog signaling pathway", Development, 122 (9): 2884-2894 (1996).

Fan et al (Cell 81(3): 457-465, May 5, 1995).

Forbes et al., "Genetic Analysis of Hedgehod signalling in the Drosophilia Embryo", Development(Supplement), pp. 115-124 (1993).

Forbes, A. et al., "The role of segment polarity genes during early oogenesis in Drosophila", Development, 122 (10): 33283-3294 (1996).

Gailani et al., "Developmental Genes and Cancer: Role of Patched in Basal Cell Carcinoma of the Skin", J. Nat. Canc. Inst. 89 (15): 1103-1109 (1997).

Gailani, M. et al., "The role of the human homologue of Drosophila patched in spradic basal cell carcinomas", Nat. Genet., 14 (1): 78-81 (1996).

Gomez-Skarmeta, J.L. et al. "Araucan and caupolican.provide a link between compartment subdivisions and patterning of sensory organs and veins in the Drosophila wing", Genes Dev., 10 (22): 2935-1945 (1996).

Goodrich, L. et al., "Altered neural cell fates and medulloblastoma in mouse patched mutants", Science, 277 (5329): 1109-1113 (1997).

Goodrich, L. et al., "Conservation of the hedgehog/patched signaling pathway from flies to mice: induction of a mouse patched gene by Hedgehog", Genes Dev., 10 (3): 301-312 (1996).

Gorlin, R., "Nevoid basal-cell carcinoma syndrome", Medicine, 66: 98-113 (1987).

Grindley, J. et al., "Evidence for the involvement of the Gli gene family in embryonic mouse lung development", Dev. Biol., 188 (2): 337-348 (1997).

Habuchi, et al., "Detailed deletion mapping of chromosome 9q bladder cancer: evidence or two tumour suppressor loci", Oncogene, 11:1671-1674 (1995).

Hahn, H. et al., "A mammalian patched homolog is expressed in target issues of sonic hedgehog and maps to a region associated with development abnormalities", J. Biol. Chem., 271 (21): 12125-12128 (1996).

Hammerschmidt, M. et al., Genes & Development, 10: pp. 647-658.

Heemskerk, J. et al., "Drosophila hedgehog acts as a morphogen in cellular patterning", Cell 76: 449-460 (1994).

Hepker, J. et al., "Drosophila cubitus interruptus forms a negative feedback loop with patched and regulates expression of Hedgehog target genes", Development, 124 (2): 549-558 (1997).

Hidalgo Alicia, "Interaction between segment polarity genes and the generation of the segmental pattern in Drosophila", Mechanisms of Development 35 :77-87 (1991).

Hidalgo Alicia, "Three distinct roles for the engrailed gene in Drosophila wing development", Current Biology 4(12) : 1087-1098 (1994).

Hidalgo, A. and Ingham, P., "Cell patterning in the Drosophila segment: spatial regulation of the segment polarity gene patched", Development, 110: 291-301 (1990).

Hooper et al., "The Drosophila patched gene encodes a putative membrane protein required for segmental patterning", Cell 59: 751-765 (1989).

Hynes, M., et al., "Control of cell pattern in the neural tube by zinc finger transcription factor and oncogene," Neuron, vol. 19(1), pp. 15-26 (1997).

Ingham, "Hedgehog points the way", Curr. Biol. 4: 347-350 (1994).

Ingham, P. et al., "Quantitative effects of hedgehog and decapentaplegic activity on the patterning of the Drosophila wing", Curr. Biol., 5 (4): 432-440 (1995).

Ingham, P. et al., "Role of the Drosophila patched gene in positional signalling", Nature, 353: 184-187 (1991).

Jensen, A. et al., "Expression of Sonic hedgehog and its putative role as a precursor cell mitogen in the developing mouse retina", Development, 124 (2): 363-371 (1997).

Jiang, J. et al., "Protein kinase A and hedgehog signaling in Drosophila limb development", Cell, 80 (4): 563-572 (1995).

Johnson, R. et al., "Human homolog of patched, a candidate gene for the basal cell nevus syndrome", Science, 272 (5268): 1668-1671 (1996).

Johnson, R. et al., "Patched overexpression alters wing disc size and pattern: transcriptional and post-transcriptional effects on hedgehog targets", Development, 121 (12): 4161-4170 (1995).

Kalderon, D., "Morphogenetic signalling. Responses to hedgehog", Curr. Biol., 5 (6): 2279-2289 (1995).

Kato (Nippon Yakurigaku Zasshi. Folia Pharmacoligica Japonica (102(3): AN 94010590, pp. 245-252 (1993).

Kojima, T. et al., "Induction of a mirror-image duplication of anterior wing structures by localized hedgehog expression in the anterior compartment of Drosophila melanogaster wing imaginal discs", Gene, 148 (2): 211-7 (1994).

Krauss, S. et al., "A functionally conserved homolog of the Drosophila segment polarity gene hh is expressed in tissues with polarizing activity in zebrafish embryos", Cell, 75: 1431-1444 (1993).

Krishnan et al (Science 278: 1947-1950, (Dec. 12, 1997).

Lepage et al., "Signal transduction by cAMP-dependent protein kinase A in *Drosophila* limb patterning", Nature, 373 (6516): 711-715 (1995).
Levanat et al., "Role of hedgehog/patched signaling patheay in oncogenesis," Ann. N.Y. Acad. Science, vol. 1030, p. 134-143 (2004).
Li, W., et al., "Function of protein kinase A in hedgehog signal transduction and *Drosophila* imaginal disc development", Cell, 80 (4): 553-562 (1995).
Loftus, S., et al., "Murine model of Niemann-Pick C disease: mutation in a cholesterol homeostatis gene", Science, 277 (5323): 232-235 (1997).
Ma et al., "Molecular Cloning and Characterization of rKlk10, a cDNA encoding T-Kininogenase from Rat Submandibular Gland and Kidney", Biochemistry 31: 10922-10928, (1992).
Ma, C. et al., "The segment polarity gene hedgehog is required for progression of the morphogenic furrow in the developing *Drosophila* eye", Cell, 75 (5): 927-938 (1993).
Ma, C. et al., "Wingless and patched are negative regulators of the morphogenetic furrow and can effect tissue polarity in the developing *Drosophila* compound eye", Development, 121 (8): 2279-2289 (1995).
Macias, A., et al., "Genetic Factors controlling the expression of the abdominal-A gene of *Drosophila* within its domain", Mechanisms of Development, 45(1), pp. 15-25 (1994).
Marigo, V. et al., "Biochemical evidence that patched is the Hedgehog receptor", Nature, 384 (6605): 176-179 (1996).
Marigo, V. et al., "Conservation in hedgehog signaling: induction of a chicken patched homolog by Sonic hedgehog in the developing limb", Development, 122 (4): 1225-1233 (1996).
Marigo, V. et al., "Regulation of patched by sonic hedgehog in the developing neural tube", Proc. Natl. Acad. Sci. USA, 93(18): 9346-9351 (1996).
Marigo, V. et al., "Sonic hedgehog differentially regulates expression of GLI and GLI3 during limb development", Dev. Biol., 180 (1): 273-283 (1996).
Muller et al (Development 127: 2999-3007, 2000).
Nakamura, T. et al., "Induction of osteogenic differentiation by hedgehog proteins", Biochem. Biophys. Res. Comm., 237 (2): 465-469 (1997).
Nakano, Y. et al., "A protein with several possible membrane-spanning domains encoded by the *Drosophila* segment polarity gene patched", Nature, 341: 508-513 (1989).
Ngo et al., "Computational Complexity, Protein Structure Prediction, and the Levinthal Paradox", Peptide Hormones, 491-494 (1996).
Noveen, A. et al., Biochemical and Biophysical Research Communications, 219, pp. 180-185 (1996) Article No. 0202.
Nusse, R. "Patching up Hedgehog", Nature, 384 (6605): 119-120 (1996).
Oro, A. et al., "Basal cell carcinomas in mice overexressing sonic hedgehog", Science, 276(5313)L 817-821 (1997).
Pennisi, "Gene Linked to Commonest Cancer", Science 272: 1583-1584 (1996).
Perrimon et al., "Generating lineage-specific markers to study *Drosophila* development", Dev. Genet. 12:238-252 (1991).
Perrimon, N., "Serpentine proteins lither into the wingless and hedgehog fields", Cell, 86 (4): 513-516 (1996).
Phillips, R. et al., "The *Drosophila* segment polarity gene patched is involved in a position signalling mechanism in imaginal discs", Development, 110: 105-114 (1990).
Platt A. K. et al., "Expression of the mouse Gli and Ptc genes is adjacent to embryonic sources of hedgehog signals suggesting a conservation of pathways between flies and mice", Mechanisms of Development 62:121-135 (1997).
Quinn, A. et al., "Chromosome 9 allele loss occurs in both basal and squamous cell carcinomas of the skin", J. Inves. Dermatology, 102: 300-303 (1994).
Quinn, A. et al., "Delineation of two distinct deleted regions on chromosome 9 in human non-melanoma skin cancers", Genes, Chromosomes & Cancers, 11:222-225 (1994).
Riddle, R. et al., "Sonic hedgehog mediates the polarizing activity of the ZPA", Cell, 75: 1401-1416 (1993).

Roelink, H. et al., "Floor plate and motor neuron induction by *vhh*-1, a vertebrate homolog of hedgehot expressed by the notochord", Cell, 76: 761-775 (1994).
Rogers, G. et al., "Patched gene mutation screening in patients with basal cell nevus syndrome using biodirectional dideoxy fingerprinting", J. Invest. Dermatol. Abstracts, 108(4): 598, # 364, (1997).
Roush, W., "Hedgehog's patterning call is patched through, smoothly", Science, 274 (5291): 1304-1305 (1996).
Rudinger, "Characteristics of the amino acids as components of a peptide hormone sequence", Endocrinology 5-7 (1972).
Sampedro J. and Guerrero I., "Unrestricted expression of the *Drosophila* gene patched allows a normal segment polarity", Nature 353: 187-190 (Sep. 12, 1991).
Sanchez- Herrero et al., "The fu gene discriminaes between pathways to control dpp expression in *Drosophila* imaginal discs", Mechanisms of Development 55: 159-170 (1996).
Sanicola, M. et al., "Drawing a stripe in *Drosophila* imaginal disks: negative regulation of decapentaplagic and patched expression by engrailed", Genetics, 139 (2): 745-756 (1995).
Schuske, K. et al., "Patched Overexpression Causes Loss of Wingless Expression in *Drosophila* Embryos," Developmental Biology, 164(1), pp. 300-311 (1994).
Scott P. Matthew, "Hox genes Arms and the Man", Nature Genetics 15: 117-118 ( Feb. 1997).
Shilo, B., "Tumor suppressors. Dispatches from patched", Nature, 382 (6587): 115-116 (1996).
Simcox, A. et al., "Imaginal discs can be recovered from culture embryos mutant for the segment-polarity genes engrailed, naked and patched but nor from wingless", Development, 107: 715-722 (1989).
Sisson, J. et al., "Costal2, a novel kinesin-related protein in the Hedgehog signaling pathway", Cell, 90 (2): 235-245 (1997).
Smith et al., "Genes Transferred by Retroviral Vectors into Normal and Mutant Myoblasts in Primary Cultures are Expressed in Myotubes", Mol. Cell. Biol. 3268-3271 (1990).
Spradling et al., "Transposition of Cloned P Elements into *Drosophila* Germ Line Chromosomes", Science 218: 341-347 (1982).
Stone, D. et al., "The tumor-suppressor gene patched encodes a candidate receptor for Sonic hedgehog", Nature, 384 (6605): 129-134 (1996).
Struhl, G. et al., "Hedgehog acts by distinct gradient and signal relay mechanisms to organize cell type d cell polarity in the *Drosophila* abdomen", Development, 124 (11): 2155-2165 (1997).
Strutt I. David and Mlodzik Marek, "The regulation of hedgehog and decapentaplegic during *Drosophila* eye imaginal disc development", Mechanisms of Development 58: 39-50 (1996).
Strutt, D. et al., "Ommatidial polarity in the *Drosophila* eye is determined by the direction of furrow progression and local interactions", Development, 121 (12): 4247-4256 (1995).
Strutt, D. et al., "Regulation of furrow progression in the *Drosophila* eye by cAMP-dependent protein kinase A", Nature, 373 (6516): 705-709 (1995).
Tabata, T. et al., "Hedgehog is a signaling protein with a key role in patterning *Drosophila* imaginal discs", Cell, 76: 89-102 (1994).
Tabata, T. et al., "The *Drosophila* hedgehog gene is expressed specifically in posterior compartment cells and is a target of engrailed regulation", Genes Dev., 6(12B): 2635-2645 (1992).
Takabatake, T. et al., "Hedgehog and patched gene expression in adult ocular tissues", FEBS Letters, 410 (2-3): 485-489 (1997).
Taylor et al., "Contrasting distribution of patched and hedgehog proteins in the *Drosophila* embryo", Mechanisms of Development 42:89-96 (1993).
Thummel, C. et al., "Vectors for Drosopl ila P-element mediated transformation and tissue culture transfection", Gene, 74: 445-446 (1988).
Von Ohlen, T. et al. "Hedgehog signaling regulates transcription through cubitus interruptus, a sequence-specific DNA binding protein", Proc. Natl. Acad. Sci. USA, 94 (6): 2404-2409 (1997).

Vorechovsky, I. et al, "Somatic mutations in the human homologue of *Drosophila* patched in primitive neuroectodermal tumors", Oncogene, 15 (3): 361-366 (1997).

Vortkamp, A., et al., "Regulation of rate of cartilage differentiation by Indian hedgehog and PTH-related protein", Science, 273 (5275): 613-622 (1996).

Watson, J., Recombinant DNA, W. H. Freeman and Co., New York, 363, (1992).

Weed et al., "The Role of Sonic Hedgehog in Vertebrate Development", Matrix Biology 16 : 53-58 (1997).

Wells, A. James, "Additivity of Mutational Effects in Proteins", Biochemistry, 39(37): 8509-8517 (Sep. 18, 1990).

Wicking, C. et al., "Fine genetic mapping of the gene for nevoid basal cell carcinoma syndrome", Genomics, 22: 505-511 (1994).

* cited by examiner

PATCHED POLYPEPTIDES AND USES RELATED THERETO

RELATED APPLICATIONS

This application is a continuation of and claims priority to U.S. application Ser. No. 11/894,801, filed Aug. 20, 2007, which is a continuation of U.S. application Ser. No. 10/421,446, filed on Apr. 22, 2003, now U.S. Pat. No. 7,465,552, which is a continuation of U.S. application Ser. No. 09/724,631, filed on Nov. 28, 2000, now U.S. Pat. No. 6,551,782, which is a continuation of 08/918,658, filed on Aug. 22, 1997, now U.S. Pat. No. 6,429,354, which is a continuation-in-part of U.S. application Ser. No. 08/656,055, filed on May 31, 1996, now U.S. Pat. No. 6,027,882, which is a continuation-in-part of U.S. application Ser. No. 08/540,406, filed on Oct. 6, 1995, now U.S. Pat. No. 5,837,538, which is a continuation-in-part of U.S. application Ser. No. 08/319,745, filed on Oct. 7, 1994 (now abandoned). The specifications of each of the foregoing applications are incorporated herein by reference in their entirety.

SEQUENCE LISTING

The instant application contains a Sequence Listing which has been submitted via EFS-Web and is hereby incorporated by reference in its entirety. Said ASCII copy, created on Apr. 26, 2010, is named CIBTP142.txt, and is 94,782 bytes in size.

BACKGROUND OF THE INVENTION

Segment polarity genes were originally discovered as mutations in flies that change the pattern of body segment structures. Mutations in these genes cause animals to develop changed patterns on the surfaces of body segments; the changes affecting the pattern along the head to tail axis. Among the genes in this class are hedgehog, which encodes a secreted protein (HH), and patched, which encodes a protein structurally similar to transporter proteins, having twelve transmembrane domains (ptc), with two conserved glycosylation signals.

The hedgehog gene of flies has at least three vertebrate relatives—Sonic hedgehog (Shh); Indian hedgehog (Ihh), and Desert hedgehog (Dhh). Shh is expressed in a group of cells, at the posterior of each developing limb bud, that have an important role in signaling polarity to the developing limb The Shh protein product, SHH, is a critical trigger of posterior limb development, and is also involved in polarizing the neural tube and somites along the dorsal ventral axis. Based on genetic experiments in flies, patched and hedgehog have antagonistic effects in development. The patched gene product, ptc, is widely expressed in fetal and adult tissues, and plays an important role in regulation of development. Ptc down-regulates transcription of itself, members of the transforming growth factor and Wnt gene families, and possibly other genes. Among other activities, HH upregulates expression of patched and other genes that are negatively regulated by patched.

It is of interest that many genes involved in the regulation of growth and control of cellular signaling are also involved in oncogenesis. Such genes may be oncogenes, which are typically upregulated in tumor cells, or tumor suppressor genes, which are down-regulated or absent in tumor cells. Malignancies may arise when a tumor suppressor is lost and/or an oncogene is inappropriately activated. Familial predisposition to cancer may occur when there is a mutation, such as loss of an allele encoding a suppressor gene, present in the germ-line DNA of an individual.

The most common form of cancer in the United States is basal cell carcinoma of the skin. While sporadic cases are very common, there are also familial syndromes, such as the basal cell nevus syndrome (BCNS). The familial syndrome has many features indicative of abnormal embryonic development, indicating that the mutated gene also plays an important role in development of the embryo. A loss of heterozygosity of chromosome 9q alleles in both familial and sporadic carcinomas suggests that a tumor suppressor gene is present in this region. The high incidence of skin cancer makes the identification of this putative tumor suppressor gene of great interest for diagnosis, therapy, and drug screening.

Relevant Literature

Descriptions of patched, by itself or its role with hedgehog may be found in Hooper and Scott (1989) *Cell* 59-751-765; and Nakano et al. (1989) *Nature* 341-508-513. Both of these references also describe the sequence for *Drosophila* patched. Discussions of the role of hedgehog include Riddle et al. (1993) *Cell* 75-1401-1416-, Echelard et al. (1993) *Cell* 75:1417-1430—Krauss et al. (1993) *Cell* 75:1431-1444 (1993); Tabata and Kornberg (1994) 76:89-102; Heemskerk and DiNardo (1994) *Cell* 76:449-460; and Roelink et al. (1994) *Cell* 76:-761-775.

Mapping of deleted regions on chromosome 9 in skin cancers is described in Habuchi et al. (1995) *Oncogene* 11: 1 671-1674, Quinn et al. (1994) *Genes Chromosome Cancer* 11:222-225; Quinn et al. (1994) *J. Invest. Dermatol.* 102:300-303; and Wicking et al. (1994) *Genomics* 22:505-51 1.

Gorlin (1987) *Medicine* 66:98-113 reviews nevoid basal cell carcinoma syndrome. The syndrome shows autosomal dominant inheritance with probably complete penetrance. About 60% of the cases represent new mutations. Developmental abnormalities found with this syndrome include rib and craniofacial abnormalities, polydactyly, syndactyly and spina bifida. Tumors found with the syndrome include basal cell carcinomas, fibromas of the ovaries and heart, cysts of the skin, jaws and mesentery, meningiomas and medulloblastomas.

SUMMARY OF THE INVENTION

Isolated nucleotide compositions and sequences are provided for patched (ptc) genes, including mammalian, e.g. human and mouse, and invertebrate homologs. Decreased expression of ptc is associated with the occurrence of human cancers, particularly basal cell carcinomas and other tumors of epithelial tissues such as the skin. The cancers may be familial, having as a component of risk a germline mutation in the gene, or may be sporadic. Ptc, and its antagonist hedgehog, are useful in creating transgenic animal models for these human cancers. The ptc nucleic acid compositions find use in identifying homologous or related genes; in producing compositions that modulate the expression or function of its encoded protein, ptc; for gene therapy; mapping functional regions of the protein- and in studying associated physiological pathways. In addition, modulation of the gene activity in vivo is used for prophylactic and therapeutic purposes, such as treatment of cancer, identification of cell type based on expression, and the like. Ptc, anti-ptc antibodies and ptc nucleic acid sequences are useful as diagnostics for a genetic predisposition to cancer or developmental abnormality syndromes, and to identify specific cancers having mutations in this gene.

DATABASE REFERENCES FOR NUCLEOTIDE AND AMINO ACID SEQUENCES

Figure 1:
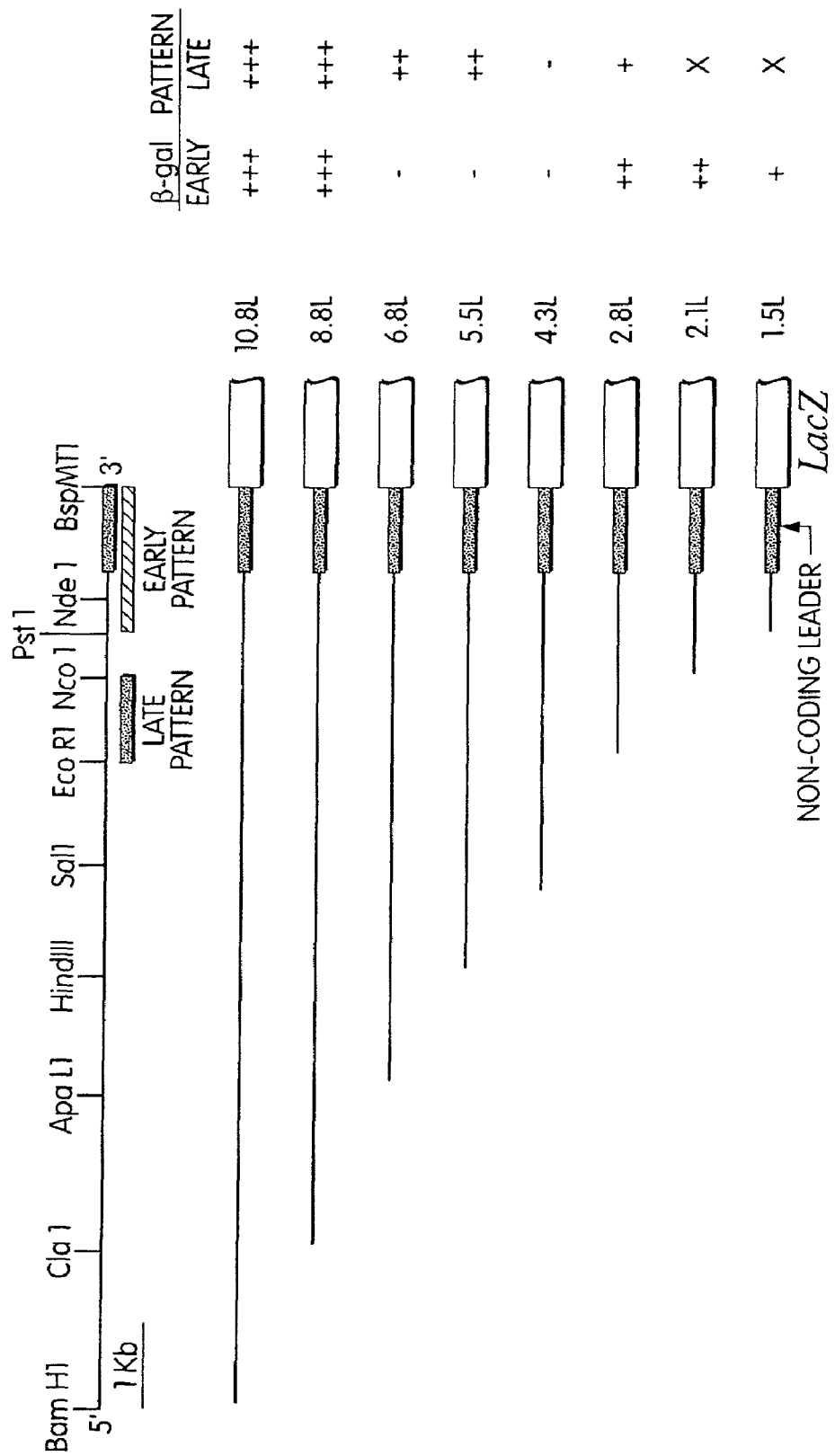
FIG. 1 is a graph having a restriction map of about 10 kbp of the 5' region upstream from the initiation codon of *Drosophila* patched gene and bar graphs of constructs of truncated portions of the 5' region joined to fl-galactosidase, where the constructs are introduced into fly cell lines for the production of embryos. The expression of fl-gal in the embryos is indicated in the right-hand table during early and late development of the embryo. The greater the number of +'s, the more intense the staining.

The sequence for the *D. melanogaster* patched gene has the Genbank accession number M28418. The sequence for the mouse patched gene has the Genbank accession number 1t30589-V46155. The sequence for the human patched gene has the Genbank accession number U59464.

DETAILED DESCRIPTION OF THE INVENTION

Vertebrate and invertebrate patched (ptc) gene compositions and methods for their isolation are provided. Of particular interest are mammalian ptc genes, such as the human and mouse homologs described in the appended examples. The ptc gene, in mammals, is a tumor suppressor and developmental regulator. Certain human cancers, e.g. basal cell carcinoma, transitional cell carcinoma of the bladder, meningiomas, medulloblastomas, etc., can be characterized by ptc loss-of-function, such as that resulting from oncogenic mutations at the ptc locus, or other loss-of-function mutations which decrease ptc activity in the cell. As described below, we have observed somatic mutations in the ptc gene in a variety of sporadic cancers. For instance, the basal cell nevus syndrome (BCNS), an inherited disorder, is associated with germline mutations in ptc. Some patients with basal cell nevus syndrome (BCNS) have germ line mutations in ptc, and are at increased risk for developmental defects such as spina bifida and craniofacial abnormalities, basal cell carcinoma (BCC) of the skin, and brain tumors. Mutations to ptc genes are also observed to occur in sporadic BCCs, which generally have both copies of ptc inactivated.

The term "loss-of-function" is art recognized and, with respect to a patched gene or gene product refers to mutations in a patched gene which ultimately decrease or otherwise inhibit the ability of a cell to transduce patched-mediated signals, e.g., the cells may lose responsiveness to hedgehog induction. For example, a loss-of-function mutation to a patched gene may be a point mutation, deletion or insertion of sequences in the coding sequence, intron sequence or 5' or 3' flanking sequences of the gene so as to, for example, (i) alter (e.g., decrease) the level patched expression, (ii) alter exon-splicing patterns, (iii) alter the ability of the encoded patched protein to interact with extracellular or intracellular proteins (such as hedgehog), or (iv) alter (decrease) the stability of the encoded patched protein.

The term "aberrant modification" is art recognized and, with respect to a patched gene, refers to a non-wildtype mutation or other alteration to the gene, e.g., which results in full or partial loss-of-function of the patched protein or expression of the patched gene.

Such mutations affecting ptc activity have also been associated with other human cancers, including carcinomas, adenocarcinomas, sarcomas and the like. Decreased ptc activity is also associated with inherited developmental abnormalities, e.g. rib and craniofacial abnormalities, polydactyly, syndactyly and spina bifida.

The art-recognized term "predisposing mutation", as it pertains to patched genes, refers to mutations to the patched gene which result in loss-of-function.

The term "genetic predisposition" is art recognized, and refers to a genotype of an animal which predisposes the animal to developing a certain pathological conditions with a frequency (probability) greater than the average for the overall population of that animal, taking into account, as appropriate, age, sex or other related physical or medical condition(s).

The ptc genes and fragments thereof, encoded protein, and anti-ptc antibodies are useful in the identification of individuals predisposed to development of a variety of cancers and developmental abnormalities, and in characterizing the phenotype of various tumors or other proliferative or degenerative disorders that are associated with this gene, e.g., for diagnostic and/or prognostic benefit. The characterization is useful for prenatal screening; and in determining the phenotype of a proliferative disorder, e.g. for determining a course of treatment of the patient. Tumors may be typed or staged as to the ptc status, e.g. by detection of mutated sequences, antibody detection of abnormal protein products, and functional assays for altered ptc activity.

The terms "developmental disorder" and "developmental abnormality" are art recognized, and refer to aberrant development of a cell, tissue or organ, e.g., in size, symmetry or functional performance, which abnormality may or may not be untowardly manifest.

The term "proliferative disorder" is art recognized and refers to a disorder affecting an animal in a manner which is marked by aberrant, or otherwise unwanted, proliferation of a subset of cells of an animal. Cancers are proliferative disorders.

The encoded ptc protein is also useful in drug screening for compositions that mimic ptc activity or expression, including altered forms of ptc protein, particularly with respect to ptc function as a tumor suppressor in oncogenesis.

The human and mouse ptc gene sequences and isolated nucleic acid compositions are provided in the appended examples. In identifying the mouse and human patched genes, cross-hybridization of DNA and amplification primers were employed to move through the evolutionary tree from the known *Drosophila* ptc sequence, identifying a number of invertebrate homologs.

The human patched gene has been mapped to human chromosome band 9q22.3, and lies between the polymorphic markers D9S196 and D9S287 (a detailed map of human genome markers may be found in Dib et al. (1996) *Nature* 280:152—http://www.genethon.fr).

As will be understood by those skilled in the art, the method of the present invention can be carried out using any of a large number of assay techniques for detecting alterations in ptc genes and/or ptc protein function. For instance, individuals are screened by analyzing their DNA or RNA for the presence of a predisposing oncogenic or developmental mutation, as compared to a normal sequence. An exemplary "normal" sequence of patched is provided in SEQ ID NO:19 (human). Specific mutations of interest include any mutation that leads to oncogenesis or developmental abnormalities, including insertions, substitutions and deletions in the coding region sequence, in the introns (e.g., that affect splicing), in the transcriptional regulatory sequences (such as promoter or enhancer sequences) that affect the activity and expression of the protein.

In general, the subject method can be characterized as including a step of detecting, in a sample of cells from a patient, the presence or absence of ptc expression (at the protein or mRNA transcript level), mutations to the ptc gene (coding or non-coding sequence) and/or the functional activity of ptc in the sample of cells (such as induction of Gli or the like). Moreover, the subject method can be used to assess the phenotype of cells which are known to be transformed, the phenotype results being useful in planning a particular therapeutic regimen.

To illustrate, nucleic acid samples are obtained from a patient having, or suspected as being at risk for developing, a tumor or developmental abnormality which may be associated with ptc. The nucleic acid is analyzed for the presence of a predisposing mutation in the ptc gene. The presence of a mutated ptc sequence that affects the level of expression of the gene, stability of the gene product, and/or signal transduction activity of ptc confers an increased susceptibility to a proliferative or developmental disorder. Thus, the level of expression of ptc can be used predictively to evaluate whether a sample of cells contains cells which are, or are predisposed towards becoming, transformed.

Diagnostic/prognostic screening of tissue/cell samples for tumors or developmental abnormalities may also be based on the functional or antigenic characteristics of the protein. Immunoassays designed to detect the normal or abnormal ptc protein may be used in screening. Where many diverse mutations lead to a particular disease phenotype, functional protein assays have proven to be effective screening tools. Such assays may be based on detecting changes in the transcriptional regulation mediated by ptc, or may directly detect ptc activities such as hedgehog binding, transporter activity or the like, or may involve antibody localization of patched in cells.

Inheritance of BCNS is autosomal dominant, although many cases are the result of new mutations. Diagnosis of BCNS is performed by protein, DNA sequence or hybridization analysis of any convenient sample from a patient, e.g. biopsy material, blood sample, scrapings from cheek, etc. A typical patient genotype will have a predisposing mutation on at least one chromosome. In tumors and at least sometimes developmentally affected tissues, loss of heterozygosity at the ptc locus leads to aberrant cell and tissue behavior. When the normal copy of ptc is lost, leaving only the reduced function mutant copy, abnormal cell growth and reduced cell layer adhesion is the result. Examples of specific ptc mutations in BCNS patients are a 9 by insertion at nt 2445 of the coding sequence- and an 11 by deletion of nt 2441 to 2452 of the coding sequence. These result in insertions or deletions in the region of the seventh transmembrane domain.

Prenatal diagnosis of BCNS may be performed, particularly where there is a family history of the disease, e.g. an affected parent or sibling. It is desirable, although not required, in such cases to determine the specific predisposing mutation present in affected family members. A sample of fetal DNA, such as an amniocentesis sample, fetal nucleated or white blood cells isolated from maternal blood, chorionic villus sample, etc. is analyzed for the presence of the predisposing mutation. Alternatively, a protein based assay, e.g. functional assay or immunoassay, is performed on fetal cells known to express ptc.

Sporadic tumors associated with loss of ptc function include a number of carcinomas and other transformed cells known to have deletions in the region of chromosome 9q22, e.g. basal cell carcinomas, transitional bladder cell carcinoma, meningiomas, medullomas, fibromas of the heart and ovary, and carcinomas of the lung, ovary, kidney and esophagus. Characterization of sporadic tumors will generally require analysis of tumor cell DNA, conveniently with a biopsy sample. A wide range of mutations are found in sporadic cases, up to and including deletion of the entire long arm of chromosome 9. Oncogenic mutations may delete one or more exons, e.g. 8 and 9, may affect the amino acid sequence such as of the extracellular loops or transmembrane domains, may cause truncation of the protein by introducing a frameshift or stop codon, etc. Specific examples of oncogenic mutations include a C to T transition at nt 523 and deletions encompassing exon 9. C to T transitions are characteristic of ultraviolet mutagenesis, as expected with cases of skin cancer.

Biochemical studies may be performed to determine whether a candidate sequence variation in the ptc coding region or control regions is oncogenic. For example, a change in the promoter or enhancer sequence that downregulates expression of patched may result in predisposition to cancer. Expression levels of a candidate variant allele are compared to expression levels of the normal allele by various methods known in the art. Methods for determining promoter or enhancer strength include quantitation of the expressed mRNA or ptc protein; insertion of the variant control element into a vector with a reporter gene such as β-galactosidase, chloramphenical acetyltransferase, etc. that provides for convenient quantitation- and the like. Nuclear run-off assays are another convenient means for measuring promoter/enhancer activity. The activity of the encoded ptc protein may be determined by comparison with the wild-type protein, e.g. by detection of transcriptional regulation of TGF or Wnt family genes, Gli genes, ptc itself, or reporter gene fusions involving transcriptional regulatory sequences of these target genes.

The term "patched-dependent gene", or "a gene which is regulated in a patched-dependent manner", refers to genes, such as Gli or patched, etc, whose level of expression is regulated at least in part by the presence of a patched protein in the cell, e.g., can be controlled by patched-dependent intracellular signals.

A human patched gene (SEQ ID NO:18) has a 4.5 kb open reading frame encoding a protein of 1447 amino acids. Including coding and noncoding sequences, it is about 89% identical at the nucleotide level to the mouse patched gene (SEQ ID NO:9). A mouse patched gene (SEQ ID NO:9) encodes a protein (SEQ ID NO:10) that has about 38% identical amino acids to *Drosophila* ptc (SEQ ID NO:6), over about 1,200 amino acids. The butterfly homolog (SEQ ID NO:4) is 1,300 amino acids long and overall has a 50% amino acid identity to fly ptc (SEQ ID NO:6). A 267 by exon from the beetle patched gene encodes an 89 amino acid protein fragment, which was found to be 44% and 51% identical to the corresponding regions of fly and butterfly ptc respectively.

The DNA sequence encoding ptc may be cDNA, RNA, genomic DNA or synthetic, and includes fragments of the full-length coding sequence. The term "patched gene" shall be intended to mean the open reading frame encoding specific ptc polypeptides, as well as, as appropriate, adjacent intronic sequences and 5' and 3' non-coding nucleotide sequences involved in the regulation of expression, up to about 1 kb beyond the coding region, in either direction. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons, 3' and 5' non-coding regions. Normally mRNA species have contiguous exons, with the intervening introns deleted, to create a continuous open reading frame encoding ptc.

The genomic ptc sequence has a non-contiguous open reading frame, where introns interrupt the coding regions. A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb of flanking genomic DNA at either the 5' or 3' end of the coding region. The genomic DNA may be isolated as a fragment of 50 kbp or smaller; and substantially free of flanking chromosomal sequence.

The nucleic acid compositions of the subject invention encode all or a part of the subject polypeptides. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

A variety of techniques are known in the art for generating fragments of the subject patched proteins, particularly those which retain the ability to bind hedgehog and/or alter the level of expression of a patched-dependent gene when expressed in a cell. To further illustrate the state of the art of combinatorial mutagenesis, it is noted that the review article of Gallop et al. (1994) *J Med Chem* 37:1233 describes the general state of the art of combinatorial libraries as of the earlier 1990's. In particular, Gallop et al state at page 1239 "[s]creening the analog libraries aids in determining the minimum size of the active sequence and in identifying those residues critical for binding and intolerant of substitution". In addition, the Ladner et al. PCT publication WO90/02809, the Goeddel et al. U.S. Pat. No. 5,223,408, and the Markland et al. PCT publication WO92/15679 illustrate specific techniques which one skilled in the art could utilize to generate libraries of patched variants which can be rapidly screened to identify variants/fragments which retained a particular activity, such as signal transduction (measured by transcriptional regulation) and/or the ability to bind hedgehog polypeptides. These techniques are exemplary of the art and demonstrate that large libraries of related variants/truncants can be generated and assayed to isolate particular variants without undue experimentation. Gustin et al. (1993) *Virology* 193:653, and Bass et al. (1990) *Proteins: Structure, Function and Genetics* 8:309-314 also describe other exemplary techniques from the art which can be adapted as means for generating mutagenic variants of patched polypeptides.

Indeed, it is plain from the combinatorial mutagenesis art that large scale mutagenesis of patched proteins, without any preconceived ideas of which residues were critical to the biological function, and generate wide arrays of variants having equivalent biological activity. In fact, it is the ability of combinatorial techniques to screen billions of different variants by high throughput analysis that removes any requirement of a priori understanding or knowledge of critical residues.

To illustrate, the amino acid sequences for a population of patched homologs or other related proteins are aligned, preferably to promote the highest homology possible. Such a population of variants can include, for example, the subject patched homologs from various vertebrate and invertebrate species. Amino acids which appear at each position of the aligned sequences are selected to create a degenerate set of combinatorial sequences. In a preferred embodiment, the variegated library of patched variants is generated by combinatorial mutagenesis at the nucleic acid level, and is encoded by a variegated gene library. Such techniques have been employed in the directed evolution of other proteins (see, for example, Scott et al. (1990) *Science* 249:386-390; Roberts et al. (1992) *PNAS* 89:2429-2433; Devlin et al. (1990) *Science* 249: 404-406; Cwirla et al. (1990) *PNAS* 87: 6378-6382; as well as U.S. Pat. Nos. 5,223,409, 5,198,346, and 5,096,815).

A wide range of techniques are known in the art for screening gene products of combinatorial libraries made by point or tuncation mutations, and for screening cDNA libraries for gene products having a certain property. Such techniques will be generally adaptable for rapid screening of the gene libraries generated by the combinatorial mutagenesis of patched homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. For example, simple binding assays can be performed with hedgehog protein. In other embodiments, the ability of the library gene to alter the transcriptional rate of a reporter gene can be detected. Each of such illustrative assays are amenable to high through-put analysis as necessary to screen large numbers of degenerate patched sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays such as phage display. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811-7815; Yourvan et al., 1992, *Parallel Problem Solving from Nature*, 2., In Maenner and Manderick, eds., Elsevir Publishing Co., Amsterdam, pp. 401-410; Delgrave et al., 1993, *Protein Engineering* 6(3):327-331).

In preferred embodiments, the subject patched protein is a fragment of the full length protein which binds to hedgehog polypeptides, e.g., including one or both of the substantial extracellular (hydrophilic) domains, such as corresponding to residues Asn120-Ser438 and/or Arg770-Trp1027 of the human patched protein. Other preferred embodiments of patched polypeptides include fragments which are at least 50, 75, 100, 150 and 200 amino acid residues in length. Such forms of the patched protein can be provided in soluble form, as for example a preparation of one of the extracellular domains, or a preparation of both of the extracellular domains which are covalently connected by an unstructured linker (see, for example, Huston et al. (1988) PNAS 85:4879; and U.S. Pat. No. 5,091,513). In other embodiments, the protein can be provided as part of a liposomal preparation or expressed on the surface of a cell.

In yet other preferred embodiments, the patched polypeptide is at least 60, 65, 75, 85, 90, or 95 percent identical with the human or mouse patched sequences of the appended sequence listing.

The ptc genes are isolated and obtained in substantial purity, generally as other than an intact mammalian chromosome. Usually, the DNA will be obtained substantially free of other nucleic acid sequences that do not include a ptc sequence or fragment thereof, generally being at least about 50%, usually at least about 90% pure and are typically "recombinant", i.e. flanked by one or more nucleotides with which it is not normally associated on a naturally occurring chromosome.

The DNA sequences are used in a variety of ways. They may be used as probes for identifying other patched genes. Mammalian homologs have substantial sequence similarity to the subject sequences, i.e. at least 75%, usually at least 90%, more usually at least 95% sequence identity with the nucleotide sequence of the subject DNA sequence. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J Mol Biol* 215:403-10.

Nucleic acids having sequence similarity are detected by hybridization under low stringency conditions, for example, at 50 C and 10×SSC (0-9 M saline/0.09 M sodium citrate) and remain bound when subjected to washing at 55° C. in 1×SSC. By using probes, particularly labeled probes of DNA sequences, one can isolate homologous or related genes. The source of homologous genes may be any mammalian species, e.g. primate species, particularly human-murines, such as rats and mice, canines, felines, bovines, ovines, equines, etc.

The DNA may also be used to identify expression of the gene in a biological specimen. The manner in which one probes cells for the presence of particular nucleotide sequences, as genomic DNA or RNA, is well-established in the literature and does not require elaboration here. Conveniently, a biological specimen is used as a source of mRNA. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g., nitrocellulose and then probed with a fragment of the subject DNA as a probe. Other techniques may also find use. Detection of mRNA having the subject sequence is indicative of patched gene expression in the sample.

The subject nucleic acid sequences may be modified for a number of purposes, particularly where they will be used intracellularly, for example, by being joined to a nucleic acid cleaving agent, e.g. a chelated metal ion, such as iron or chromium for cleavage of the gene; as an antisense sequence, or the like. Modifications may include replacing oxygen of the phosphate esters with sulfur or nitrogen, replacing the phosphate with phosphoramide, etc.

A number of methods are available for analyzing genomic DNA sequences. Where large amounts of DNA are available, the genomic DNA is used directly. Alternatively, the region of interest is cloned into a suitable vector and grown in sufficient quantity for analysis, or amplified by conventional techniques, such as the polymerase chain reaction (PCR). The use of the polymerase chain reaction is described in Saiki, et al. (1985) *Science* 239:487, and a review of current techniques may be found in Sambrook, et al. *Molecular Cloning: A Laboratory Manual*, CSH Press 1989, pp. 14.2-14.33.

A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-Xrhodamine (ROX), 6-carboxy-2',4',7', 4,7-hexachlorofluorescein (HEX), 5-carboxyfluorescein (5-FAM) or N,N,N',N'-tetramethyl-6-carboxyrhodamine (TAMRA), radioactive labels, e.g. 32P, 35S, 3H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label Into the amplification product.

The amplified or cloned fragment may be sequenced by dideoxy or other methods, and the sequence of bases compared to the normal ptc sequence. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The hybridization pattern of a control and variant sequence to an array of oligonucleotide probes immobilized on a solid support, as described in WO 95/11995, may also be used as a means of detecting the presence of variant sequences. Alternatively, where a predisposing mutation creates or destroys a recognition site for a restriction endonuclease, the fragment is digested with that endonuclease, and the products size fractionated to determine whether the fragment was digested. Fractionation is performed by gel electrophoresis, particularly acrylamide or agarose gels.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a ptc gene under conditions such that hybridization and amplification of the ptc gene (if present) occurs, and (iv) detecting the presence or absence of an amplification product, or detecting the size of the amplification product and comparing the length to a control sample.

In yet another exemplary embodiment, aberrant methylation patterns of a ptc gene can be detected by digesting genomic DNA from a patient sample with one or more restriction endonucleases that are sensitive to methylation and for which recognition sites exist in the ptc gene (including in the flanking and intronic sequences). See, for example, Buiting et al., (1994) *Human Mol Genet* 3:893-895. Digested DNA is separated by gel electrophoresis, and hybridized with probes derived from, for example, genomic or cDNA sequences. The methylation status of the ptc gene can be determined by comparison of the restriction pattern generated from the sample DNA with that for a standard of known methylation.

In still another embodiment, a diagnostic assay is provided which detects the ability of a ptc gene product, e.g., recombinantly expressed from a gene isolated from a biopsied cell, to bind to other proteins, e.g., upstream (hedgehog) or downstream of ptc. For instance, it will be desirable to detect ptc mutants which bind with lower binding affinity for hedgehog proteins. Such mutants may arise, for example, from fine mutations, e.g., point mutants, which may be impractical to detect by the diagnostic DNA sequencing techniques or by the immunoassays described above. The present invention accordingly further contemplates diagnostic screening assays which generally comprise cloning one or more ptc genes from the sample cells, and expressing the cloned genes under conditions which permit detection of an interaction between that recombinant gene product and a ptc-binding protein, e.g., a hedgehog protein. As will be apparent from the description of the various drug screening assays set forth below, a wide variety of techniques can be used to determine the ability of a ptc protein to bind to other cellular components.

The subject nucleic acids can be used to generate transgenic animals or site specific gene modifications in cell lines. Transgenic animals may be made through homologous recombination, where the normal patched locus is altered. Alternatively, a nucleic acid construct is randomly integrated into the genome, Vectors for stable integration include plasmids, retroviruses and other animal viruses, YACS, and the like.

The modified cells or animals are useful in the study of patched function and regulation. For example, a series of small deletions and/or substitutions may be made in the patched gene to determine the role of different exons in oncogenesis, signal transduction, etc. Of particular interest are transgenic animal models for carcinomas of the skin, where expression of ptc is specifically reduced or absent in skin cells. An alternative approach to transgenic models for this disease are those where one of the mammalian hedgehog genes, e.g. Shh, lhh, Dhh, are upregulated in skin cells, or in other cell types. For models of skin abnormalities, one may use a skin-specific promoter to drive expression of the transgene, or other inducible promoter that can be regulated in the animal model. Such promoters include keratin gene promoters. Specific constructs of interest include anti-sense ptc, which will block ptc expression, expression of dominant negative ptc mutations, and over-expression of HH genes. A detectable marker, such as lacZ may be introduced into the patched locus, where upregulation of patched expression will result in an easily detected change in phenotype.

One may also provide for expression of the patched gene or variants thereof in cells or tissues where it is not normally expressed or at abnormal times of development. Thus, mouse models of spina bifida or abnormal motor neuron differentiation in the developing spinal cord are made available. In addition, by providing expression of ptc protein in cells in which it is otherwise not normally produced, one can induce changes in cell behavior, e.g. through ptc mediated transcription modulation.

DNA constructs for homologous recombination will comprise at least a portion of the patched or hedgehog gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527-537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on basal cell carcinomas.

The subject gene may be employed for producing all or portions of the patched protein. For expression, an expression cassette may be employed, providing for a transcriptional and translational initiation region, which may be inducible or constitutive, the coding region under the transcriptional control of the transcriptional initiation region, and a transcriptional and translational termination region. Various transcriptional initiation regions may be employed which are functional in the expression host.

Figure 2:
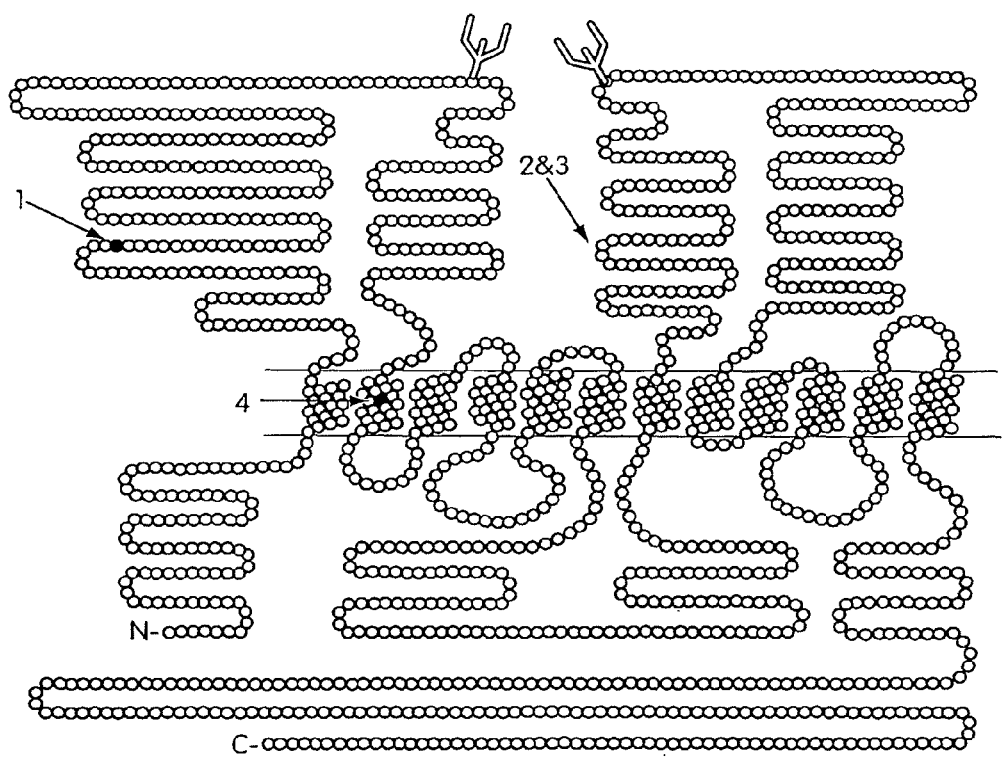
FIG. 2 shows a summary of mutations found in the human patched gene locus that are associated with basal cell nevus syndrome. Mutation (1) is found in sporadic basal cell carcinoma, and is a C to T transition in exon 3 at nucleotide 523 of the coding sequence, changing Leu 175 to Phe in the first extracellular loop. Mutations 2-4 are found in hereditary basal carcinoma nevus syndrome. (2) is an insertion of 9 by at nucleotide 2445, resulting in the insertion of an additional 3 amino acids after amino acid 815. (3) is a deletion of 11 bp, which removes nt 2442-2452 from the coding sequence. The resulting frameshift truncates the open reading frame after amino acid 813, 'just after the seventh transmembrane domain. (4) is a G to C alteration that changes two conserved nucleotides of the 3' splice site adjacent to exon 10, creating a non-functional splice site that truncates the protein after amino acid 449, in the second transmembrane region.

Specific ptc peptides of interest include the extracellular domains, particularly in the human mature protein, aa 120 to 437, and aa 770 to 1027. These peptides may be used as immunogens to raise antibodies that recognize the protein in an intact cell membrane. The cytoplasmic domains, as shown in FIG. 2, (the amino terminus and carboxy terminus) are of interest in binding assays to detect ligands involved in signaling mediated by ptc.

The peptide may be expressed in prokaryotes or eukaryotes in accordance with conventional ways, depending upon the purpose for expression. For large scale production of the protein, a unicellular organism or cells of a higher organism, e.g. eukaryotes such as vertebrates, particularly mammals, may be used as the expression host, such as *E. coli, B, subthis, S. cerevisiae*, and the like. In many situations, it may be desirable to express the patched gene in a mammalian host, whereby the patched gene will be glycosylated, and transported to the cellular membrane for various studies.

With the availability of the protein in large amounts by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. By pure is intended free of other proteins, as well as cellular debris.

The polypeptide is used for the production of antibodies, where short fragments provide for antibodies specific for the particular polypeptide, whereas larger fragments or the entire gene allow for the production of antibodies over the surface of the polypeptide or protein. Antibodies may be raised to the normal or mutated forms of ptc—The extracellular domains of the protein are of interest as epitopes, particular antibodies that recognize common changes found in abnormal, oncogenic ptc, which compromise the protein activity. Antibodies may be raised to isolated peptides corresponding to these domains, or to the native protein, e.g. by immunization with cells expressing ptc, immunization with liposomes having ptc inserted in the membrane, etc. Antibodies that recognize the extracellular domains of ptc are useful in diagnosis, typing and staging of human carcinomas.

Antibodies are prepared in accordance with conventional ways, where the expressed polypeptide or protein may be used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen may be isolated, the splenocytes immortalized, and then screened for high affinity antibody binding. The immortalized cells, e.g. hybridomas, producing the desired antibodies may then be expanded. For further description, see Monoclonal Antibodies—A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in $E.$ $coli$, and the heavy and light chains may be mixed to further enhance the affinity of the antibody.

The antibodies find particular use in diagnostic assays for developmental abnormalities, basal cell carcinomas and other tumors associated with mutations in ptc. Staging, detection and typing of tumors may utilize a quantitative immunoassay for the presence or absence of normal ptc. Alternatively, the presence of mutated forms of ptc may be determined. A reduction in normal ptc and/or presence of abnormal ptc is indicative that the tumor is ptc-associated.

A sample is taken from a patient suspected of having a ptc-associated tumor, developmental abnormality or BCNS. Samples, as used herein, include biological fluids such as blood, cerebrospinal fluid, tears, saliva, lymph, dialysis fluid and the like-organ or tissue culture derived fluids, and fluids extracted from physiological tissues. Also included in the term are derivatives and fractions of such fluids. Biopsy samples are of particular interest, e.g. skin lesions, organ tissue fragments, etc. Where metastasis is suspected, blood samples may be preferred. The number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

Diagnosis may be performed by a number of methods. The different methods all determine the absence or presence of normal or abnormal ptc in patient cells suspected of having a mutation in ptc. For example, detection may utilize staining of intact cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well-known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and ptc in a lysate. Measuring the concentration of ptc binding in a sample or fraction thereof may be accomplished by a variety of specific assays. A conventional sandwich type assay may be used. For example, a sandwich assay may first attach ptc-specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of normal and/or abnormal ptc is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7-8, is used as a wash medium. From one to six washes may be employed, with sufficient volume to thoroughly wash nonspecifically bound proteins present in the sample.

After washing, a solution containing a second antibody is applied. The antibody will bind ptc with sufficient specificity such that it can be distinguished from other components present. The second antibodies may be labeled to facilitate direct, or indirect quantification of binding. Examples of labels that permit direct measurement of second receptor binding include radiolabels, such as $^3$H or $^{125}$I, fluorescers, dyes, beads, chemilumninescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for ptc as desired, conveniently using a labeling method as described for the sandwich assay.

Other diagnostic assays of interest are based on the functional properties of ptc protein itself. Such assays are particularly useful where a large number of different sequence changes lead to a common phenotype, i.e., loss of protein function leading to oncogenesis or developmental abnormality. For example, a functional assay may be based on the transcriptional changes mediated by hedgehog and patched gene products. Addition of soluble Hh to embryonic stem cells causes induction of transcription in target genes. The presence of functional ptc can be determined by its ability to antagonize Hh activity. Other functional assays may detect the transport of specific molecules mediated by ptc, in an intact cell or membrane fragment. Conveniently, a labeled substrate is used, where the transport in or out of the cell can be quantitated by radiography, microscopy, flow cytometry, spectrophotometry, etc. Other assays may detect conformational changes, or changes in the subcellular localization of patched protein.

By providing for the production of large amounts of patched protein, one can identify ligands or substrates that bind to, modulate or mimic the action of patched. A common feature in basal cell carcinoma is the loss of adhesion between epidermal and dermal layers, indicating a role for ptc in maintaining appropriate cell adhesion. Areas of investigation include the development of cancer treatments, wound healing, adverse effects of aging, metastasis, etc.

Drug screening identifies agents that provide a replacement for ptc function in abnormal cells. The role of ptc as a tumor suppressor indicates that agents which mimic its function, in terms of transmembrane transport of molecules, transcriptional down-regulation, etc., will inhibit the process of oncogenesis. These agents may also promote appropriate cell adhesion in wound healing and aging, to reverse the loss of adhesion observed in metastasis, etc. Conversely, agents that reverse ptc function may stimulate controlled growth and healing. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions, transporter function, etc.

The term "agent" as used herein describes any molecule, e.g. protein or pharmaceutical, with the capability of altering or mimicking the physiological function of patched. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or a combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce nonspecific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° and 40° C. Incubation periods are selected for optimum activity, but may also be optimized to facilitate rapid high-throughput screening. Typically between 0.1 and 1 hours will be sufficient.

Other assays of interest detect agents that mimic patched function, such as repression of target gene transcription, transport of patched substrate compounds, etc. For example, an expression construct comprising a patched gene may be introduced into a cell line under conditions that allow expression. The level of patched activity is determined by a functional assay, as previously described. In one screening assay, candidate agents are added in combination with a Hh protein, and the ability to overcome Hh antagonism of ptc is detected. In another assay, the ability of candidate agents to enhance ptc function is determined. Alternatively, candidate agents are added to a cell that lacks functional ptc, and screened for the ability to reproduce ptc in a functional assay.

In one embodiment, the drug screening assay is a cell-based assay which detects the ability of a compound to alter patched-dependent gene transcription. By selecting transcriptional regulatory sequences from genes whose expression is regulated by patched signal transduction, e.g. from patched, GLI, hedgehog or PTHrP genes, e.g., regulatory sequences that are responsible for the up- or down regulation of these genes in response to patched signalling, and operatively linking such promoters to a reporter gene, one can derive a transcription based assay which is sensitive to the ability of a specific test compound to modify patched signalling pathways. Expression of the reporter gene, thus, provides a valuable screening tool for the development of compounds that act as agonists or antagonists of patched.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc signaling. To identify potential regulatory elements responsive to ptc signaling present in the transcriptional regulatory sequence of a target gene, nested deletions of genomic clones of the target gene can be constructed using standard techniques. See, for example, *Current Protocols in Molecular Biology*, Ausubel, F. M. et al. (eds.) Greene Publishing Associates, (1989); U.S. Pat. No. 5,266,488; Sato et al. (1995) *J Biol Chem* 270:10314-10322; and Kube et al. (1995) *Cytokine* 7:1-7. A nested set of DNA fragments from the gene's 5'-flanking region are placed upstream of a reporter gene, such as the luciferase gene, and assayed for their ability to direct reporter gene expression in patched expressing cells. Host cells transiently transfected with reporter gene constructs can be scored for the induction of expression of the reporter gene in the presence and absence of hedgehog to determine regulatory sequences which are responsive to patched-dependent signalling.

In practicing one embodiment of the assay, a reporter gene construct is inserted into the reagent cell in order to generate a detection signal dependent on second messengers generated by induction with hedgehog protein. Typically, the reporter gene construct will include a reporter gene in operative linkage with one or more transcriptional regulatory elements responsive to the hedgehog activity, with the level of expression of the reporter gene providing the hedgehog-dependent detection signal. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic activity. The amount of expression from the reporter gene is then compared to the amount of expression in either the same cell in the absence of the test compound (or hedgehog) or it may be compared with the amount of transcription in a substantially identical cell that lacks the target receptor protein. Any statistically or otherwise significant difference in the amount of transcription indicates that the test compound has in some manner altered the signal transduction of the patched protein, e.g., the test compound is a potential ptc therapeutic.

As described in further detail below, in preferred embodiments the gene product of the reporter is detected by an intrinsic activity associated with that product. For instance, the reporter gene may encode a gene product that, by enzymatic activity, gives rise to a detection signal based on color, fluorescence, or luminescence. In other preferred embodiments, the reporter or marker gene provides a selective growth advantage, e.g., the reporter gene may enhance cell viability, relieve a cell nutritional requirement, and/or provide resistance to a drug.

Preferred reporter genes are those that are readily detectable. The reporter gene may also be included in the construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (deWet et al. (1987), Mol. Cell. Biol. 7:725-737); bacterial luciferase (Engebrecht and Silverman (1984), PNAS 1: 4154-4158; Baldwin et al. (1984), Biochemistry 23: 3663-3667); alkaline phosphatase (Toh et al. (1989) Eur. J. Biochem. 182: 231-238, Hall et al. (1983) J. Mol. Appl. Gen. 2: 101), human placental secreted alkaline phosphatase (Cullen and Malim (1992) Methods in Enzymol. 216:362-368).

Transcriptional control elements which may be included in a reporter gene construct include, but are not limited to, promoters, enhancers, and repressor and activator binding sites. Suitable transcriptional regulatory elements may be derived from the transcriptional regulatory regions of genes whose expression is induced after modulation of a patched signal transduction pathway. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

The compounds having the desired pharmacological activity may be administered in a physiologically acceptable carrier to a host for treatment of cancer or developmental abnormalities attributable to a defect in patched function. The compounds may also be used to enhance patched function in wound healing, aging, etc. The inhibitory agents may be administered in a variety of ways, orally, topically, parenterally e.g. subcutaneously, intraperitoneally, by viral infection, intravascularly, etc. Topical treatments are of particular interest. Depending upon the manner of introduction, the compounds may be formulated in a variety of ways. The concentration of therapeutically active compound in the formulation may vary from about 0.1-100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The gene or fragments thereof may be used as probes for identifying the 5' non-coding region comprising the transcriptional initiation region, particularly the enhancer regulating the transcription of patched. By probing a genomic library, particularly with a probe comprising the 5' coding region, one can obtain fragments comprising the 5' non-coding region. If necessary, one may walk the fragment to obtain further 5' sequence to ensure that one has at least a functional portion of the enhancer. It is found that the enhancer is proximal to the 5' coding region, a portion being in the transcribed sequence and downstream from the promoter sequences. The transcriptional initiation region may be used for many purposes, studying embryonic development, providing for regulated expression of patched protein or other protein of interest during embryonic development or thereafter, and in gene therapy.

The gene may also be used for gene therapy. Vectors useful for introduction of the gene include plasmids and viral vectors. Of particular interest are retroviral-based vectors, e.g. moloney murine leukemia virus and modified human immunodeficiency virus-adenovirus vectors, etc. Gene therapy may be used to treat skin lesions, an affected fetus, etc., by transfection of the normal gene into embryonic stem cells or into other fetal cells. A wide variety of viral vectors can be employed for transfection and stable integration of the gene into the genome of the cells. Alternatively, micro-injection may be employed, fusion, or the like for introduction of genes into a suitable host cell. See, for example, Dhawan et al. (1991) *Science* 254:1509-1512 and Smith et al. (1990) *Molecular and Cellular Biology* 3268-3271.

The following examples are offered by illustration not by way of limitation.

EXPERIMENTAL

Methods and Materials

PCR on Mosquito (*Anopheles gambiae*) Genomic DNA. PCR primers were based on amino acid stretches of fly ptc that were not likely to diverge over evolutionary time and were of low degeneracy. Two such primers (P2R1 (SEQ ID NO-14)-GGACGAATTCAARGTNCAYCARYTNTGG, P4R1: (SEQ ID NO:15) GGACGAATTCCYTCCCARAARCANTC, (the underlined sequences are Eco RI linkers) amplified an appropriately sized band from mosquito genomic DNA using the PCR. The program conditions were as follows:

94 C 4 min; 72 C Add Taq;
[49 C 30 sec.; 72 C 90 sec.; 94 C 15 sec] 3 times
[94 C 15 sec.; 50 C 30 sec.; 72 C 90 sec] 35 times
72 C 10 min; 4 C hold This band was subcloned into the EcoRV site of pBluescript II and sequenced using the USB Sequence kit.

Screen of a Butterfly cDNA Library with Mosquito PCR Product. Using the mosquito PCR product (SEQ ID NO:7) as a probe, a 3 day embryonic *Precis coenia* gt10 cDNA library (generously provided by Sean Carroll) was screened. Filters were hybridized at 65° C. overnight in a solution containing 5×SSC, 10% dextran sulfate, 5×Denhardt's, 200 µg/ml sonicated salmon sperm DNA, and 0.5% SDS. Filters were washed in 0.1×SSC, 0.1% SDS at room temperature several times to remove nonspecific hybridization. Of the 100,000 plaques initially screened, 2 overlapping clones, L1 and L2, were isolated, which corresponded to the N terminus of butterfly ptc. Using L2 as a probe, the library filters were rescreened and 3 additional clones (L5, L7, L8) were isolated which encompassed the remainder of the ptc coding sequence. The full length sequence of butterfly ptc (SEQ ID NO:3) was determined by ABI automated sequencing.

Screen of a *Tribolium* (beetle) Genomic Library with Mosquito PCR Product and 900 bp Fragment from the Butterfly Clone. A gem11 genomic library from *Tribolium casteneum* (gift of Rob Dennell) was probed with a mixture of the mosquito PCR (SEQ ID NO:7) product and BstXI/EcoRI fragment of L2. Filters were hybridized at 55 C overnight and washed as above. Of the 75,000 plaques screened, 14 clones were identified and the SacI fragment of T8 (SEQ ID NO:1), which crosshybridized with the mosquito and butterfly probes, was subcloned into pBluescript.

PCR on Mouse cDNA Using Degenerate Primers Derived from Regions Conserved in the Four Insect Homologues. Two degenerate PCR primers (P4REV-(SEQ ID NO:16) GGACGAATTCYTNGANTGYTTYTGGGA-P22-(SEQ ID NO:17) CATACCAGCCAAGCTTGTCIGGCCART-GCAT) were designed based on a comparison of ptc amino acid sequences from fly (*Drosophila melanogaster*) (SEQ ID NO:6), mosquito (*Anopheles gambiae*) (SEQ ID NO:8), butterfly (*Precis coenia*) (SEQ ID NO:4), and beetle (*Tribolium casteneum*) (SEQ ID NO:2). I represents inosine, which can form base pairs with all four nucleotides. P22 was used to reverse transcribe RNA from 12.5 dpc mouse limb bud (gift from David Kingsley) for 90 min at 37 C. PCR using P4REV (SEQ ID NO:17) and P22 (SEQ ID NO:18) was then performed on 1 1 of the resultant cDNA under the following conditions:

94 C 4 min; 72 C Add Taq;
[94 C 15 sec.-50 C 30 sec.-72 C 90 sec.] 35 times
72 C 10 min.-, 4 C hold PCR products of the expected size were subcloned into the TA vector (Invitrogen) and sequenced with the Sequenase Version 2.0 DNA Sequencing Kit (U.S. B.).

Using the cloned mouse PCR fragment as a probe, 300,000 plaques of a mouse 8.5 dpc gt10 cDNA library (a gift from Brigid Hogan) were screened at 65 C as above and washed in 2×SSC, 0.1% SDS at room temperature. 7 clones were isolated, and three (M2, M4, and M8) were subcloned into pBluescript II. 200,000 plaques of this library were rescreened using first, a 1.1 kb EcoRI fragment from M2 to identify 6 clones (M9-M16) and secondly a mixed probe containing the most N terminal (XhoI fragment from M2) and most C terminal sequences (BamHI/BgIII fragment from M9) to isolate 5 clones (M17-M21). M9, M10, M14, and M17-21 were subcloned into the EcoRI site of pBluescript II (Strategene).

RNA Blots and In Situ Hybridizations in Whole and Sectioned Mouse Embryos:

Northerns. A mouse embryonic Northern blot and an adult multiple tissue Northern blot (obtained from Clontech) were probed with a 900 by EcoR1 fragment from an N terminal coding region of mouse ptc. Hybridization was performed at 65° C. in 5×SSPE, 10×Denhardt's, 100 µg/ml sonicated salmon sperm DNA, and 2% SDS. After several short room temperature washes in 2×SSC, 0.05% SDS, the blots were washed at high stringency in 0.1×SSC, 0.1% SDS at 50° C.

In situ hybridization of sections: 7.75, 8.5, 11.5, and 13.5 dpc mouse embryos were dissected in PBS and frozen in Tissue-Tek medium at –80° C. 12-16 µm frozen sections were cut, collected onto VectaBond (Vector Laboratories) coated slides, and dried for 30-60 minutes at room temperature. After a 10 minute fixation in 4% paraformaldehyde in PBS, the slides were washed 3 times for 3 minutes in PBS, acetylated for 10 minutes in 0.25% acetic anhydride in triethanolamine, and washed three more times for 5 minutes in PBS. Prehybridization (50% formamide, 5×SSC, 250 µg/ml yeast tRNA, 500 µg/ml sonicated salmon sperm DNA, and 5×Denhardt's) was carried out for 6 hours at room temperature in 50% formamide/5×SSC humidified chambers. The probe, which consisted of 1 kb from the N-terminus of ptc, was added at a concentration of 200-1000 ng/ml into the same solution used for prehybridization, and then denatured for five minutes at 80° C. Approximately 75 µl of probe were added to each slide and covered with Parafilm. The slides were incubated overnight at 65° C. in the same humidified chamber used previously. The following day, the probe was washed successively in 5×SSC (5 minutes, 65° C.), 0.2×SSC (1 hour, 65° C.), and 0.2×SSC (10 minutes, room temperature). After five minutes in buffer B1 (0.1M maleic acid, 0.15 M NaCl, pH 7.5), the slides were blocked for 1 hour at room temperature in 1% blocking reagent (Boerhinger-Mannheim) in buffer B1, and then incubated for 4 hours in buffer B1 containing the DIG-AP conjugated antibody (Boerhinger-Mannheim) at a 1:5000 dilution. Excess antibody was removed during two 15 minute washes in buffer B1, followed by five minutes in buffer B3 (100 mM Tris, 100 mM NaCl, 5 mM MgCl2, pH 9.5). The antibody was detected by adding an alkaline phosphatase substrate (350 µl 75 mg/ml X-phosphate in DMF, 450 µl 50 mg/ml NBT in 70% DMF in 100 mls of buffer B3) and allowing the reaction to proceed overnight in the dark. After a brief rinse in 10 mM Tris, 1 mM EDTA, pH 8.0, the slides were mounted with Aquamount (Lerner Laboratories).

Drosophila 5-transcriptional initiation region-gal constructs. A series of constructs were designed that link different regions of the ptc promoter from Drosophila to a LacZ reporter gene in order to study the cis regulation of the ptc expression pattern. See FIG. 1. A 10.8 kb BamHI/BspMI fragment comprising the 5'-non-coding region of the mRNA at its 3'-terminus was obtained and truncated by restriction enzyme digestion as shown in FIG. 1. These expression cassettes were introduced into Drosophila lines using a P-element vector (Thummel et al. (1988) Gene 74:445-456), which were injected into embryos, providing flies which could be grown to produce embryos. (See Spradling and Rubin (1982) Science 218:341-347 for a description of the procedure.) The vector used a pUC8 background into which was introduced the white gene to provide for yellow eyes, portions of the P-element for integration, and the constructs were inserted into a polylinker upstream from the LacZ gene. The resulting embryos, larvae, and adults were stained using antibodies to LacZ protein conjugated to HRP and the samples developed with OPD dye to identify the expression of the LacZ gene. The staining pattern in embryos is described in FIG. 1, indicating whether there was staining during the early and late development of the embryo.

Isolation of a Mouse ptc Gene. Homologues of fly ptc (SEQ ID NO:6) were isolated from three insects: mosquito, butterfly and beetle, using either PCR or low stringency library screens. PCR primers to six amino acid stretches of ptc of low mutatability and degeneracy were designed. One primer pair, P2 and P4, amplified an homologous fragment of ptc from mosquito genomic DNA that corresponded to the first hydrophilic loop of the protein. The 345 bp PCR product (SEQ ID NO:7) was subcloned and sequenced and when aligned to fly ptc, showed 67% amino acid identity.

The cloned mosquito fragment was used to screen a butterfly gt 10 cDNA library. Of 100,000 plaques screened, five overlapping clones were isolated and used to obtain the full length coding sequence. The butterfly ptc homologue (SEQ ID NO:4) is 1,311 amino acids long and overall has 50% amino acid identity (72% similarity) to fly ptc. With the exception of a divergent C-terminus, this homology is evenly spread across the coding sequence. The mosquito PCR clone (SEQ ID NO:7) and a corresponding fragment of butterfly cDNA were used to screen a beetle gem11 genomic library. Of the plaques screened, 14 clones were identified. A fragment of one clone (T8), which hybridized with the original probes, was subcloned and sequenced. This 3 kb piece contains an 89 amino acid exon (SEQ ID NO:2) which is 44% and 51% identical to the corresponding regions of fly and butterfly ptc respectively.

Using an alignment of the four insect homologues in the first hydrophilic loop of the ptc, two PCR primers were designed to a five and six amino acid stretch which were identical and of low degeneracy. These primers were used to isolate the mouse homologue using RT-PCR on embryonic limb bud RNA. An appropriately sized band was amplified and upon cloning and sequencing, it was found to encode a protein 65% identical to fly ptc. Using the cloned PCR product and subsequently, fragments of mouse ptc cDNA, a mouse embryonic cDNA library was screened. From about 300,000 plaques, 17 clones were identified and of these, 7 form overlapping cDNA's that comprise most of the protein-coding sequence (SEQ ID NO:9).

Developmental and Tissue Distribution of Mouse ptc RNA. In both the embryonic and adult Northern blots, the ptc probe detects a single 8 kb message. Further exposure does not reveal any additional minor bands. Developmentally, ptc mRNA is present in low levels as early as 7 dpc and becomes quite abundant by 11 and 15 dpc. While the gene is still present at 17 dpc, the Northern blot indicates a clear decrease in the amount of message at this stage. In the adult, ptc RNA is present in high amounts in the brain and lung, as well as in moderate amounts in the kidney and liver. Weak signals are detected in heart, spleen, skeletal muscle, and testes.

In situ Hybridization of Mouse ptc in Whole and Section Embryos. Northern analysis indicates that ptc mRNA is present at 7 dpc, while there is no detectable signal in sections from 7.75 dpc embryos. This discrepancy is explained by the low level of transcription. In contrast, ptc is present at high levels along the neural axis of 8.5 dpc embryos. By 11.5 dpc, ptc can be detected in the developing lung buds and gut, consistent with its adult Northern profile. In addition, the gene is present at high levels in the ventricular zone of the central nervous system, as well as in the zona limitans of the prosencephalon. ptc is also strongly transcribed in the condensing cartilage of 11.5 and 13.5 dpc limb buds, as well as in the ventral portion of the somites, a region which is prospective sclerotome and eventually forms bone in the vertebral column ptc is present in a wide range of tissues from endodermal, mesodermal and ectodermal origin supporting its fundamental role in embryonic development.

Isolation of the Human ptc Gene. To isolate human ptc (hptc), 2×105 plaques from a human lung cDNA library (HL3022a, Clonetech) were screened with a 1kbp mouse ptc fragment, M2-2. Filters were hybridized overnight at reduced stringency (60° C. in 5×SSC, 10% dextran sulfate, 5×Denhardt's, 0.2 mg/ml sonicated salmon sperm DNA, and 0.5% SDS). Two positive plaques (H1 and H2) were isolated, the inserts cloned into pBluescript, and upon sequencing, both contained sequence highly similar to the mouse ptc homolog. To isolate the 5' end, an additional 6×105 plaques were screened in duplicate with M2-3 EcoRI and M2-3 Xho I (containing 5' untranslated sequence of mouse ptc) probes. Ten plaques were purified and of these, inserts were subcloned into pBluescript. To obtain the full coding sequence, H2 was fully and H14, H20, and H21 were partially sequenced. The 5.1 kbp of human ptc sequence (SEQ ID NO:18) contains an open reading frame of 1447 amino acids (SEQ ID NO:19) that is 96% identical and 98% similar to mouse ptc. The 5' and 3' untranslated sequences of human ptc (SEQ ID NO:18) are also highly similar to mouse ptc (SEQ ID NO:19) suggesting conserved regulatory sequence.

Comparison of Mouse, Human, Fly and Butterfly Sequences. The deduced mouse ptc protein sequence (SEQ ID NO:10) has about 38% identical amino acids to fly ptc over about 1,200 amino acids. This amount of conservation is dispersed through much of the protein excepting the C-terminal region. The mouse protein also has a 50 amino acid insert relative to the fly protein. Based on the sequence conservation of ptc and the functional conservation of hedgehog between fly and mouse, one concludes that ptc functions similarly in the two organisms. A comparison of the amino acid sequences of mouse (mptc) (SEQ ID NO:10), human (hptc) (SEQ ID NO:19), butterfly (bptc) (SEQ ID NO:4) and drosophila (ptc) (SEQ ID NO:6) is shown in the following table.

```
ALIGNMENT OF HUMAN, MOUSE, FLY, AND BUTTERFLY PTC HOMOLOGS
HPTC  MASAGNAAEPQDR--GGGGSGCIGAPGRPAGGGRRRRTGGLRRAAAPDRDYLHRPSYCDA
MPTC  MASAGNAA--------------GALGRQAGGGRRRRTGGPHRA-APDRDYLHRPSYCDA
PTC   M-----DRDSLPRVPDTHGD--VVDE---------KLFSDL---------YI-RTSWVDA
BPTC  MVAPDSEAPSNRRITAAHESPCATEA---------RHSADL---------YI-RTSWVDA
         *                          .  ..          *. * * **
```

```
HPTC   AFALEQISKGKATGRKAPLWLRAKFQRLLFKLGCYIQKNCGKFLVVGLLIPGAPAVGLKA
MPTC   AFALEQISKGKATGRKAPLWLRAKFQRLLFKLGCYIQKNCGKFLVVGLLIFGAPAVGLKA
PTC    QVALDQIDKGKARGSRTAIYLRSVFQSHLETGSSVQKHAGKVLFVAILVLSTFCVGLKS
BPTC   ALALSELEKGNIEGGRTSLWIRAWLQEQLPILGCFLQGDAGKVLFVAILVLSTFCVGLKS
           **  .  **.  *  ....  .*.  .*   *   **    *  .** **  *..*....*  ****

HPTC   ANLETNVEELWVEVGGRVSRELNYTRQKIGEEAMFNPQLMIQTPKEEGANVLTTEALLQH
MPTC   ANLETNVEELWVEVGGRVSRELNYTRQKIGEEAMFNPQLMIQTPKEEGANVLTTEALLQH
PTC    AQIHSKVHQLWIQEGGRLEAELAYTQKTIGEDESATHQLLIQTTHDPNASVLHPQALLAH
BPTC   AQIHTRVDQLWVQEGGRLEAELKYTAQALGEADSSTHQLVIQTAKDPDVSLLHPGALLEH
       *....  *.**..   ***.   ** **   .**          **.***    .   ..*     ***  *

HPTC   LDSALQASRVHVYMYNRQWKLEHLCYKSGELITET-GYMDQIIEYLYPCLIITPLDCFWE
MPTC   LDSALQASRVHVYMYNRQWKLEHLCYKSGELITET-GYMDQIIEYLYPCLIITPLDCFWE
PTC    LEVLVKATAVKVHLYDTEWGLRDMCNMPSTPSFEGIYYIEQILRHLIPCSIITPLDCFWE
BPTC   LKVVHAATRVTVHMYDIEWRLKDLCYSPSIPDFEGYHHIESIIDNVIPCAIITPLDCFWE
       *          *. * * .*.     .* * ..*       ..    *   .. *.   .**  ***********

HPTC   GAKLQSGTAYLLGKPPLR----WTNFDPLEFLEELK------KINYQVDSWEEMLWKAEV
MPTC   GAKLQSGTAYLLGKPPLR----WTNFDPLEFLEELK------KINYQVDSWEEWLNKAEV
PTC    GSQLL-GPESAVVIPGLNQRLLWTTLNPASVMQYMKQKMSEEKISFDFETVEQYMKRAAI
BPTC   GSKLL-GPDYPIYVPHLKHKLQWTHLNPLEVVEEVK-KL---KFQFPLSTIEAYMKRAGI
       *..*  *       *   *  **..  *           ...*     *...    .*  ...*.

HPTC   GHGYMDRPCLNPADPDCPATAPNKNSTKPLDMALVLNGGCHGLSRKYMHWQEELIVGGTV
MPTC   GHGYMDRPCLNPADPDCPATAPNKNSTKPLDVALVLNGGCQGLSRKYMHWQEELIVGGTV
PTC    GSGYMEKPCLNPLNPCPDTAPNKNSTQPPDVGAILSGGCYGYAAKHMHWPEELIVGGRK
BPTC   TSAYMKKPCLDPTDPHCPATAPNKKSGHIPDVAAELSHGCYGFAAAYMHWPEQLIVGGAT
        .** .***.* .*.** *****.*     *..   *. **  .      *** *.*****

HPTC   KNSTGKLVSAHALQTMFQLMTPKWMYEHPKGYEYVSHINWNEDKAAAILEAWQRTYVEVV
MPTC   KNATGKLVSAHALQTMFQLMTPKQMYEHPRGYDYVSHINWNEDRAAAILEAWQRTYVEVV
PTC    RNRSCHLRKAQALQSVVQLMTEKEMYDQWQDNYKVHHLGWTQEKAAEVLNAWQRNFSREV
BPTC   RNSTSALRSARALQTVVQLMGEREMYEYWADHYKVHQIGWNEKAAAVLDAWQRKFAAEV
       .*. ..  *   *.***..  ***    ..**.         .  *   .  *  ...**   .*.****    .    *

HPTC   HQSVAQNSTQK----VLSPTTTTLDDTLKSFSDVSVIRVASGYLLMLAYACLTMLRW-DC
MPTC   HQSVAPNSTQK----VLPFTTTTLDDILKSFSDVSVIRVASGYLLMLAYACLTMLRW-DC
PTC    EQLLRKQSRIATNYDIYVFSSAALDDILAKFSHPSALSIVIGVAVTVLYAFCTLLRWRDP
BPTC   RKI-TTSGSVSSAYSFYPFSTSTLNDILGKFSEVSLKNIILGYMFMLIYVAVTLIQWRDP
         .     .         *....*.***  **. *  .       *      .*       .  *    *...*  *

HPTC   SKSQGAVGLAGVLLVALSVAAGLGLCSLIGISFNAATTQVLPFLALGVGVDDVFLLAHAF
MPTC   SKSQGAVGLAGVLLVALSVAAGLGLCSLIGISFNAATTQVLPFLALGVGVDDVFLLAHAF
PTC    VRGQSSVGVAGVLLMCFSTAAGLGLSALLGIVFNAASTQVVPFLALGLGVDHIFMLTAAY
BPTC   IRSQAGVGIAGVLLLSITVAAGLGFCALLGIPFNASSTQIVPFLALGLGVQDMFLLTHTY

HPTC   SETGQNKRIPFEDRTGECLKRTGASVALTSISNVTAFFMAALIPIPALRAFSLQAAVVVV
MPTC   SETGQNKRIPFEDRTGECLKRTGASVALTSISNVTAFFMAALIPIPALRAFSLQAAVVVV
PTC    AESN------RREQTKLILKKVGPSILFSACSTAGSFFAAAFIPVPALKVFCLQAAIVMC
BPTC   VEQAGD--VPREERTGLVLKKSGLSVLLASLCNVMAFLAAALLPIPAFRVFCLQAAILLL

HPTC   FNFAMVLLIFPAILSMDLYRREDRRLDIFCCFTSPCVSRVIQVEPQAYTDTHDNTRYSPP
MPTC   FNFAMVLLIFPAILSMDLYRPEDRRLDIFCCFTSPCVSRVIQVEPQAYTEPHSNTRYSPP
PTC    SNLAAALLVFPAMISLDLRRRTAGRADIFCCCF-PVWKEQPKVAPPVLPLNNNNGR----
BPTC   FNLGSILLVFPAMISLDLRRRSAAPADLLCCLM-P---ESP------LPKKKIPER----

HPTC   PPYSSHSFAHETQITMQSTVQLRTEYDPHTHVYYTTAEPRSEISVQPVTVTQDT LSCQSP.
MPTC   PPYTSHSFAHETHITMQSTVQLRTEYDPHTHVYYTTAEPRSEISVQPVTVTQDNLSCQSP
PTC    ------ ------------------------- GARHPKSCNNNRVPLAQNPLLEQPA
BPTC   --------------------------------- AKTRKNDKTHRID-TTRQPLDPDVS

HPTC   ESTSSTRDLLSQFSDSSLHCLEPPCTKWTLSSFAEKHYAPFLLKPKAKVVVIFLFLGLLG
MPTC   ESTSSTRDLLSQFSDSSLHCLEPPCTKWTLSSFAEKHYAPFLLKPKAKVVVILLFLGLLG
PTC    DIPGSS----------HSLASF----SLATFAFQHYTPFLMRSWVKFLTVMGFLAALI
BPTC   ENVTKT----------CCL-SV----SLTKWAKNQYAPFIMRPAVKVTSMLALIAVIL

HPTC   VSLYGTTRVRDGLDLTDIVPRETREYDFIAAQFKYFSFYNMYIVTQKA-DYPNIQHLLYD
MPTC   VSLYGTTRVRDGLDLTDIVPRETREYDFIAAQFKYFSFYNMYIVTQKA-DYPNIQHLLYD
PTC    SSLYASTRLQDGLDIIDLVPKDSNEHKFLDAQTRLFGFYSMYAVTQGNFEYPTQQQLLRD
BPTC   TSVWGATKVKDGLDLTDIVPENTDEHEFLSRQEKYFGFYNMYAVTQGNFEYPTNQKLLYE

HPTC   LHRSFSNVKYVMLEENKQLPKMWLHYPRDWLQGLQDAFDSDWETGKIMPNN-YKNGSDDG
MPTC   LHKSFSNVKYVMLEENKQLPQMWLHYPRDWLQGLQDAFDSDWETGRIMPNN-YKNGSDDG
PTC    YHDSFVRVPHVIKNDNGGLPDFWLLLFSEWLGNLQKIFDEEYRDGRLTKECWFPNASSDA
BPTC   YHDQFVRIPNIIKNDNGGLTKFWLSLFRDWLLDLQVAFDKEVASGCITQEYWCKNASDEG
```

```
                                          -continued
HPTC  VLAYKLLVQTGSRDKPIDISQLTK-QRLVDADGIINPSAFYIYLTAWVSNDPVAYAASQA
MPTC  VLAYKLLVQTGSRDKPIDISQLTK-QRLVDADGIINPSAFYIYLTAWVSNDPVAYAASQA
PTC   ILAYKLIVQTGHVDNPVDKELVLT-NRLVNSDGIINQRAFYNYLSAWATNDVFAYGASQG
BPTC  ILAYKLMVQTGHVDNPIDKSLITAGHRLVDKDGIINPKAFYNYLSAWATNDALAYGASQG HPTC  NIRPHRPEWVHDKADYMPETRLRIPAAEPIEYAQFPFYLNGLRDTSDFVEAIEKVRTICS
MPTC  NIRPHRPEWVHDKADYMPETRLRIPAAEPIEYAQFPFYLNGLRDTSDFVEAIEKVRVICN
PTC   KLYPEPRQYFHQPNEY----DLKIPKSLPLVYAQMPFYLHGLTDTSQIKTLIGHIRDLSV
BPTC  NLKPQPQRWIHSPEDV----HLEIKKSSPLIYTQLPFYLSGLSDTDSIKTLIRSVRDLCL HPTC  NYTSLGLSSYPNGYPFLFWEQYIGLPHWLLLFISVVLACTFLVCAVFLLNPWTAGIIVMV
MPTC  NYTSLGLSSYPNGYPFLFWEQYISLRHWLLLSISVVLACTFLVCAVFLLNPWTAGIIVMV
PTC   KYEGFGLFNYPSGIPFIFWEQYMTLRSSLAMILACVLLAALVLVSLLLLSVWAAVLVILS
BPTC  KYEAKGLPNFPSGIPFLFWEQYLYLRTSLLLALACALGAVFIAVMVLLLNAWAAVLVTLA HPTC  LALMTVELFGMMGLIGIKLSAVPVVILIASVGIGVEFTVHVALAFLTAIGDKNRRAVLAL
MPTC  LALMTVELFGMMGLIGIKLSAVPVVILIASVGIGVEFTVHVALAFLTAIGDKNHRAMLAL
PTC   VLASLAQIFGAMTLLGIKLSAIPAVILILSVGMMLCFNVLISLGFMTSVGNRQRRVQLSM
BPTC  LATLVLQLLGVMALLGVKLSAMPPVLLVLAIGRGVHFTVHLCLGFVTSIGCKRRRASLAL HPTC  EHMFAPVLDGAVSTLLGVLMLAGSEFDFIVRYFFAVLAILTILGVLNGLVLLPVLLSFFG
MPTC  EHMFAPVLDGAVSTLLGVLMLAGSEFDFIVRYFFAVLAILTVLGVLNGLVLLPVLLSFFG
PTC   QMSLGPLVHGMLTSGVAVFMLSTSPPEFVIPHFCWLLLVVLCVGACNSLLVFPILLSMVG
BPTC  ESVLAPVVHGALAAALAASMAL.ASEFGFVARLFLRLLLALVFLGLIDGLLFFPIVLSILO HPTC  PYPEVSPANGLNRLPTPSPEPPPSVVRFAMPPGHTHSGSDSSDSEYSSQTTVSGLSE-EL
MPTC  PCPEVSPANGLNRLPTPSPEPPPSVVRFAVPPGHTNNGSDSSDSEYSSQTTVSGISE-EL
PTC   PEAELVPLEHPDRISTPSPLPVRSSKRSGKSYVVQGSRSSRGSCQKSHHHHHKDLNDPSL
BPTC  PAAEVRPIEHPERLSTPSPKCSPIHPRKSSSSSGGGDKSSRTS--KSAPRPC----APSL HPTC  RHYEAQQGAGGPAHQVIVEATENPVFAHSTVVHPESRHHPPSNPRQQPHLDSGSLPPGRQ
MPTC  RQYEAQQGAGGPAHQVIVEATENPVFARSTVVHPDSPHQPPLTPRQQPHLDSGSLSPGRQ
PTC   TTITEEPQSWKSSNSSIQMPNDWTYQPREQ--RPASYAAPPPAYHKAAAQQHHQHQGPPT
BPTC  TTITEEPSSWHSSAHSVQSSMQSIVVQPEVVVETTTYNGSDSASGRSTPTKSSHGGAITT HPTC  GQQPRRDPPREGLWPPLYRPRRDAFEISTEGHSGPSNRARWGPRGARSHNPPNPASTAMG
MPTC  GQQPRRDPPREGLRPPPYRPRRDAFEISTEGHSGPSNRDRSGPRGARSHNPRNPTSTAMG
PTC   TPPPPFPTA-----------------YPPELQSIVVQPEVTVETTHS-----------DS
BPTC  TKVTATANIKVEVVTPSDRKSRRSYHYYDRRRDRDEDRDRDRERDRDRDRDRDRDRDRDR HPTC  SSVPGYCQPITTVTASASVTVAVHPPPVPGPGRNPRGGLCPGY---PETDHGLFEDPHVP
MPTC  SSVPSYCQPITTVTASASVTVAVHPP--PGPGRNPRGGPCPGYESYPETDHGVFEDPHVP
PTC   NT--------TKVTATANIKVELAMP-----GPAVRS---YNFTS---------------
BPTC  DR--------DRERSRERDRP.DRYRD-----EPDHPA---SPRENGRDSGHE-------

HPTC  FHVRCERRDSKVEVIELQDVECEERPRGSSSN
MPTC  FHVRCERRDSKVEVIELQDVECEERPWGSSSN
PTC   --------------------------------
BPTC  ------------------------ SDDSSRH
```

The identity of ten other clones recovered from the mouse library is not determined. These cDNAs cross-hybridize with mouse ptc sequence, while differing as to their restriction maps. These genes encode a family of proteins related to the patched protein. Alignment of the human and mouse nucleotide sequences, which includes coding and noncoding sequence, reveals 89% identity.

Radiation hybrid mapping of the human ptc gene. Oligonucleotide primers and conditions for specifically amplifying a portion of the human ptc gene from genomic DNA by the polymerase chain reaction were developed. This marker was designated STS SHGC-8725. It generates an amplification product of 196 bp, which is observed by agarose gel electrophoresis when o human DNA is used as a template, but not when rodent DNA is used. Samples were scored in duplicate for the presence or absence of the 196 by product in 83 radiation hybrid DNA samples from the Stanford G3 Radiation Hybrid Panel (purchased from Research Genetics, Inc.) By comparison of the pattern of G3 panel scores for those with a series of Genethon meiotic linkage 5 markers, it was determined that the human ptc gene had a two point lod score of 1,000 with the meiotic marker D9S287, based on no radiation breaks being observed between the gene and the marker in 83 hybrid cell lines. These results indicate that the ptc gene lies within 50-100 kb of the marker. Subsequent physical mapping in YAC and BAC clones confirmed this close linkage estimate. Detailed map information can be obtained from http://www.shgc.stanford.edu.

Analysis of BCNS mutations. The basal cell nevus syndrome has been mapped to the same region of chromosome 9q as was found for ptc. An initial screen of EcoRI digested DNA from probands of 84 BCNS kindreds did not reveal major rearrangements of the ptc gene, and so screening was performed for more subtle sequence abnormalities. Using vectorette PCR, by the method according to Riley et al. (1990) *N.A.R.* 18:2887-2890, on a BAC that contains genomic DNA for the entire coding region of ptc, the intronic sequence flanking 20 of the 24 exons was determined. Single strand conformational polymorphism analysis of PCR-amplified DNA from normal individuals, BCNS o patients and sporadic basal cell carcinomas (BCC) was performed for 20 exons of ptc coding sequence. The amplified samples giving abnormal bands on SSCP were then sequenced.

In blood cell DNA from BCNS individuals, four independent sequence changes were found; two in exon 15 and two in exon 1 0. One 49 year old man was found to have a sequence change in exon 15. His affected sister and daughter have the same alteration, but three unafflicted relatives do not. His blood cell DNA has an insertion of 9 base pairs at nucleotide 2445 of the coding sequence, resulting in the insertion of three amino acids (PNI) after amino acid 815. Because the normal sequence preceding the insertion is also PNI, a direct repeat has been formed.

The second case of an exon 15 change is an 18 year old woman who developed jaw cysts at age 9 and BCCs at age 6. The developmental effects together with the BCCs indicate that she has BCNS, although none of her relatives are known to have the syndrome. Her blood cell DNA has a deletion of 11 bp, removing the sequence ATATCCAGCAC (SEQ ID NO: 20) at nucleotides 2441 to 2452 of the coding sequence. In addition, nucleotide 2452 is changed from a T to an A. The deletion results in a frameshift that is predicted to truncate the protein after amino acid 813 with the addition of 9 amino acids. The predicted mutant protein is truncated after the seventh transmembrane domain. In *Drosophila*, a ptc protein that is truncated after the sixth transmembrane domain is inactive when ectopically expressed, in contrast to the full-length protein, suggesting that the human protein is inactivated by the exon 15 sequence change. The patient with this mutation is the first affected family member, since her parents, age 48 and 50, have neither BCCs nor other signs of the BCNS. DNA from both parents' genes have the normal nucleotide sequence for exon 15, indicating that the alteration in exon 15 arose in the same generation as did the BCNS phenotype. Hence her disease is the result of a new mutation. This sequence change is not detected in 84 control chromosomes.

Analysis of sporadic basal cell carcinomas. To determine whether ptc is also involved in BCCs that are not associated with the BCNS or germline changes, DNA was examined from 12 sporadic BCCS. Three alterations were found in these tumors. In one tumor, a C to T transition in exon 3 at nucleotide 523 of the coding sequence changes a highly conserved leucine to phenylalanine at residue 175 in the first putative extracellular loop domain Blood cell DNA from the same individual does not have the alteration, suggesting that it arose somatically in the tumor. SSCP was used to examine exon 3 DNA from 60 individuals who do not have BCNS, and found no changes from the normal sequence. Two other sporadic BCCs have deletions o encompassing exon 9 but not extending to exon 8.

The existence of sporadic and hereditary forms of BCCs is reminiscent of the characteristics of the two forms of retinoblastoma. This parallel, and the frequent deletion in tumors of the copy of chromosome 9q predicted by linkage to carry the wild-type allele, demonstrates that the human ptc is a tumor suppressor gene. ptc represses a variety of genes, including growth factors, during *Drosophila* development and may have the same effect in human skin. The often reported large body size of BCNS patients also could be due to reduced ptc function, perhaps due to loss of control of growth factors. The C to T transition identified in ptc in the sporadic BCC is also a common genetic change in the p53 gene in BCC and is consistent with the role of sunlight in causing these tumors. By contrast, the inherited deletion and insertion mutations identified in BCNS patients, as expected, are not those characteristic of ultraviolet mutagenesis.

The identification of the ptc mutations as a cause of BCNS links a large body of developmental genetic information to this important human disease. In embryos lacking ptc function part of each body segment is transformed into an anterior-posterior mirror-image duplication of another part. The patterning changes in ptc mutants are due in part to derepression of another segment polarity gene, wingless, a homolog of the vertebrate Wnt genes that encodes secreted signaling proteins. In normal embryonic development, ptc repression of wg is relieved by the Hh signaling protein, which emanates from adjacent cells in the posterior part of each segment. The resulting localized wg expression in each segment primordium organizes the pattern of bristles on the surface of the animal. The ptc gene inactivates its own transcription, while Hh signaling induces ptc transcription.

In flies two other proteins work together with Hh to activate target genes: the ser/thr kinase fused and the zinc finger protein encoded by cubitus interruptus. Negative regulators working together with ptc to repress targets are protein kinase A and costal2. Thus, mutations that inactivate human versions of protein kinase A or costal2, or that cause excessive activity of human hh, gli, or a fused homolog, may modify the BCNS phenotype and be important in tumorigenesis.

In accordance with the subject invention, mammalian patched genes, including the mouse and human genes, are provided, which can serve many purposes. Mutations in the gene are found in patients with basal cell nevus syndrome, and in sporadic basal cell carcinomas. The autosomal dominant inheritance of BCNS indicates that patched is a tumor suppressor gene. The patched protein may be used in a screening for agonists and antagonists, and for assaying for the transcription of ptc mRNA. The protein or fragments thereof may be used to produce antibodies specific for the protein or specific epitopes of the protein. In addition, the gene may be employed for investigating embryonic development, by screening fetal tissue, preparing transgenic animals to serve as models, and the like.

As described above, patients with basal cell nevus syndrome have a high incidence of multiple basal cell carcinomas, medulloblastomas, and meningiomas. Because somatic ptc mutations have been found in sporadic basal cell carcinomas, we have screened for ptc mutations in several types of sporadic extracutaneous tumors. We found that 2 of 14 sporadic medulloblastomas bear somatic nonsense mutations in one copy of the gene and also deletion of the other copy. In addition, we identified mis-sense mutations in ptc in two of seven breast carcinomas, one of nine meningiomas, and one colon cancer cell line. No ptc gene mutations were detected in 10 primary colon carcinomas and eighteen bladder carcinomas.

BCNS[3] (OMIM #109400) is a rare autosomal dominant disease with diverse phenotypic abnormalities, both tumorous (BCCs, medulloblastomas, and meningiomas) and developmental (misshapen ribs, spina bifida occults, and skull abnormalities; Gorlin, R. J. (1987) *Medicine* 66:98-113). The BCNS gene was mapped to chromosome 9q22.3 by linkage analysis of BCNS families and by LOH analysis in sporadic BCCs (Gallani, M. R. et al. (1992) *Cell* 69:111-117). LOH in sporadic medulloblastomas has been reported in the same chromosome region (Schofield, D. et al. (1995) *Am J Pathol* 146:472-480). Recently, the human homologue of the *Drosophila* patched (PTCII) gene has been mapped to the BCNS region (Hahn, H. et al. (1996) *Cell* 85:841-851; Johnson, R. L. et al. (1996) *Science* 272:1668-1671; Gallani, M. R. et al. (1996) *Nat Genet* 14:78-81; Xie, J. et al. (1997) *Genes Chromosomes Cancer* 18:305-309), and mutations in this gene have been found in the blood DNA of BCNS patients and in the DNA of sporadic BCCs (Hahn, H. et al., supra; Johnson, R. L. et al., supra; Gallani, M. R. et al., supra; and Chidambaram, A. et al. (1996) *Cancer Res* 36:4599-4601). ptc appears to function as a tumor suppressor gene; inactivation abrogates its normal inhibition of the hedgehog signaling pathway. Because of the wide variety of tumors in patents with the BCNS and wide tissue distribution of ptc gene expression, we have begun screening for ptc gene mutations in several types of human cancers, especially those present in increased numbers in BCNS patients (medulloblastomas), those in tissues derived embryologically from epidermis (breast carcinomas) and those with chromosome 9q LOG (bladder carcinomas; see Cairns, P. et al. (1993) *Cancer Res* 53:1230-1232; and Sidransky, D. et al. (1997) *NEJM* 326: 737-740).

Figure 3A:
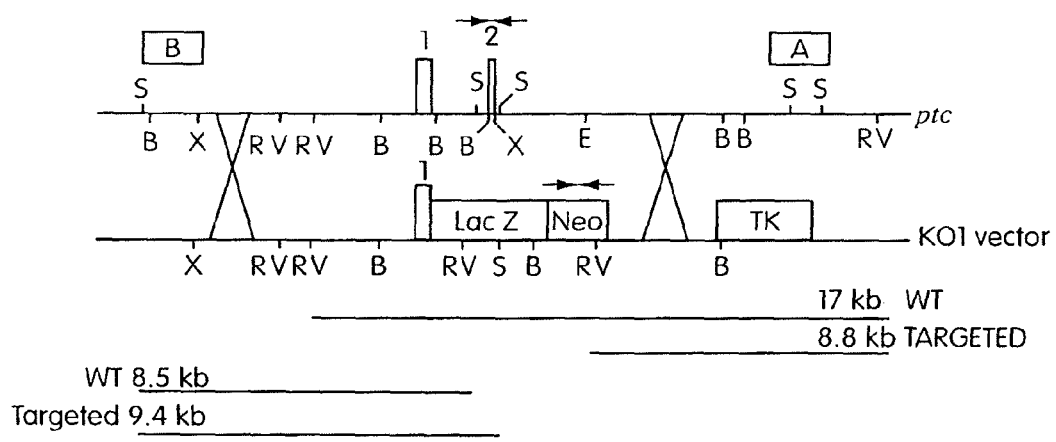
FIG. 3 (panels A-B) illustrates the generation of ptc mutations. (A) The ptc mutant allele was generated by homologous recombination between the KO1 targeting vector and ptc. External probe A detected a 3' EcoRV polymorphism on blots and probe B detected a 5' SacI polymorphism. Exons are numbered. (B) Transmission of the ptc$^{KO1}$ allele through the germline was confirmed by Southern blot (upper panel) and a PCR genotyping assay (lower panel). PCR primers are indicated as arrows in A. Because the homozygous mutant embryos were being resorbed, there was much less yolk sac DNA in the −/− lanes.
Figure 3B:
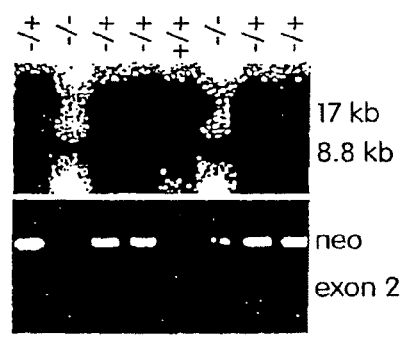
Figure 4A:
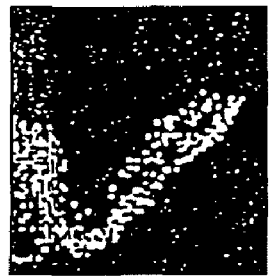
FIG. 4 (panels A-G) illustrate the germ layer-specific derepression of Hh target genes in ptc$^{-/-}$ embryos. (A, B) Lateral views of E8.25 wild-type (A) and ptc$^{-/-}$ (B) embryos. The headfolds are overgrown in the mutant (white arrows) and the heart is not properly formed (red arrows). (C) Lateral views of E8.75 ptc$^{+/-}$ (left) and ptc$^{-/-}$ (right) embryos stained with X-gal (28) (D, E, F, G) Transverse sections through E8.75 ptc$^{+/-}$ (D, F) and ptc$^{-/-}$ (E, G) embryos stained with X-gal (D, E) or hybridized with a digoxigenin labeled Gli probe (29) (F, G). Both lacZ and Gli were derepressed in the ectoderm and mesoderm but not in the endoderm (arrows). In A and B, anterior is to the left and dorsal is up. In C, anterior is up and dorsal is to the right. In D to G, dorsal is up.
Figure 4B:
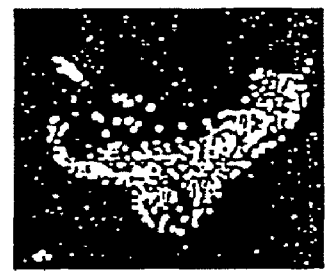
Figure 4C:
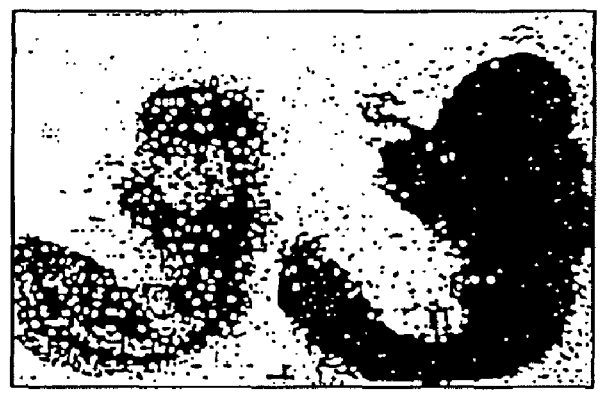
Figure 4D:
Figure 4E:
Figure 4F:
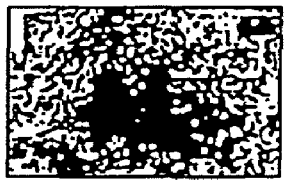
Figure 4G:
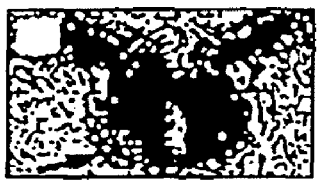

To further study the roles of ptc in development and in tumorigenesis, we have constructed mice lacking ptc function. By homologous recombination, part of ptc exon 1 (including the putative start codon) and all of exon 2 were replaced with lacZ and a neomycin resistance gene (FIG. 3) (DNA from the ptc genomic locus was isolated from a 129SV genomic phage library [Stratagene]. Exons 1-15 of human PTC (1) were mapped by PCR and sequencing. The 3' arm of homology was a 3.5 kb EcoRI-BamHI fragment from the second intron that gained a BamHI site from pBSII [Stratagene] and was cloned into the BamHI site of pPNT [Tybulewicz, et al. (1991) *Cell* 65:1153]. A cassette containing the gene for nuclear localized b-galactosidase, followed by the mPl intron and polyA tail was excised from pNLacF [Mercer, et al. (1991) *Neuron* 7:703] and cloned into the Xho I site of pPNT using Xho I and Sal I linkers. The 5' arm of homology was a 6.5 kb Xho I to Nru I fragment that was cloned into the Xho I site upstream of lacZ via a Sal I linker The Nru I site is in the first ptc exon. The resulting plasmid, KO1, was linearized with Xho I and electroporated into RI ES cells that were subjected to double selection and analyzed by Southern blot [Joyner, A. L. *Gene Targeting: A Practical Approach*. Oxford University Press, New York, 1993, pp. 33-61]. Targeted clones were expanded and used for injection into C57Bl/6 blastocysts [Hogan, B. et al. *Manipulating the Mouse Embryo: A Laboratory Manual* Cold Spring Harbor Laboratory Press, Cold Spring Harbor, 1994, pp. 196-204]. Protein made from any alternative ATG would lack the first proposed transmembrane domain, flipping the orientation of the protein in the membrane. Three independent ES clones were used to make chimeras that were bred to B6D2F1 animals to generate heterozygous mice on a mixed background. Interbreeding of heterozygotes produced no homozygous animals among 202 offspring examined. Analysis of embryos from timed matings suggested that $ptc^{-/-}$ embryos die between embryonic day (E) 9.0 and E10.5, with the first gross phenotypes appearing by E8. In $ptc^{-/-}$ embryos, the neural tube failed to close completely and was overgrown in the head folds, hindbrain and spinal cord (FIG. 4, A to C). Embryonic lethality may have been due to abnormal development of the heart (FIG. 4B), which never beats.

In flies Ptc protein inhibits ptc transcription. By inhibiting Ptc function, Hh increases production of Ptc which may then bind available Hh and limit the range or duration of effective Hh signal (Y. Chen and G. Struhl, (1996) *Cell* 87:553). Hh signaling also post-transcriptionally regulates the zinc finger protein cubitus interruptus (ci) (C. K. Motzny and R. Holmgren, (1996) *Mech Dev* 52:137; Dominguez, et al. (1996) *Science* 272:1621; Hepker, et al. (1997) *Development* 124:549; Aza-Blanc, et al., (1997) *Cell* 89:1043). In vertebrates, Sonic hedgehog (Shh) signaling induces transcription of both ptc and a ci homolog, Gli (Goodrich, et al. (1996) *Genes Devel.* 10:301; Marigo, et al. (1996) *Development* 122:1225; Concordet, et al., (1996) *Development* 122:2835; Marigo, et al. (1996) *Dev. Biol.* 180:273). Derepression of ptc and Gli in $ptc^{-/-}$ mice should therefore reveal where Ptc is normally active.

ptc and Gli expression was greatly increased in $ptc^{-/-}$ embryos. In $ptc^{+/-}$ mice expression of the lacZ gene fused to the first ptc exon during targeting accurately reported the pattern of ptc transcription (FIGS. 4, C and D). In $ptc^{-/-}$ embryos expression of ptc-lacZ was extensively derepressed starting at about E8.0 in the anterior neural tube and spreading posteriorly by E8.75 (FIGS. 4, C and E). Derepression was germ layer-specific: both ptc-lacZ and Gli were expressed throughout the ectoderm and mesoderm, but not in the endoderm (FIG. 4, D to G). ptc expression may be excluded from the endoderm in order to avoid interfering with Shh signaling from the endoderm to the mesoderm (Roberts et al., (1995) *Development* 121:3163). A differential requirement for Ptc may distinguish the germ layers.

As revealed by ptc mutants, an early site of Ptc activity is the neural tube, where Shh and Ptc act antagonistically to determine cell fates. Shh induces the floor plate and motor neurons in the ventral neural tube (Echelard et al., (1993) *Cell* 75:1417; Roelink et al., (1994) *Cell* 76:761; Roelink et al., (1995) *Cell* 81:445-455). These cell types fail to form in Shh mutants (Chiang et al., (1996) *Nature* 383:407). High levels of Shh produced by the notochord may induce floor plate by completely inactivating Ptc (Echelard et al., (1993) supra; Roelink et al, (1994) supra; Roelink et al., (1995) supra). If so, elimination of ptc function might cause floor plate differentiation throughout the neural tube. Prospective floor plate cells transcribe the forkhead transcription factor HNF3b first and then Shh itself (Echelard et al., (1993) supra; Roelink et al., (1994) supra; Roelink et al., (1995) supra). In E8.5 ptc mutants, transcription of HNF3b and Shh was expanded dorsally (FIG. 5, A to C). Ectopic Shh expression was most extensive in the anterior, where transcripts could be detected throughout the neurepithelium (FIGS. 5, B and C). Cells in this region were in a single layer with basal nuclei, like floor plate cells that are normally restricted to the ventral midline (FIGS. 5, D and E). Expression of the intermediate neural tube marker Pax6 (C. Walther and P. Gruss, (1991) *Development* 113:1435) was completely absent from ptc mutant embryos, suggesting that only ventral, and not ventrolateral, cell fates are specified (FIGS. 5, F and G).

Figure 5A:
FIG. 5 (panels A-N) illustrate ventralization of the neural tube in ptc$^{-/-}$ embryos. (A) Lateral view of E8.5 wild-type (left) and ptc$^{-/-}$ (right) embryos hybridized with a HNF3b probe. Expression is expanded dorsally in the mutant. (B, C) Transverse sections through the hindbrain of E8.5 wild-type (B) and ptc$^{-/-}$ (C) embryos hybridized with $^{35}$S-labeled Shh probe (8). Shh is expressed in the floor plate (fp) and notochord (nc) of the wild-type embryo, and is greatly expanded in the ptc mutant. g=gut (D, E) Hematoxylin and eosin stained transverse sections through the hindbrain of wild-type (D) and ptc$^{-/-}$ (E) E8.5 embryos. Bottle-shaped cells with basal nuclei are indicated by arrows. (F, G) Transverse sections through E8.5 ptc$^{+/-}$ (F) and ptc$^{-/-}$ (G) embryos hybridized with Pax6 probe show loss of expression from the ptc mutant. (H) Dorsal view of E8.25-E8.5 embryos hybridized with Pax3 probe. Because of the kinking in the neural tube, the ptc$^{-/-}$ embryo is curled on itself. Weak Pax3 expression is seen in the posterior dorsal neural tube of the ptc$^{-/-}$ embryo (bottom, arrow). (I, J) Transverse sections through E8.5 wild-type (I) and ptc$^{-/-}$ (J) embryos hybridized with Pax3 probe. Pax3 is expressed in the dorsal neural tube (nt) and dermamyotome (dm) in the wild-type, but is only present in a small dorsal domain of the mutant neural tube. s=somite (K, L) Lateral views of E9 wild type (K) and E8.5 ptc (L) embryos hybridized with erb-b3 probe. Staining is seen in migrating neural crest in the head and somites of wild type but not mutant embryos (red arrows). Weak staining in the head, heart and gut (black arrows) is background or non-neural crest related. (M) Lateral view of wild type (top) and ptc$^{-/-}$ (bottom) embryos hybridized with Nkx2.1 probe. The body of the mutant is twisted. Nkx2.1 expression is limited to the anterior, but is expanded dorsally in the mutant. (N) Lateral view of E8.5 ptc$^{+/-}$ (left) and ptc$^{-/-}$ (right) embryos hybridized with hoxbl probe. Loss of expression in rhombomere four is indicated by the asterisks. In all transverse sections, dorsal is up. In A, K, L and N, anterior is up and dorsal is to the right. In H and M, anterior is to the left.
Figure 5B:
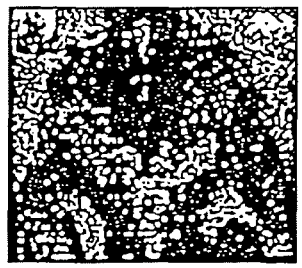
Figure 5C:
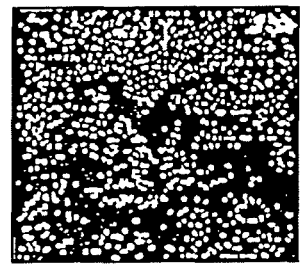
Figure 5D:
Figure 5F:
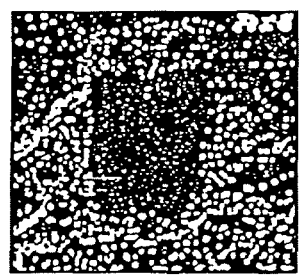
Figure 5G:
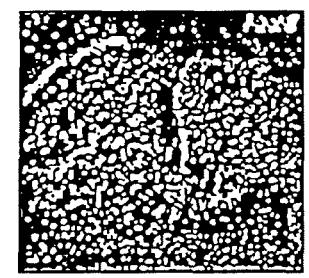
Figure 5E:
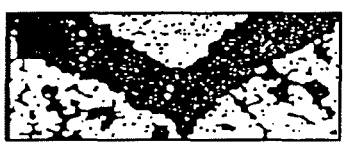
Figure 5H:
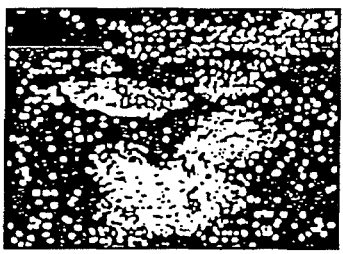
Figure 5I:
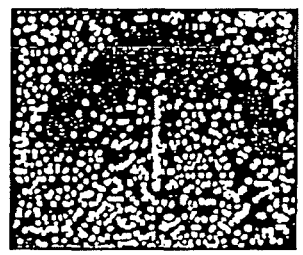
Figure 5J:
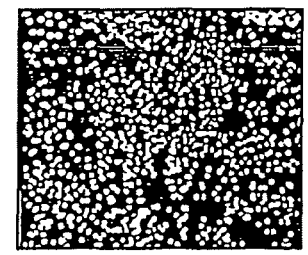
Figure 5K:
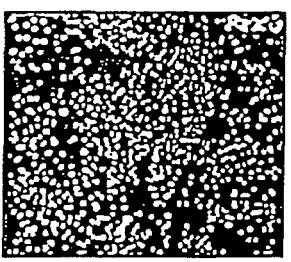
Figure 5L:
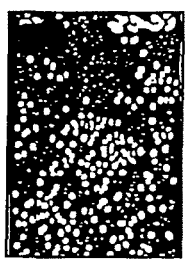
Figure 5M:
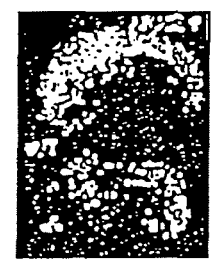
Figure 5N:
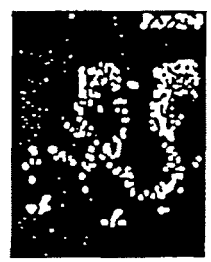

Dorsalizing signals from the surface ectoderm (Dickinson, et al. (1995) *Development* 121:2099; Liem, et al. (1995) *Cell* 82:969) could confer dorsal cell fates even in the absence of ptc function. In E8-E9 ptc homozygotes the dorsal neural tube marker Pax3 was not expressed in the anterior neural tube, but was transcribed in a very small region at the dorsal-most edge of the posterior neural tube (FIG. 5, H to J). In addition erb-b3 transcription, which marks migratory neural crest cells (FIG. 5K) (H. U. Wang and D. J. Anderson, (1997) *Neuron* 18:383), was not detected in the somites of ptc mutants (FIG. 5L). We conclude that only limited dorsal fate determination occurs in the absence of ptc. BMP signals maintain dorsal gene expression (Dickinson, et al. (1995) supra; Liem, et al. (1995) supra), so either ptc is required for BMPs to work or BMP signaling is ineffective in most cells expressing Shh targets.

Ventralization of the neural tube in ptc mutants occurred without affecting cell identity along the rostrocaudal axis. In $ptc^{-/-}$ embryos, cells in the anterior neural tube expressed the forebrain marker Nkx2.1 (Shimamura, et al. (1995) *Development* 121:3923) and cells in the spinal cord transcribed low levels of hoxbl (Wilkinson, et al. (1989) *Nature* 341:405) (FIGS. 5, M and N). hoxbl was not transcribed in the fourth rhombomere of ptc mutants (FIG. 5, N). This may reflect a transformation of hindbrain cells to floor plate, since hoxbl is excluded from the midline of wild-type embryos. Conversely, in the anterior, Nkx2.1 expression was expanded dorsally in mutants compared to wild-type embryos (FIG. 5, M).

Figure 6A:
FIG. 6 (panels A-F) depict keletal abnormalities and medulloblastomas in ptc$^{+/-}$ mice (A) Alcian blue and Alizarin red stained hindlimb from a ptc$^{+/-}$ mouse (30). The preaxial digit is duplicated (arrows). (B, C) Dorsal views of brains from wild-type (B) and ptc$^{+/-}$ (C) mice. Anterior is up. In the posterior wild-type brain, the colliculi (col) are present as distinct bumps between the cortex (cor) and cerebellum (ce). In the ptc$^{+/-}$ mouse, a massive medulloblastoma (mb, outlined in red) grew over the colliculi and normal cerebellum, which can no longer be seen. The olfactory bulbs were removed. (D, E) Hematoxylin and eosin stained section through human (D) and mouse (E) medulloblastomas. The tumor cells are small with dark, carrot-shaped nuclei (arrows) and form nodules with no apparent orientation. (F) Synaptophysin immunoreactivity in a mouse medulloblastoma (26). Synaptophysin staining (brown) is seen in some processes (arrows). Nuclei are purple.
Figure 6B:
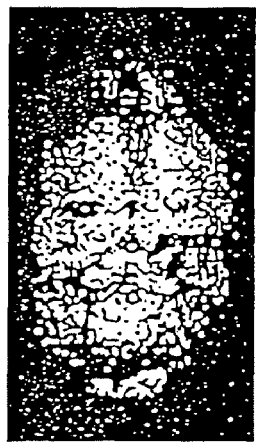
Figure 6C:
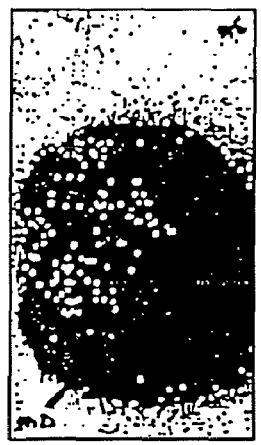
Figure 6D:
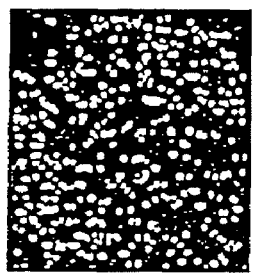
Figure 6E:
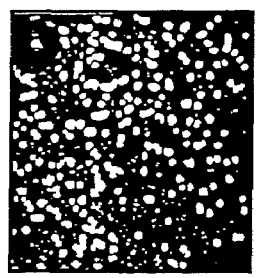
Figure 6F:
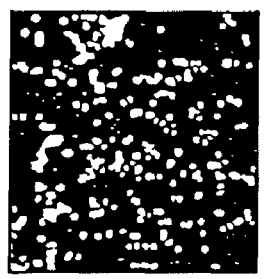

$Ptc^{+/-}$ mice had phenotypes similar to those of BCNS patients: they were larger than their wild-type littermates [30.72±3.83 (average±SD; n=29) vs. 26.54±2.51 (n=39) at 2-3 months; P=0.000001], a small fraction (3 of 389 mice examined) had hindlimb defects such as extra digits or syndactyly (FIG. 6A) or obvious soft tissue tumors (1 of 243) and many developed brain tumors (see below).

Of 243 ptc$^{+/-}$ mice which were between the ages of 2 and 9 months and were not sacrificed for other studies, 18 died or were euthanized because of sickness. No wild-type littermates died. Ten of the affected heterozygotes were autopsied and eight were found to have large growths in the cerebellum that resembled medulloblastomas (FIGS. 6, B and C). Human medulloblastomas are believed to arise from a "primitive neurectodermal" cell type (J. P. Provias and L. E. Becker, (1996) *J Neurooncol* 29:35). They are most common in children, can be metastatic or non-metastatic, and can have glial and neuronal properties. The histology of tumors from ptc$^{+/-}$ mice was similar to that of human medulloblastoma: tumor cells were small, with dark carrot-shaped nuclei and little cytoplasm (FIGS. 6, D and E), and although a subset expressed neurofilament protein and synaptophysin (FIG. 6F) (For immunostaining, two tumors were fixed and embedded in paraffin. Tissue sections (4 mm) were cleared and dehydrated, treated with 3% hydrogen peroxide and then with a dilution of 1:10 normal rabbit serum (Vector Laboratories). Anti-synaptophysin (Boehringer-Mannheim) was used at a dilution of 1:5 and anti-neurofilament protein (Dako) at 1:50. Antibody binding was visualized with a peroxidase Vectastain Elite ABC kit (Vector Laboratories). Nuclei were counterstained with hematoxylin. Like anti-synaptophysin, anti-neurofilament staining appeared in processes of the tumor cells.), the majority of cells appeared undifferentiated. Of the two autopsied animals without apparent medulloblastomas, one had a large tumor growing out of its rib muscle and the other died for unknown reasons. Medulloblastomas and soft tissue tumors were also observed in ptc$^{+/-}$ mice maintained on an inbred 129SV background: 6 of 27 had obvious medulloblastomas; 2 of 27 had tumors in the muscle of their leg; and 3 of 27 died but were not examined.

The ptc and Gli genes were strongly transcribed in the brain tumors but not in surrounding tissue (FIGS. 7, A and B; n=3 of 3 tumors examined). There was no detectable increase in Shh expression (FIG. 7C). To assess the incidence of medulloblastomas, brains from 47 asymptomatic ptc$^{+/-}$ mice were randomly collected and stained with X-gal. Nine brains contained medulloblastomas that were easily recognized by their disorganized morphology and intense ptc-lacZ expression (FIG. 7D). Medulloblastomas were observed in 7 of 23 (30.4%) ptc$^{+/-}$ mice at 12 to 25 weeks of age, 1 of 12 (8.3%) mice at 9 to 10 weeks and 1 of 12 (8.3%) mice at 5 weeks. Tumors can therefore arise as early as 5 weeks postnatally, but they increase in severity and frequency as the animal ages.

Figure 7A:
FIG. 7 (panels A-G) illustrate derepression of ptc and Gli expression in medulloblastomas from ptc$^{+/-}$ mice. (A to C) Semi-adjacent sections through a tumor in the cerebellum of a ptc$^{+/-}$ mouse hybridized with $^{35}$S labeled probes to ptc (A), Gli (B) and Shh (C). ptc and Gli transcripts are abundant in the tumors (asterisks) compared to nearby cerebellar tissue (arrows). No Shh was detected in the tumor. (D) ptc$^{+/-}$ cerebellum (ce) and tumor (mb) stained with X-gal (28). Anterior is to the left. Derepression of ptc expression in the medulloblastoma is reflected in the high level of X-gal staining. (E) Surface staining in (arrows) regions of ptc$^{+/-}$ cerebellum contrast with absence of b-galactosidase activity in most folia (asterisk). (F) Sagittal section through cerebellum in E. X-gal staining nuclei (arrow) accumulated superficial to the molecular layer (ml), where stained nuclei are not normally seen. In unaffected regions of the cerebellum, X-gal staining was seen in scattered cells of the molecular layer (ml), strongly in the Purkinje cell layer (pcl) and weakly in the granule cell layer (gl). (G) ptc expression was examined in total RNA (15 mg) from wild-type (WT) and ptc$^{+/-}$ (+/−) cerebellums using a probe (M2-2) (6) that detects exons downstream of the lacZ and neo insertions. Actin mRNA was used as an RNA loading control. The ptc$^{+/-}$ mice had ~50% decrease in ptc transcripts.
Figure 7B:
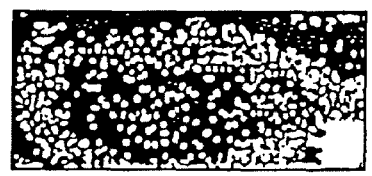
Figure 7C:
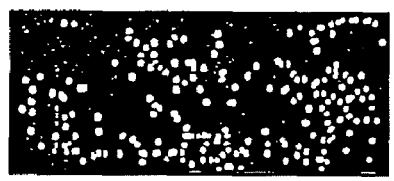
Figure 7D:
Figure 7E:
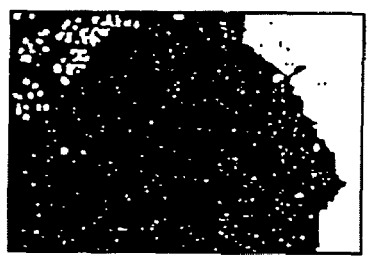
Figure 7F:

We looked for changes in ptc-lacZ expression that might reflect early stages of tumorigenesis. At all stages examined, about half of the animals [50% at 5 to 10 weeks (n=24), 56.5% at 12 to 25 weeks (n=23)] exhibited regions of increased X-gal staining on the surface of the cerebellum (FIG. 7E). These regions were usually lateral and often extended down into the fissures separating the folia (FIGS. 7, E and F). The mouse medulloblastomas may arise from these cells, which are superficial to the molecular layer of the cerebellum (FIG. 7F). During fetal development, prospective cerebellar granule cells proliferate in the external granule layer (EGL), the outermost layer of the cerebellum. Granule cells then leave and migrate past the Purkinje cells to form the internal granule cell layer of the adult animal, gradually depleting the EGL. The remnants of the fetal EGL have been proposed to be a source of human medulloblastoma progenitors, a hypothesis consistent with the higher frequency of these tumors in children (L. Stevenson and F. Echlin, (1934) *Arch. Neurol. Psychiat.* 31:93; Kadin, et al. (1970) *J Neuropathol Exp Neurol* 29:583).

Figure 7G:
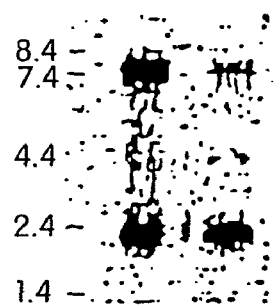

The abundance of cerebellar ptc transcripts was reduced by about 50% in the ptc$^{+/-}$ mice compared to wild-type littermates (FIG. 7G). This reduction could lead to ectopic expression of Shh target genes and to uncontrolled cell proliferation. Brain tumors might arise from Ptc haploinsufficiency alone, from additional mutations in the second ptc allele, or from a combination of ptc mutations with mutations in other tumor suppressor loci. We have not observed BCCs in ptc$^{+/-}$ mice, perhaps because somatic inactivation of the second ptc gene is required as it is in human BCCs.

Our analysis has revealed that Ptc controls growth and pattern formation in early neural development and in the adult cerebellum. Autoregulation of ptc occurs in vertebrates as it does in flies, and the balance between Hh and Ptc activities appears critical for normal development. The importance of Ptc dosage is emphasized by the phenotype of the ptc$^{+/-}$ mice, which develop a tumor type observed in the corresponding human cancer predisposition syndrome. Medulloblastoma is a common childhood brain tumor and the prognosis remains grim. The Hh/Ptc pathway may provide new diagnostic tools and new insights into tumorigenesis that may be directed toward potential therapies.

Materials and Methods

Clinical Materials. Diagnoses of all tumors were confirmed histologically. Cell lines were obtained from the America Type Culture Collection. DNA was extracted from tumors or matched normal tissue (peripheral blood leukocytes or skin) as described (Cogen, P. H. et al. (1990) *Genomics* 8:279-285; and Sambrook, J. et al. *Molecular Cloning: A Laboratory Manual*, Ed. 2, Vol. 2, pp. 9.17-9.19, Cold Spring Harbor, N.Y. (1989)).

PCR and Heteroduplex Analysis. PCR amplification and heteroduplex/SSCP analysis were performed as described (Johnson, R. L. et al., supra; Spritz, R. A. et al. (1992) *Am J Hum Genet* 51:1058-1065). Primers used and intron/exon boundary sequences of the ptc gene were derived as reported previously (Johnson, R. L. et al. supra) and are shown in Table 1. Primers for exon 1 and 2 were from Hahn et al. (supra).

Sequence Analysis. Exon segments exhibiting bands were reamplified and were sequenced directly using the Sequenase sequencing kit according to the protocol recommended by the manufacturer (United States Biochemical Corp.). A second sequencing was performed using independently amplified PCR products to confirm the sequence change. The amplified PCR products from each tumor were also cloned into the plasmid vector pCR 2.1 (InVitrogen), followed by sequence analysis of at least four independent clones. The sequence alteration was confirmed from at least two independent clones. Simplified amplification of specific allele analysis was performed according to Lei and Hall (Lei, X. and Hall, B. G. (1994) *Biotechniques* 16:44-45).

Allele Loss Analysis. Microsatellites used for allelic loss analysis were D9S109, DpS119, D9S127, and D9S287 described in the CHLC human screening set (Research Genetics). A part of the ptc intron I sequence was tested for polymorphism in a control population and found to be polymorphic in 80% of the samples tested. This micro satellite was used for analysis of ptc gene allelic loss in bladder carcinomas. The primer sequences are as follows: forward primer, 5'-CTGAGCAGATTTCCCAGGTC-3' (SEQ ID NO: 21); and reverse primer, 5'-CCTCAGACAGACCTTTCCTC-3' (SEQ ID NO: 22). The PCR cycling for this newly isolated marker was 4 min at 95° C., followed by 30 cycles of 40 s at 95° C., 2 min at 60° C., and 1 min at 72° C. PCR products were separated on 6% polyacrylamide gels and exposed to film.

Results and Discussion

Intronic boundaries were determined for 22 exons of ptc by sequencing vectorette PCR products derived from BAC 192J22 (Johnson R. L., supra; Table 1). Our findings are in agreement with those of Hahn et al. (supra), expect that we find exon 12 is composed of 2 separate exons of 126 and 119 nucleotides. This indicates that ptc is composed of 23 coding exons instead of 22. In addition, we find that exons 3, 4, 10, 11, 17, 21, and 23 differ slightly in size than reported previously (Hahn et al., supra). Of 63 tumors studied, 14 were sporadic medulloblastomas, and 9 were sporadic meningiomas. These 23 tumors were examined for allelic deletions by genotyping of tumor and blood DNA with microsatellite markers that flank the ptc gene: D9S119, D9S196, D9S287, D9S127, and D9S109. Four of 14 medulloblastomas had LOH. Two of the medulloblastomas, both of which had LOH, had mutations (med34 and med36; see Cogen, P. H. et al., supra), which are predicted to result in truncated proteins (Table 2). DNA samples from the blood of these patients lack these mutations, indicating that they both are somatic mutations. med34 also has allelic loss on 17p (Cogen, P. H. et al., supra). We were unable to detect ptc gene mutations by heteroduplex analysis in the other two medulloblastomas bearing LOH on 9q. The pathological features of these two tumors differed in that med34 belongs to the desmoplastic subtype, whereas med36 is of the classic type, indicating that ptc mutations in medulloblastomas are not restricted to a specific subtype.

TABLE 1

Primers and boundary sequences of PTCH

| Exon | 5' Boundary[a] | Nucleotide Position[b] | Exon Size | 3' boundary[a] | Reading Frame[c] | Primers | |
|---|---|---|---|---|---|---|---|
| 1 | ND[d] | ND | ND | AAG\|gtgnat | ND | | |
| 2 | ND | 202 | 193 | AAG\|gtaaga | 3 | | |
| 3 | tgtcag\|T | 395 | 190 | CAG\|gtaagg | 1 | 3F | GAGTTTGCAGTGATGTTGCTATTC (SEQ ID NO: 23) |
| | | | | | | 3R | ACCGCCTTACCTGCTGCTC (SEQ ID NO: 24) |
| 4 | tattag\|G | 585 | 70 | CAG\|gtatat | 2 | 4F | TGCACTAATTTTCTTATTACAGTGAG (SEQ ID NO: 25) |
| | | | | | | 4R | TAAGGCACACTACTGGGGTG (SEQ ID NO: 26) |
| 5 | tgacag\|A | 655 | 92 | CCT\|gtaagt | 3 | 5F | GAACACCCCAGTAGTGTGCC (SEQ ID NO: 27) |
| | | | | | | 5R | TGAGTCCTAGAGAAGTCACAGACATC (SEQ ID NO: 28) |
| 6 | ttgcag\|A | 747 | 199 | AAA\|gtgagt | 2 | 6F | GGCTCTTTTCATGGTCTCGTC (SEQ ID NO: 29) |
| | | | | | | 6R | TGTTTTGCTCTCCACCCTTC (SEQ ID NO: 30) |
| 7 | ttttag\|C | 946 | 122 | CAG\|gtaagc | 3 | 7F | GCACTGGATTTTAACAAGGCATG (SEQ ID NO: 31) |
| | | | | | | 7R | AGGGCATAGATTGTCCTCGG (SEQ ID NO: 32) |
| 8 | ctgcag\|C | 1068 | 148 | GAG\|gtaaac | 2 | 8F | TGGGAATACTGATGATGTGCC (SEQ ID NO: 33) |
| | | | | | | 8R | CATAACCAGCGAGTCTGCAC (SEQ ID NO: 34) |
| 9 | ccacag\|G | 1216 | 132 | ATG\|gtaacg | 3 | 9F | CATTTGGGCATTTCGCATTC (SEQ ID NO: 35) |
| | | | | | | 9R | ACCAAACCAAACTCCAGCCC (SEQ ID NO: 36) |
| 10 | ttgcag\|C | 1348 | 156 | CAG\|gtacta3 | 3 | 10F | TGCCCCATTGTTCTGCTTG (SEQ ID NO: 37) |
| | | | | | | 10R | GGACAGCAGATAAATGGCTCC (SEQ ID NO: 38) |
| 11 | ctgtag\|G | 1504 | 99 | GAG\|gtaatg | 3 | 11F | GCATCTCGCATGTCTAATGCCAC (SEQ ID NO: 39) |
| | | | | | | 11R | AAGCTGTGATGTCCCCAAAG (SEQ ID NO: 40) |
| 12 | tcccag\|G | 1603 | 126 | CAG\|gtgagc | 3 | 12F | GACCATGTCCAGTGCAGCTC (SEQ ID NO: 41) |
| | | | | | | 12R | CGTTCAGGATCACCACAGCC (SEQ ID NO: 42) |

TABLE 1-continued

Primers and boundary sequences of PTCH

| Exon | 5' Boundary[a] | Nucleotide Position[b] | Exon Size | 3' boundary[a] | Reading Frame[c] | Primers |
|---|---|---|---|---|---|---|
| 13 | tcccag\|G | 1729 | 119 | AAG\|gtacat | 3 | 13F AGTCCTCTGATTGGGCGGAG (SEQ ID NO: 43)<br>13R CCATTCTGCACCCAATCAAAAG (SEQ ID NO: 44) |
| 14 | tttcag\|C | 1848 | 403 | AAG\|gtaatc | 2 | 14F AAAATGGCAGAATGAAAGCACC (SEQ ID NO: 45)<br>14R CTGATGAACTCCAAAGGTTCTG (SEQ ID NO: 46) |
| 15 | ttccag\|G | 2251 | 310 | AGG\|gtaaga | 3 | 15F GGAAGAGTCAGTGGTGCTCC (SEQ ID NO: 47)<br>15R CGCCAAAGACCGAAAGGAC (SEQ ID NO: 48) |
| 16 | ttctag\|G | 2561 | 143 | CAG\|gtactc | 1 | 16F AGGGTCCTTCTGGCTGCGAG (SEQ ID NO: 49)<br>16R GCTGTCAAGCAGCCTCCAC (SEQ ID NO: 50) |
| 17 | ttgtag\|T | 2704 | 184 | GAA\|gtaagt | 3 | 17F GCTCTCAAGGCAGAAGTGTG (SEQ ID NO: 51)<br>17R GGAAGGCACCTCTGTAAGTTC (SEQ ID NO: 52) |
| 18 | gtccag\|T | 2888 | 281 | ATT\|gtgagt | 1 | 18F GCTCCTAACCTGTGCCCTTC (SEQ ID NO: 53)<br>18R GAATTTGACTTCCACAAAGCCC (SEQ ID NO: 54) |
| 19 | ctccag\|G | 3169 | 138 | TTG\|gtatgg | 3 | 19F CGCCCACTGACCACTGTGTG (SEQ ID NO: 55)<br>19R GAGCCAGAGGAAATGGGTTG (SEQ ID NO: 56) |
| 20 | gcacag\|G | 3307 | 143 | CAG\|gtaagc | 3 | 20F AGCATTTACCAGGTGAAGTCC (SEQ ID NO: 57)<br>20R TTGCACACGCCTGCTTAC (SEQ ID NO: 58) |
| 21 | tcccag\|G | 3450 | 100 | GAG\|gtcagt | 2 | 21F TGTTCCCGTTTCCTCTTG (SEQ ID NO: 59)<br>21R GCACAGGAAACACAGCATTC (SEQ ID NO: 60) |
| 22 | aaatag\|G | 3550 | 255 | ACT\|gtaagt | 3 | 22F GCAGGTAAATGGACAAGAACAC (SEQ ID NO: 61)<br>22R ACTACCACGGTGGGAAGACC (SEQ ID NO: 62) |
| 23 | ctgcag\|G | 3805 | 541 | GAG/gtgagt | 3 | 23F CCCTTCTAACCCACCCTCAC (SEQ ID NO: 63)<br>23R GACACATCAGCCTTGCTC (SEQ ID NO: 64) |
| 24 | ND | 4346 | ND | ND | | |

[a]Consensus sequences for the 5' and 3' exonic boundaries are $(^t_c)_{11}$ncag\|G and AG\|gt$^g_a$agt, respectively (20). Upper case denotes exonic sequence.
[b]Exon positions are in reference to the coding sequence of PTCH (3) with the beginning ATG as nucleotide 1.
[c]5' exon boundary begins after the first, second, or third base of the codon of the translation reading frame.
[d]ND, not determined.

One report (Schofield, D. et al. supra) has shown that five medulloblastomas (two BCNS-associated cases and three sporadic cases) bearing LOH on chromosome 9q22.3-q31 are all of the desmoplastic subtype, suggesting LOH on 9q22.3 is histological subtype specific. We feel that the conclusion derived from only five positive tumors is a not strong one because we and others (Raffel, C. et al. (1997) Cancer Res 57:842-845) have found nondesmoplastic subtypes of medulloblastomas bearing LOH on chromosome 9q22.3.

Independently, another group has reported their finding of ptc mutations in sporadic medulloblastomas (Raffel, C. et al. supra).

A change of T to C at nucleotide 2990 (in exon 18) was identified in DNA from one of nine sporadic meningiomas, causing a predicted change of codon 997 from Ile to Thr (Table 2). The meningioma bearing this mutation also has allelic loss on 9q22.3. Blood cell DNA is heterozygous for this mutation, but DNA from the tumor contains only the mutant sequence. Of 100 normal chromosomes examined, none has this sequence change, suggesting that this mutation is not likely a common polymorphism. This patent is 84 years old and has had no phenotypic abnormalities suggestive of the BCNS, suggesting that this sequence alteration may not have caused complete inactivation of the ptc gene. None of the other eight meningiomas had detectable LOH at chromosome 9q.

TABLE 2

PATCHED gene alterations[a]

| Tumor | Pathology | Nucleotide | Codon | Exon | Consequence | LOH | Mutation Type |
|---|---|---|---|---|---|---|---|
| Med34 | Medulloblastoma (desmoplastic) | TC1869A | 623 | 14 | Frameshift | Yes | Somatic |
| Med36 | Medulloblastoma (classic) | G2503T | 835 | 15 | Glu to STOP | Yes | Somatic |
| Men1 | Meningioma | T2990C | 997 | 18 | Ile to Thr | Yes | Germ-line |
| Br349 | Breast carcinoma | T2863C | 955 | 17 | Tyr to His | Yes | Somatic |
| Br321 | Breast carcinoma | A2975G | 995 | 18 | Glu to Gly | No | Somatic |
| Co320 | Colon tumor cell line | A2000C | 667 | 14 | Glu to Ala | No | Unknown |
| Co8-1 | Colon carcinoma | T to C | Intron | 10 | Polymorphism | No | Germ-line |
| Co15-1 | Colon carcinoma | T to C | Intron | 10 | Polymorphism | No | Germ-line |

We also examined a variety of other tumors (10 primary tumors and 1 cell line), 18 bladder tumors (14 primary tumors and 4 cell lines), and 2 ovarian cancer cell lines. These tumors are not known to occur in higher than expected frequency in BCNS patients. We identified sequence abnormalities in two breast carcinomas and in the one colon cancer cell line (Table 2). The mutation found in breast carcinoma Br349 is not present in the patient's normal skin DNA, indicating that the sequence change is a somatic mutation. Direct sequencing of the PCR product indicated that only the mutant allele is present in the tumor. This mutation changes codon 955 from Tyr to His, and this Tyr is conserved in human, murine, chicken, and fly ptcII homologues (Goodrich, L. V. et al. (1996) *Genes Dev* 10:301-312). The mutation in breast carcinoma Br321 is predicted to change codon 995 from Glu to Gly, and the tumor with this mutation retains the wild-type allele. We have sequenced exon 18 in DNA from the blood of 50 normal persons and found no changes from the published sequence, suggesting that the sequence change found in Br321 is not a common polymorphism. Furthermore, examination of the DNA from the cultured skin fibroblasts of the patient did not reveal the same mutation, indicating that this is a somatic mutation.

Because DNA is not available from normal cells of the patient from which colon cell line 320 was established, we used simplified amplification of specific allele analysis (Lei, X. and Hall, B. G., supra) to examine 50 normal blood DNA samples for the presence of the sequence alteration and found none but the DNA from this cell line to have the mutant allele, suggesting that this mutation also is unlikely to be a common sequence polymorphism. For bladder carcinomas, a newly isolated microsatellite that was derived from intron 1 of the ptc gene was used to examine LOH in the tumor. Three primary bladder carcinomas showed LOH at this intragenic locus. With no ptc mutations detected in these tumors, we suspect that the LOH in these three bladder carcinomas may reflect the high incidence of while chromosome 9 loss in bladder cancers (Sidransky, D. et al., supra). A similar observation has been reported previously (Simoneau, A. R. et al. (1996) *Cancer Res* 56:5039-5043).

We also detected a sequence change in intron 10 in two colon carcinomas, 15-1 and 8-1, an alteration that was reported previously as a splicing mutation (Unden, A. B. et al. (1996) *Cancer Res* 56:4562-4565). Because we found the same sequence change in about 20% of normal control samples, we suggest that this more likely is a nonpathogenic polymorphism. The ptc protein is predicted to contain 12 transmembrane domains, two large extracellular loops, and one intracellular loop (Goodrich, L. V. et al., supra). Of the six mutations we identified, four are missense mutations. Three mutations lead to amino acid substitutions in the second extracellular loop, and one mutation results in an amino acid change in the intracellular domain.

Our data indicate that somatic inactivation of the ptc gene does occur in some sporadic medulloblastomas. In addition, because missense mutations of the ptc gene were detected in breast carcinomas, we suspect that defects of the ptc function also may be involved in some breast carcinomas, although biochemical evidence is necessary to show how these missense mutations might impair ptc function. Of 11 colon cancers and 18 bladder carcinomas examined, we found only one mutation in 1 colon cell line, suggesting that ptc gene mutations are relatively uncommon in colon and bladder cancers, although the incidence of chromosome 9 loss in bladder cancers is high (Cairns, P. et al., supra).

Published reports of SSCP analysis of tumor DNA identified mutations in the ptc gene in only 30% of sporadic BCCs, although chromosome 9q22.3 LOH was reported in more than 50% of these tumors (Gallani, M. R. et al., supra). It has been reported that heteroduplex/SSCP analysis of gene mutations is more sensitive than SSCP analysis (Spritz, R. A. et al., supra). In our studies, we were able to identify a point mutation in the 310-bp-PCR product from exon 15 using heteroduplex analysis, whereas SSCP analysis failed to reveal this sequence change (Table 2). Therefore, we suspect that there may be more mutations in BCCs than we have found thus far. Analysis of the ptc gene in BCNS patients and in sporadic BCCs has identified mutations scattered widely across the gene, and the majority of mutations were predicted to result in truncated proteins (Hahn, H. et al., supra; Johnson, R. L. et al., supra; Gallani, M. R. et al., supra; Chidambaram, A. et al. supra; Unden, A. B. et al, supra; Wicking, C. et al. (1997) *Am J Hum Genet* 60:21-26). In our screening, we found two breast carcinomas bearing missense mutations of the ptc gene. In one of these two tumors, B349, direct sequencing indicated a deletion of the other copy of the ptc gene. Any comparison of mutations in skin cancers versus extracutaneous tumors must consider the wholly different causes of these mutations; UV light is unique to the skin.

All publications and patent applications cited in this specification are herein incorporated by reference as if each individual publication or patent o application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of detecting patched expression or misexpression in a cell, comprising
    collecting a sample of cells from a mammalian subject;
    isolating nucleic acid from said cells;
    contacting the nucleic acid sample with one or more primers which specifically hybridize to a patched gene expressed in said cells under conditions such that expression of the patched gene, if present, occurs; and
    detecting patched expression or misexpression.

2. The method of claim 1, wherein said method comprises measuring patched mRNA expression.

3. The method of claim 1, wherein the sample comprises biopsy material.

4. The method of claim 1, wherein the same comprises blood.

5. The method of claim 1, wherein the one or more primers are PCR primers.

* * * * *

```
                         SEQUENCE LISTING

<160> NUMBER OF SEQ ID NOS: 64

<210> SEQ ID NO 1
<211> LENGTH: 736
<212> TYPE: DNA
<213> ORGANISM: Tribolium casteneum
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: modified_base
<222> LOCATION: (34)..(36)
<223> OTHER INFORMATION: a, c, t, g, unknown or other
<220> FEATURE:
<221> NAME/KEY: modified_base
<222> LOCATION: (39)..(41)
<223> OTHER INFORMATION: a, c, t, g, unknown or other
<220> FEATURE:
<221> NAME/KEY: modified_base
<222> LOCATION: (45)..(45)
<223> OTHER INFORMATION: a, c, t, g, unknown or other
<220> FEATURE:
<221> NAME/KEY: modified_base
<222> LOCATION: (51)..(52)
<223> OTHER INFORMATION: a, c, t, g, unknown or other
<220> FEATURE:
<221> NAME/KEY: modified_base
<222> LOCATION: (57)..(57)
<223> OTHER INFORMATION: a, c, t, g, unknown or other
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (71)..(71)
<223> OTHER INFORMATION: a, c, t, g, unknown or other
<220> FEATURE:
<221> NAME/KEY: modified_base
<222> LOCATION: (75)..(75)
<223> OTHER INFORMATION: a, c, t, g, unknown or other
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (87)..(89)
<223> OTHER INFORMATION: a, c, t, g, unknown or other
<220> FEATURE:
<221> NAME/KEY: modified_base
<222> LOCATION: (91)..(92)
<223> OTHER INFORMATION: a, c, t, g, unknown or other
<220> FEATURE:
<221> NAME/KEY: modified_base
<222> LOCATION: (96)..(97)
<223> OTHER INFORMATION: a, c, t, g, unknown or other
```

```
<220> FEATURE:
<221> NAME/KEY: modified_base
<222> LOCATION: (100)..(100)
<223> OTHER INFORMATION: a, c, t, g, unknown or other
<220> FEATURE:
<221> NAME/KEY: modified_base
<222> LOCATION: (104)..(104)
<223> OTHER INFORMATION: a, c, t, g, unknown or other
<220> FEATURE:
<221> NAME/KEY: modified_base
<222> LOCATION: (106)..(106)
<223> OTHER INFORMATION: a, c, t, g, unknown or other
<220> FEATURE:
<221> NAME/KEY: modified_base
<222> LOCATION: (109)..(109)
<223> OTHER INFORMATION: a, c, t, g, unknown or other
<220> FEATURE:
<221> NAME/KEY: modified_base
<222> LOCATION: (111)..(111)
<223> OTHER INFORMATION: a, c, t, g, unknown or other
<220> FEATURE:
<221> NAME/KEY: modified_base
<222> LOCATION: (113)..(113)
<223> OTHER INFORMATION: a, c, t, g, unknown or other
<220> FEATURE:
<221> NAME/KEY: modified_base
<222> LOCATION: (117)..(117)
<223> OTHER INFORMATION: a, c, t, g, unknown or other
<220> FEATURE:
<221> NAME/KEY: modified_base
<222> LOCATION: (120)..(120)
<223> OTHER INFORMATION: a, c, t, g, unknown or other
<220> FEATURE:
<221> NAME/KEY: modified_base
<222> LOCATION: (126)..(126)
<223> OTHER INFORMATION: a, c, t, g, unknown or other
<220> FEATURE:
<221> NAME/KEY: modified_base
<222> LOCATION: (149)..(149)
<223> OTHER INFORMATION: a, c, t, g, unknown or other
<220> FEATURE:
<221> NAME/KEY: modified_base
<222> LOCATION: (151)..(151)
<223> OTHER INFORMATION: a, c, t, g, unknown or other
<220> FEATURE:
<221> NAME/KEY: modified_base
<222> LOCATION: (153)..(154)
<223> OTHER INFORMATION: a, c, t, g, unknown or other
<220> FEATURE:
<221> NAME/KEY: modified_base
<222> LOCATION: (157)..(157)
<223> OTHER INFORMATION: a, c, t, g, unknown or other
<220> FEATURE:
<221> NAME/KEY: modified_base
<222> LOCATION: (178)..(178)
<223> OTHER INFORMATION: a, c, t, g, unknown or other
<220> FEATURE:
<221> NAME/KEY: modified_base
<222> LOCATION: (187)..(187)
<223> OTHER INFORMATION: a, c, t, g, unknown or other
<220> FEATURE:
<221> NAME/KEY: modified_base
<222> LOCATION: (189)..(189)
<223> OTHER INFORMATION: a, c, t, g, unknown or other
<220> FEATURE:
<221> NAME/KEY: modified_base
<222> LOCATION: (191)..(191)
<223> OTHER INFORMATION: a, c, t, g, unknown or other
<220> FEATURE:
<221> NAME/KEY: modified_base
<222> LOCATION: (211)..(211)
<223> OTHER INFORMATION: a, c, t, g, unknown or other
<220> FEATURE:
<221> NAME/KEY: modified_base
<222> LOCATION: (214)..(214)
<223> OTHER INFORMATION: a, c, t, g, unknown or other
<220> FEATURE:
<221> NAME/KEY: modified_base
<222> LOCATION: (310)..(310)
<223> OTHER INFORMATION: a, c, t, g, unknown or other
```

```
<220> FEATURE:
<221> NAME/KEY: modified_base
<222> LOCATION: (608)..(608)
<223> OTHER INFORMATION: a, c, t, g, unknown or other
<220> FEATURE:
<221> NAME/KEY: modified_base
<222> LOCATION: (704)..(704)
<223> OTHER INFORMATION: a, c, t, g, unknown or other
<220> FEATURE:
<221> NAME/KEY: modified_base
<222> LOCATION: (708)..(708)
<223> OTHER INFORMATION: a, c, t, g, unknown or other
<220> FEATURE:
<221> NAME/KEY: modified_base
<222> LOCATION: (712)..(712)
<223> OTHER INFORMATION: a, c, t, g, unknown or other
<220> FEATURE:
<221> NAME/KEY: modified_base
<222> LOCATION: (714)..(714)
<223> OTHER INFORMATION: a, c, t, g, unknown or other
<220> FEATURE:
<221> NAME/KEY: modified_base
<222> LOCATION: (729)..(729)
<223> OTHER INFORMATION: a, c, t, g, unknown or other
<220> FEATURE:
<221> NAME/KEY: modified_base
<222> LOCATION: (732)..(732)
<223> OTHER INFORMATION: a, c, t, g, unknown or other

<400> SEQUENCE: 1
aacnncnntn natggcaccc ccncccaacc tttnnnccnn ntaancaaaa nncccntttt      60
nataccccct ntaananttt tccaccnnnc nnaaanncen ctgnanacna ngnaaanccn     120
tttttnaacc ccccccaccc ggaattccna ntnnccncce ccaaattaca actccagncc     180
aaaattnana naattggtcc taacctaacc natngttgtt acggtttccc cccccaaata     240
catgcactgg cccgaacact tgatcgttgc cgttccaata agaataaatc tggtcatatt     300
aaacaagccn aaagctttac aaactgttgt acaattaatg ggcgaacacg aactgttcga     360
attctggtct ggacattaca aagtgcacca catcggatgg aaccaggaga aggccacaac     420
cgtactgaac gcctggcaga agaagttcgc acaggttggt ggttggcgca aggagtagag     480
tgaatggtgg taattttggg ttgttccagg aggtggatcg tctgacgaag agcaagaagt     540
cgtcgaatta catcttcgtg acgttctcca ccgccaattt gaacaagatg ttgaaggagg     600
cgtcgaanac ggacgtggtg aagctggggg tggtgctggg ggtggcggcg gtgtacgggt     660
gggtggccca gtcggggctg gctgccttgg gagtgctggt cttngcgngc tncnattcgc     720
cctatagtna gncgta                                                    736

<210> SEQ ID NO 2
<211> LENGTH: 107
<212> TYPE: PRT
<213> ORGANISM: Tribolium casteneum
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (20)..(20)
<223> OTHER INFORMATION: Any amino acid

<400> SEQUENCE: 2
```

```
Xaa Pro Pro Asn Tyr Asn Ser Xaa Pro Lys Xaa Xaa Xaa Leu Val
1               5                   10                  15

Leu Thr Pro Xaa Val Val Thr Val Ser Pro Pro Lys Tyr Met His Trp
            20                  25                  30

Pro Glu His Leu Ile Val Ala Val Pro Ile Arg Ile Asn Leu Val Ile
            35                  40                  45

Leu Asn Lys Pro Lys Ala Leu Gln Thr Val Val Gln Leu Met Gly Glu
        50                  55                  60

His Glu Leu Phe Glu Phe Trp Ser Gly His Tyr Lys Val His His Ile
65              70                  75                  80

Gly Trp Asn Gln Glu Lys Ala Thr Thr Val Leu Asn Ala Trp Gln Lys
                85                  90                  95

Lys Phe Ala Gln Val Gly Gly Trp Arg Lys Glu
                100                 105

<210> SEQ ID NO 3
<211> LENGTH: 5187
<212> TYPE: DNA
<213> ORGANISM: Precis coenia

<400> SEQUENCE: 3
gggtctgtca cccggagccg gagtccccgg cggccagcag cgtcctcgcg agccgagcgc      60
ccaggcgcgc ccggagcccg cggcggcggc ggcaacatgg cctcggctgg taacgccgcc     120
ggggccctgg gcaggcaggc cggcggcggg aggcgcagac ggaccggggg accgcaccgc     180
gccgcgccgg accgggacta tctgcaccgg cccagctact gcgacgccgc cttcgctctg     240
gagcagattt ccaaggggaa ggctactggc cggaaagcgc cgctgtggct gagagcgaag     300
tttcagagac tcttatttaa actgggttgt tacattcaaa agaactgcgg caagtttttg     360
gttgtgggtc tcctcatatt tggggccttc gctgtgggat taaaggcagc taatctcgag     420
accaacgtgg aggagctgtg ggtggaagtt ggtggacgag tgagtcgaga attaaattat     480
acccgtcaga agataggaga agaggctatg tttaatcctc aactcatgat acagactcca     540
aaagaagaag gcgctaatgt tctgaccaca gaggctctcc tgcaacacct ggactcagca     600
ctccaggcca gtcgtgtgca cgtctacatg tataacaggc aatggaagtt ggaacatttg     660
tgctacaaat caggggaact tatcacggag acaggttaca tggatcagat aatagaatac     720
cttttaccctt gcttaatcat tacacctttg gactgcttct gggaaggggc aaagctacag     780
tccgggacag catacctcct aggtaagcct cctttacggt ggacaaactt tgaccccttg     840
gaattcctag aagagttaaa gaaaataaac taccaagtgg acagctggga ggaaatgctg     900
aataaagccg aagttggcca tgggtacatg accggccctt gcctcaaccc agccgaccca     960
gattgccctg ccacagcccc taacaaaaat tcaaccaaac ctcttgatgt ggcccttgtt    1020
ttgaatggtg gatgtcaagg tttatccagg aagtatatgc attggcagga ggagttgatt    1080
gtgggtggta ccgtcaagaa tgccactgga aaacttgtca gcgctcacgc cctgcaaacc    1140
atgttccagt taatgactcc caagcaaatg tatgaacact caggggcta cgactatgtc    1200
tctcacatca actggaatga agacagggca gccgccatcc tggaggcctg cagaggact     1260
tacgtggagg tggttcatca aagtgtcgcc ccaaactcca ctcaaaaggt gcttcccttc    1320
acaaccacga ccctggacga catcctaaaa tccttctctg atgtcagtgt catccgagtg    1380
gccagcggct acctactgat gcttgcctat gcctgtttaa ccatgctgcg ctgggactgc    1440
tccaagtccc agggtgccgt ggggctggct ggcgtcctgt tggttgcgct gtcagtggct    1500
```

```
gcaggattgg gcctctgctc cttgattggc atttctttta atgctgcgac aactcaggtt    1560
ttgccgtttc ttgctcttgg tgttggtgtg atgatgtct  tcctcctggc ccatgcattc    1620
agtgaaacag gacagaataa gaggattcca tttgaggaca ggactgggga gtgcctcaag    1680
cgcaccggag ccagcgtggc cctcacctcc atcagcaatg tcaccgcctt cttcatggcc    1740
gcattgatcc ctatccctgc cctgcgagcg ttctccctcc aggctgctgt ggtggtggta    1800
ttcaattttg ctatggttct gctcattttt cctgcaattc tcagcatgga tttatacaga    1860
cgtgaggaca aagattgga  tattttctgc tgtttcacaa gcccctgtgt cagcagggtg    1920
attcaagttg agccacaggc ctacacagag cctcacagta acaccggta  cagcccccca    1980
cccccataca ccagccacag cttcgcccac gaaacccata tcactatgca gtccaccgtt    2040
cagctccgca cagagtatga ccctcacacg cacgtgtact acaccaccgc cgagccacgc    2100
tctgagatct ctgtacagcc tgttaccgtc acccaggaca acctcagctg tcagagtccc    2160
gagagcacca gctctaccag ggacctgctc tcccagttct cagactccag cctccactgc    2220
ctcgagcccc cctgcaccaa gtggacactc tcttcgtttg cagagaagca ctatgctcct    2280
ttcctcctga aacccaaagc caaggttgtg gtaatccttc ttttcctggg cttgctgggg    2340
gtcagccttt atgggaccac ccgagtgaga gacgggctgg acctcacgga cattgttccc    2400
cgggaaacca gagaatatga cttcatagct gcccagttca agtacttctc tttctacaac    2460
atgtatatag tcacccagaa agcagactac ccgaatatcc agcacctact ttacgacctt    2520
cataagagtt tcagcaatgt gaagtatgtc atgctggagg agaacaagca acttccccaa    2580
atgtggctgc actactttag agactggctt caaggacttc aggatgcatt tgacagtgac    2640
tgggaaactg ggaggatcat gccaaacaat tataaaaatg gatcagatga cggggtcctc    2700
gcttacaaac tcctggtgca gactggcagc cgagacaagc ccatcgacat tagtcagttg    2760
actaaacagc gtctggtaga cgcagatggc atcattaatc cgagcgcttt ctacatctac    2820
ctgaccgctt gggtcagcaa cgaccctgta gcttacgctg cctcccaggc caacatccgg    2880
cctcaccggc cggagtgggt ccatgacaaa gccgactaca tgccagagac caggctgaga    2940
atcccagcag cagagcccat cgagtacgct cagttcccct tctacctcaa cggcctacga    3000
gacacctcag actttgtgga agccatagaa aaagtgagag tcatctgtaa caactatacg    3060
agcctgggac tgtccagcta ccccaatggc taccccttcc tgttctggga gcaatacatc    3120
agcctgcgcc actggctgct gctatccatc agcgtggtgc tggcctgcac gtttctagtg    3180
tgcgcagtct tcctcctgaa cccctggacg gccgggatca ttgtcatggt cctggctctg    3240
atgaccgttg agctctttgg catgatgggc ctcattggga tcaagctgag tgctgtgcct    3300
gtggtcatcc tgattgcatc tgttggcatc ggagtggagt tcaccgtcca cgtggctttg    3360
gcctttctga cagccattgg ggacaagaac cacagggcta tgctcgctct ggaacacatg    3420
tttgctcccg ttctgacgg  tgctgtgtcc actctgctgg tgtactgat  gcttgcaggg    3480
tccgaatttg atttcattgt cagatacttc tttgccgtcc tggccattct caccgtcttg    3540
ggggttctca atggactggt tctgctgcct gtcctcttat ccttctttgg accgtgtcct    3600
gaggtgtctc cagccaatgg cctaaaccga ctgcccactc cttcgcctga ccgcctcca    3660
agtgtcgtcc ggtttgccgt gcctcctggt cacacgaaca atgggtctga ttcctccgac    3720
tcggagtaca gctctcagac cacggtgtct ggcatcagtg aggagctcag gcaatacgaa    3780
gcacagcagg gtgccggagg ccctgcccac caagtgattg tggaagccac agaaaaccct    3840
gtctttgccc ggtccactgt ggtccatccg gactccagac atcagcctcc cttgacccct    3900
```

```
cggcaacagc cccacctgga ctctggctcc ttgtcccctg gacggcaagg ccagcagcct    3960
cgaagggatc cccctagaga aggcttgcgg ccacccccct acagaccgcg cagagacgct    4020
tttgaaattt ctactgaagg gcattctggc cctagcaata gggaccgctc agggccccgt    4080
ggggcccgtt ctcacaaccc tcggaaccca acgtccaccg ccatgggcag ctctgtgccc    4140
agctactgcc agcccatcac cactgtgacg gcttctgctt cggtgactgt tgctgtgcat    4200
cccccgcctg gacctgggcg caaccccga ggggggccct gtccaggcta tgagagctac    4260
cctgagactg atcacggggt atttgaggat cctcatgtgc cttttcatgt caggtgtgag    4320
aggagggact caaaggtgga ggtcatagag ctacaggacg tggaatgtga ggagaggccg    4380
tgggggagca gctccaactg agggtaatta aaatctgaag caaagaggcc aaagattgga    4440
aagccccgcc cccacctctt tccagaactg cttgaagaga actgcttgga attatgggaa    4500
ggcagttcat tgttactgta actgattgta ttattkkgtg aaatatttct ataaatattt    4560
aaraggtgta cacatgtaat atacatggaa atgctgtaca gtctatttcc tggggcctct    4620
ccactcctgc cccagagtgg ggagaccaca ggggcccttt ccctgtgta cattggtctc    4680 tgtgccacaa ccaagcttaa cttagtttta aaaaaaatct cccagcatat gtcgctgctg    4740
cttaaatatt gtataattta cttgtataat tctatgcaaa tattgcttat gtaataggat    4800
tatttgtaaa ggtttctgtt taaaatattt taaatttgca tatcacaacc ctgtggtagg    4860
atgaattgtt actgttaact tttgaacacg ctatgcgtgg taattgttta acgagcagac    4920
atgaagaaaa caggttaatc ccagtggctt ctctaggggt agttgtatat ggttcgcatg    4980
ggtggatgtg tgtgtgcatg tgactttcca atgtactgta ttgtggtttg ttgttgttgt    5040
tgctgttgtt gttcattttg gtgttttttgg ttgctttgta tgatcttagc tctggcctag    5100
gtgggctggg aagtccagg tctttttctg tcgtgatgct ggtggaaagg tgaccccaat    5160
catctgtcct attctctggg actattc                                       5187
```

<210> SEQ ID NO 4
<211> LENGTH: 1318
<212> TYPE: PRT
<213> ORGANISM: Precis coenia

<400> SEQUENCE: 4

Met Val Ala Pro Asp Ser Glu Ala Pro Ser Asn Pro Arg Ile Thr Ala
1               5                   10                  15

Ala His Glu Ser Pro Cys Ala Thr Glu Ala Arg His Ser Ala Asp Leu
            20                  25                  30

Tyr Ile Arg Thr Ser Trp Val Asp Ala Ala Leu Ala Leu Ser Glu Leu
        35                  40                  45

Glu Lys Gly Asn Ile Glu Gly Gly Arg Thr Ser Leu Trp Ile Arg Ala
    50                  55                  60

Trp Leu Gln Glu Gln Leu Phe Ile Leu Gly Cys Phe Leu Gln Gly Asp
65                  70                  75                  80

Ala Gly Lys Val Leu Phe Val Ala Ile Leu Val Leu Ser Thr Phe Cys
                85                  90                  95

Val Gly Leu Lys Ser Ala Gln Ile His Thr Arg Val Asp Gln Leu Trp
            100                 105                 110

Val Gln Glu Gly Gly Arg Leu Glu Ala Glu Leu Lys Tyr Thr Ala Gln
        115                 120                 125

Ala Leu Gly Glu Ala Asp Ser Ser Thr His Gln Leu Val Ile Gln Thr
    130                 135                 140

Ala Lys Asp Pro Asp Val Ser Leu Leu His Pro Gly Ala Leu Leu Glu

```
            145                 150                 155                 160
His Leu Lys Val Val His Ala Ala Thr Arg Val Thr Val His Met Tyr
                165                 170                 175

Asp Ile Glu Trp Arg Leu Lys Asp Leu Cys Tyr Ser Pro Ser Ile Pro
            180                 185                 190

Asp Phe Glu Gly Tyr His His Ile Glu Ser Ile Ile Asp Asn Val Ile
            195                 200                 205

Pro Cys Ala Ile Ile Thr Pro Leu Asp Cys Phe Trp Glu Gly Ser Lys
    210                 215                 220

Leu Leu Gly Pro Asp Tyr Pro Ile Tyr Val Pro His Leu Lys His Lys
225                 230                 235                 240

Leu Gln Trp Thr His Leu Asn Pro Leu Glu Val Val Glu Glu Val Lys
                245                 250                 255

Lys Leu Lys Phe Gln Phe Pro Leu Ser Thr Ile Glu Ala Tyr Met Lys
                260                 265                 270

Arg Ala Gly Ile Thr Ser Ala Tyr Met Lys Lys Pro Cys Leu Asp Pro
                275                 280                 285

Thr Asp Pro His Cys Pro Ala Thr Ala Pro Asn Lys Lys Ser Gly His
    290                 295                 300

Ile Pro Asp Val Ala Ala Glu Leu Ser His Gly Cys Tyr Gly Phe Ala
305                 310                 315                 320

Ala Ala Tyr Met His Trp Pro Glu Gln Leu Ile Val Gly Gly Ala Thr
                325                 330                 335

Arg Asn Ser Thr Ser Ala Leu Arg Ser Ala Arg Ala Leu Gln Thr Val
                340                 345                 350

Val Gln Leu Met Gly Glu Arg Glu Met Tyr Glu Tyr Trp Ala Asp His
                355                 360                 365

Tyr Lys Val His Gln Ile Gly Trp Asn Gln Glu Lys Ala Ala Ala Val
                370                 375                 380

Leu Asp Ala Trp Gln Arg Lys Phe Ala Ala Glu Val Arg Lys Ile Thr
385                 390                 395                 400

Thr Ser Gly Ser Val Ser Ser Ala Tyr Ser Phe Tyr Pro Phe Ser Thr
                405                 410                 415

Ser Thr Leu Asn Asp Ile Leu Gly Lys Phe Ser Glu Val Ser Leu Lys
                420                 425                 430

Asn Ile Ile Leu Gly Tyr Met Phe Met Leu Ile Tyr Val Ala Val Thr
                435                 440                 445

Leu Ile Gln Trp Arg Asp Pro Ile Arg Ser Gln Ala Gly Val Gly Ile
                450                 455                 460

Ala Gly Val Leu Leu Leu Ser Ile Thr Val Ala Ala Gly Leu Gly Phe
465                 470                 475                 480

Cys Ala Leu Leu Gly Ile Pro Phe Asn Ala Ser Ser Thr Gln Ile Val
                485                 490                 495

Pro Phe Leu Ala Leu Gly Leu Gly Val Gln Asp Met Phe Leu Leu Thr
                500                 505                 510

His Thr Tyr Val Glu Gln Ala Gly Asp Val Pro Arg Glu Glu Arg Thr
                515                 520                 525

Gly Leu Val Leu Lys Lys Ser Gly Leu Ser Val Leu Leu Ala Ser Leu
                530                 535                 540

Cys Asn Val Met Ala Phe Leu Ala Ala Ala Leu Leu Pro Ile Pro Ala
545                 550                 555                 560

Phe Arg Val Phe Cys Leu Gln Ala Ala Ile Leu Leu Leu Phe Asn Leu
                565                 570                 575
```

-continued

Gly Ser Ile Leu Leu Val Phe Pro Ala Met Ile Ser Leu Asp Leu Arg
            580                 585                 590

Arg Arg Ser Ala Ala Pro Ala Asp Leu Leu Cys Cys Leu Met Pro Glu
        595                 600                 605

Ser Pro Leu Pro Lys Lys Lys Ile Pro Glu Arg Ala Lys Thr Arg Lys
610                 615                 620

Asn Asp Lys Thr His Arg Ile Asp Thr Thr Arg Gln Pro Leu Asp Pro
625                 630                 635                 640

Asp Val Ser Glu Asn Val Thr Lys Thr Cys Cys Leu Ser Val Ser Leu
                645                 650                 655

Thr Lys Trp Ala Lys Asn Gln Tyr Ala Pro Phe Ile Met Arg Pro Ala
            660                 665                 670

Val Lys Val Thr Ser Met Leu Ala Leu Ile Ala Val Ile Leu Thr Ser
        675                 680                 685

Val Trp Gly Ala Thr Lys Val Lys Asp Gly Leu Asp Leu Thr Asp Ile
690                 695                 700

Val Pro Glu Asn Thr Asp Glu His Glu Phe Leu Ser Arg Gln Glu Lys
705                 710                 715                 720

Tyr Phe Gly Phe Tyr Asn Met Tyr Ala Val Thr Gln Gly Asn Phe Glu
                725                 730                 735

Tyr Pro Thr Asn Gln Lys Leu Leu Tyr Glu Tyr His Asp Gln Phe Val
            740                 745                 750

Arg Ile Pro Asn Ile Ile Lys Asn Asp Asn Gly Gly Leu Thr Lys Phe
        755                 760                 765

Trp Leu Ser Leu Phe Arg Asp Trp Leu Asp Leu Gln Val Ala Phe
770                 775                 780

Asp Lys Glu Val Ala Ser Gly Cys Ile Thr Gln Glu Tyr Trp Cys Lys
785                 790                 795                 800

Asn Ala Ser Asp Glu Gly Ile Leu Ala Tyr Lys Leu Met Val Gln Thr
                805                 810                 815

Gly His Val Asp Asn Pro Ile Asp Lys Ser Leu Ile Thr Ala Gly His
            820                 825                 830

Arg Leu Val Asp Lys Asp Gly Ile Ile Asn Pro Lys Ala Phe Tyr Asn
        835                 840                 845

Tyr Leu Ser Ala Trp Ala Thr Asn Asp Ala Leu Ala Tyr Gly Ala Ser
850                 855                 860

Gln Gly Asn Leu Lys Pro Gln Pro Gln Arg Trp Ile His Ser Pro Glu
865                 870                 875                 880

Asp Val His Leu Glu Ile Lys Lys Ser Ser Pro Leu Ile Tyr Thr Gln
                885                 890                 895

Leu Pro Phe Tyr Leu Ser Gly Leu Ser Asp Thr Asp Ser Ile Lys Thr
            900                 905                 910

Leu Ile Arg Ser Val Arg Asp Leu Cys Leu Lys Tyr Glu Ala Lys Gly
        915                 920                 925

Leu Pro Asn Phe Pro Ser Gly Ile Pro Phe Leu Phe Trp Glu Gln Tyr
930                 935                 940

Leu Tyr Leu Arg Thr Ser Leu Leu Leu Ala Leu Cys Ala Leu Gly
945                 950                 955                 960

Ala Val Phe Ile Ala Val Met Val Leu Leu Asn Ala Trp Ala Ala
                965                 970                 975

Val Leu Val Thr Leu Ala Leu Ala Thr Leu Val Leu Gln Leu Leu Gly
            980                 985                 990

Val Met Ala Leu Leu Gly Val Lys  Leu Ser Ala Met Pro  Pro Val Leu
        995                  1000                 1005

| | | | | | | | | | | |
|---|---|---|---|---|---|---|---|---|---|---|
| Leu | Val | Leu | Ala | Ile | Gly | Arg | Gly | Val | His | Phe | Thr | Val | His | Leu |
| 1010 | | | | | 1015 | | | | | 1020 |

| Cys | Leu | Gly | Phe | Val | Thr | Ser | Ile | Gly | Cys | Lys | Arg | Arg | Arg | Ala |
|---|---|---|---|---|---|---|---|---|---|---|---|---|---|---|
| 1025 | | | | | 1030 | | | | | 1035 | | | | |

| Ser | Leu | Ala | Leu | Glu | Ser | Val | Leu | Ala | Pro | Val | Val | His | Gly | Ala |
|---|---|---|---|---|---|---|---|---|---|---|---|---|---|---|
| 1040 | | | | | 1045 | | | | | 1050 | | | | |

| Leu | Ala | Ala | Ala | Leu | Ala | Ala | Ser | Met | Leu | Ala | Ala | Ser | Glu | Phe |
|---|---|---|---|---|---|---|---|---|---|---|---|---|---|---|
| 1055 | | | | | 1060 | | | | | 1065 | | | | |

| Gly | Phe | Val | Ala | Arg | Leu | Phe | Leu | Arg | Leu | Leu | Leu | Ala | Leu | Val |
|---|---|---|---|---|---|---|---|---|---|---|---|---|---|---|
| 1070 | | | | | 1075 | | | | | 1080 | | | | |

| Phe | Leu | Gly | Leu | Ile | Asp | Gly | Leu | Leu | Phe | Phe | Pro | Ile | Val | Leu |
|---|---|---|---|---|---|---|---|---|---|---|---|---|---|---|
| 1085 | | | | | 1090 | | | | | 1095 | | | | |

| Ser | Ile | Leu | Gly | Pro | Ala | Ala | Glu | Val | Arg | Pro | Ile | Glu | His | Pro |
|---|---|---|---|---|---|---|---|---|---|---|---|---|---|---|
| 1100 | | | | | 1105 | | | | | 1110 | | | | |

| Glu | Arg | Leu | Ser | Thr | Pro | Ser | Pro | Lys | Cys | Ser | Pro | Ile | His | Pro |
|---|---|---|---|---|---|---|---|---|---|---|---|---|---|---|
| 1115 | | | | | 1120 | | | | | 1125 | | | | |

| Arg | Lys | Ser | Ser | Ser | Ser | Gly | Gly | Gly | Asp | Lys | Ser | Ser | Arg |
|---|---|---|---|---|---|---|---|---|---|---|---|---|---|
| 1130 | | | | | 1135 | | | | | 1140 | | | | |

| Thr | Ser | Lys | Ser | Ala | Pro | Arg | Pro | Cys | Ala | Pro | Ser | Leu | Thr | Thr |
|---|---|---|---|---|---|---|---|---|---|---|---|---|---|---|
| 1145 | | | | | 1150 | | | | | 1155 | | | | |

| Ile | Thr | Glu | Glu | Pro | Ser | Ser | Trp | His | Ser | Ser | Ala | His | Ser | Val |
|---|---|---|---|---|---|---|---|---|---|---|---|---|---|---|
| 1160 | | | | | 1165 | | | | | 1170 | | | | |

| Gln | Ser | Ser | Met | Gln | Ser | Ile | Val | Val | Gln | Pro | Glu | Val | Val | Val |
|---|---|---|---|---|---|---|---|---|---|---|---|---|---|---|
| 1175 | | | | | 1180 | | | | | 1185 | | | | |

| Glu | Thr | Thr | Thr | Tyr | Asn | Gly | Ser | Asp | Ser | Ala | Ser | Gly | Arg | Ser |
|---|---|---|---|---|---|---|---|---|---|---|---|---|---|---|
| 1190 | | | | | 1195 | | | | | 1200 | | | | |

| Thr | Pro | Thr | Lys | Ser | Ser | His | Gly | Gly | Ala | Ile | Thr | Thr | Thr | Lys |
|---|---|---|---|---|---|---|---|---|---|---|---|---|---|---|
| 1205 | | | | | 1210 | | | | | 1215 | | | | |

| Val | Thr | Ala | Thr | Ala | Asn | Ile | Lys | Val | Glu | Val | Thr | Pro | Ser |
|---|---|---|---|---|---|---|---|---|---|---|---|---|---|
| 1220 | | | | | 1225 | | | | | 1230 | | | | |

| Asp | Arg | Lys | Ser | Arg | Arg | Ser | Tyr | His | Tyr | Tyr | Asp | Arg | Arg | Arg |
|---|---|---|---|---|---|---|---|---|---|---|---|---|---|---|
| 1235 | | | | | 1240 | | | | | 1245 | | | | |

| Asp | Arg | Asp | Glu | Asp | Arg | Asp | Arg | Asp | Arg | Glu | Arg | Asp | Arg | Asp |
|---|---|---|---|---|---|---|---|---|---|---|---|---|---|---|
| 1250 | | | | | 1255 | | | | | 1260 | | | | |

| Arg | Asp | Arg | Asp | Arg | Asp | Arg | Asp | Arg | Asp | Arg | Asp | Arg | Asp | Arg |
|---|---|---|---|---|---|---|---|---|---|---|---|---|---|---|
| 1265 | | | | | 1270 | | | | | 1275 | | | | |

| Asp | Arg | Glu | Arg | Ser | Arg | Glu | Arg | Asp | Arg | Pro | Asp | Arg | Tyr | Arg |
|---|---|---|---|---|---|---|---|---|---|---|---|---|---|---|
| 1280 | | | | | 1285 | | | | | 1290 | | | | |

| Asp | Glu | Pro | Asp | His | Pro | Ala | Ser | Pro | Arg | Glu | Asn | Gly | Arg | Asp |
|---|---|---|---|---|---|---|---|---|---|---|---|---|---|---|
| 1295 | | | | | 1300 | | | | | 1305 | | | | |

| Ser | Gly | His | Glu | Ser | Asp | Ser | Ser | Arg | His |
|---|---|---|---|---|---|---|---|---|---|
| 1310 | | | | | 1315 | | | | |

<210> SEQ ID NO 5
<211> LENGTH: 4434
<212> TYPE: DNA
<213> ORGANISM: Drosophila melanogaster

<400> SEQUENCE: 5

```
cgaaacaaga gagcgagtga gagtagggag agcgtctgtg ttgtgtgttg agtgtcgccc      60
acgcacacag gcgcaaaaca gtgcacacag acgcccgctg ggcaagagag agtgagagag     120
agaaacagcg gcgcgcgctc gcctaatgaa gttgttggcc tggctggcgt gccgcatcca     180
cgagatacag atacatctct catggaccgc gacagcctcc cacgcgttcc ggacacacac     240
```

```
ggcgatgtgg tcgatgagaa attattctcg gatctttaca tacgcaccag ctgggtggac    300
gcccaagtgg cgctcgatca gatagataag ggcaaagcgc gtggcagccg cacggcgatc    360
tatctgcgat cagtattcca gtcccacctc gaaaccctcg gcagctccgt gcaaaagcac    420
gcgggcaagt tgctattcgt ggctatcctg gtgctgagca ccttctgcgt cggcctgaag    480
agcgcccaga tccactccaa ggtgcaccag ctgtggatcc aggagggcgg ccggctggag    540
gcggaactgc cctacacaca gaagacgatc ggcgaggacg agtcggccac gcatcagctg    600
ctcattcaga cgacccacga cccgaacgcc tccgtcctgc atccgcaggc gctgcttgcc    660
cacctggagg tcctggtcaa ggccaccgcc gtcaaggtgc acctctacga caccgaatgg    720
gggctgcgcg acatgtgcaa catgccgagc acgccctcct tcgagggcat ctactacatc    780
gagcagatcc tgcgccacct cattccgtgc tcgatcatca cgccgctgga ctgtttctgg    840
gagggaagcc agctgttggg tccggaatca gcggtcgtta taccaggcct caaccaacga    900
ctcctgtgga ccaccctgaa tcccgcctct gtgatgcagt atatgaaaca aaagatgtcc    960
gaggaaaaga tcagcttcga cttcgagacc gtggagcagt acatgaagcg tgcggccatt   1020
ggcagtggct acatggagaa gccctgcctg aacccactga atcccaattg cccggacacg   1080
gcaccgaaca agaacagcac ccagccgccg gatgtgggag ccatcctgtc cggaggctgc   1140
tacggttatg ccgcgaagca catgcactgg ccggaggagc tgattgtggg cggacggaag   1200
aggaaccgca gcggacactt gaggaaggcc caggccctgc agtcggtggt gcagctgatg   1260
accgagaagg aaatgtacga ccagtggcag gacaactaca aggtgcacca tcttggatgg   1320
acgcaggaga aggcagcgga ggttttgaac gcctggcagc gcaacttttc gcgggaggtg   1380
gaacagctgc tacgtaaaca gtcgagaatt gccaccaact acgatatcta cgtgttcagc   1440
tcggctgcac tggatgacat cctggccaag ttctcccatc ccagcgcctt gtccattgtc   1500
atcggcgtgg ccgtcaccgt tttgtatgcc ttttgcacgc tcctccgctg gagggacccc   1560
gtccgtggcc agagcagtgt gggcgtggcc ggagttctgc tcatgtgctt cagtaccgcc   1620
gccggattgg gattgtcagc cctgctcggt atcgttttca atgcgctgac cgctgcctat   1680
gcggagagca atcggcggga gcagaccaag ctgattctca gaacgccag cacccaggtg   1740 gttccgtttt tggcccttgg tctgggcgtc gatcacatct tcatagtggg accgagcatc   1800
ctgttcagtg cctgcagcac cgcaggatcc ttctttgcgg ccgcctttat tccggtgccg   1860
gctttgaagg tattctgtct gcaggctgcc atcgtaatgt gctccaattt ggcagcggct   1920
ctattggttt ttccggccat gatttcgttg gatctacgga gacgtaccgc cggcagggcg   1980
gacatcttct gctgctgttt tccggtgtgg aaggaacagc cgaaggtggc acctccggtg   2040
ctgccgctga caacaacaa cgggcgcggg gcccggcatc cgaagagctg caacaacaac   2100
agggtgccgc tgcccgccca gaatcctctg ctggaacaga gggcagacat ccctgggagc   2160
agtcactcac tggcgtccct ctccctggca accttcgcct ttcagcacta cactcccttc   2220
ctcatgcgca gctgggtgaa gttcctgacc gttatgggtt tcctggcggc cctcatatcc   2280
agcttgtatg cctccacgcg ccttcaggat ggcctggaca ttattgatct ggtgcccaag   2340
gacagcaacg agcacaagtt cctggatgct caaactcggc tctttggctt ctacagcatg   2400
tatgcggtta cccagggcaa cttttgaatat cccacccagc agcagttgct cagggactac   2460
catgattcct ttgtgcgggt gccacatgtg atcaagaatg ataacggtgg actgccggac   2520
ttctggctgc tgctcttcag cgagtggctg ggtaatctgc aaaagatatt cgacgaggaa   2580
taccgcgacg gacggctgac caaggagtgc tggttcccaa acgccagcag cgatgccatc   2640
```

-continued

```
ctggcctaca agctaatcgt gcaaaccggc catgtggaca accccgtgga caaggaactg    2700
gtgctcacca atcgcctggt caacagcgat ggcatcatca accaacgcgc cttctacaac    2760
tatctgtcgg catgggccac caacgacgtc ttcgcctacg agcttctca gggcaaattg     2820
tatccggaac cgcgccagta ttttcaccaa cccaacgagt acgatcttaa gatacccaag    2880
agtctgccat tggtctacgc tcagatgccc ttttacctcc acggactaac agatacctcg    2940
cagatcaaga ccctgatagg tcatattcgc gacctgagcg tcaagtacga gggcttcggc    3000
ctgcccaact atccatcggg cattcccttc atcttctggg agcagtacat gaccctgcgc    3060
tcctcactgg ccatgatcct ggcctgcgtg ctactcgccg ccctggtgct ggtctccctg    3120
ctcctgctct ccgtttgggc cgccgttctc gtgatcctca gcgttctggc ctcgctggcc    3180
cagatctttg ggccatgac tctgctgggc atcaaactct cggccattcc ggcagtcata    3240
ctcatcctca gcgtgggcat gatgctgtgc ttcaatgtgc tgatatcact gggcttcatg    3300
acatccgttg caaccgaca cgccgcgtc cagctgagca tgcagatgtc cctgggacca    3360
cttgtccacg gcatgctgac ctcggagtg gccgtgttca tgctctccac gtcgcccttt    3420
gagtttgtga tccggcactt ctgctggctt ctgctggtgg tcttatgcgt tggcgcctgc    3480
aacagccttt tggtgttccc catcctactg agcatggtgg accggaggc ggagctggtg    3540
ccgctggagc atccagaccg catatccacg ccctctccgc tgcccgtgcg cagcagcaag    3600
agatcgggca atcctatgt ggtgcaggga tcgcgatcct cgcgaggcag ctgccagaag    3660
tcgcatcacc accaccacaa agaccttaat gatccatcgc tgacgacgat caccgaggag    3720
ccgcagtcgt ggaagtccag caactcgtcc atccagatgc caatgattg gacctaccag    3780
ccgcgggaac agcgaccgc ctcctacgcg gccccgcccc cgcctatca aaggccgcc     3840
gcccagcagc accaccagca tcagggcccg cccacaacgc ccccgcctcc cttcccgacg    3900
gcctatccgc cggagctgca gagcatcgtg gtgcagccgg aggtgacggt ggagacgacg    3960
cactcggaca gcaacaccac caaggtgacg gcccacggcca acatcaaggt ggagctggcc    4020
atgcccggca gggcggtgcg cagctataac tttacgagtt agcactagca ctagttcctg    4080
tagctattag gacgtatctt tagactctag cctaagccgt aaccctattt gtatctgtaa    4140
aatcgatttg tccagcgggt ctgctgagga tttcgttctc atggattctc atggattctc    4200
atggatgctt aaatggcatg gtaattggca aaatatcaat ttttgtgtct caaaagatg     4260
cattagctta tggtttcaag atacatttt aaagagtccg ccagatattt atataaaaaa    4320
aatccaaaat cgacgtatcc atgaaaattg aaaagctaag cagacccgta tgtatgtata    4380
tgtgtatgca tgttagttaa tttcccgaag tccggtattt atagcagctg cctt          4434
```

<210> SEQ ID NO 6
<211> LENGTH: 1285
<212> TYPE: PRT
<213> ORGANISM: Drosophila melanogaster

<400> SEQUENCE: 6

```
Met Asp Arg Asp Ser Leu Pro Arg Val Pro Asp Thr His Gly Asp Val
 1               5                  10                  15

Val Asp Glu Lys Leu Phe Ser Asp Leu Tyr Ile Arg Thr Ser Trp Val
            20                  25                  30

Asp Ala Gln Val Ala Leu Asp Gln Ile Asp Lys Gly Lys Ala Arg Gly
        35                  40                  45

Ser Arg Thr Ala Ile Tyr Leu Arg Ser Val Phe Gln Ser His Leu Glu
    50                  55                  60
```

```
        Thr Leu Gly Ser Ser Val Gln Lys His Ala Gly Lys Val Leu Phe Val
        65                  70                  75                  80

Ala Ile Leu Val Leu Ser Thr Phe Cys Val Gly Leu Lys Ser Ala Gln
                        85                  90                  95

Ile His Ser Lys Val His Gln Leu Trp Ile Gln Glu Gly Gly Arg Leu
                    100                 105                 110

Glu Ala Glu Leu Ala Tyr Thr Gln Lys Thr Ile Gly Glu Asp Glu Ser
                115                 120                 125

Ala Thr His Gln Leu Leu Ile Gln Thr Thr His Asp Pro Asn Ala Ser
            130                 135                 140

Val Leu His Pro Gln Ala Leu Leu Ala His Leu Glu Val Leu Val Lys
        145                 150                 155                 160

Ala Thr Ala Val Lys Val His Leu Tyr Asp Thr Glu Trp Gly Leu Arg
                        165                 170                 175

Asp Met Cys Asn Met Pro Ser Thr Pro Ser Phe Glu Gly Ile Tyr Tyr
                    180                 185                 190

Ile Glu Gln Ile Leu Arg His Leu Ile Pro Cys Ser Ile Ile Thr Pro
                195                 200                 205

Leu Asp Cys Phe Trp Glu Gly Ser Gln Leu Leu Gly Pro Glu Ser Ala
            210                 215                 220

Val Val Ile Pro Gly Leu Asn Gln Arg Leu Leu Trp Thr Thr Leu Asn
        225                 230                 235                 240

Pro Ala Ser Val Met Gln Tyr Met Lys Gln Lys Met Ser Glu Glu Lys
                        245                 250                 255

Ile Ser Phe Asp Phe Glu Thr Val Glu Gln Tyr Met Lys Arg Ala Ala
                    260                 265                 270

Ile Gly Ser Gly Tyr Met Glu Lys Pro Cys Leu Asn Pro Leu Asn Pro
                275                 280                 285

Asn Cys Pro Asp Thr Ala Pro Asn Lys Asn Ser Thr Gln Pro Pro Asp
            290                 295                 300

Val Gly Ala Ile Leu Ser Gly Gly Cys Tyr Gly Tyr Ala Ala Lys His
        305                 310                 315                 320

Met His Trp Pro Glu Glu Leu Ile Val Gly Gly Arg Lys Arg Asn Arg
                        325                 330                 335

Ser Gly His Leu Arg Lys Ala Gln Ala Leu Gln Ser Val Val Gln Leu
                    340                 345                 350

Met Thr Glu Lys Glu Met Tyr Asp Gln Trp Gln Asp Asn Tyr Lys Val
                355                 360                 365

His His Leu Gly Trp Thr Gln Glu Lys Ala Ala Glu Val Leu Asn Ala
            370                 375                 380

Trp Gln Arg Asn Phe Ser Arg Glu Val Glu Gln Leu Leu Arg Lys Gln
        385                 390                 395                 400

Ser Arg Ile Ala Thr Asn Tyr Asp Ile Tyr Val Phe Ser Ser Ala Ala
                        405                 410                 415

Leu Asp Asp Ile Leu Ala Lys Phe Ser His Pro Ser Ala Leu Ser Ile
                    420                 425                 430

Val Ile Gly Val Ala Val Thr Val Leu Tyr Ala Phe Cys Thr Leu Leu
                435                 440                 445

Arg Trp Arg Asp Pro Val Arg Gly Gln Ser Ser Val Gly Val Ala Gly
            450                 455                 460

Val Leu Leu Met Cys Phe Ser Thr Ala Gly Leu Gly Leu Ser Ala
        465                 470                 475                 480

Leu Leu Gly Ile Val Phe Asn Ala Leu Thr Ala Ala Tyr Ala Glu Ser
                        485                 490                 495
```

-continued

```
Asn Arg Arg Glu Gln Thr Lys Leu Ile Leu Lys Asn Ala Ser Thr Gln
            500                 505                 510

Val Val Pro Phe Leu Ala Leu Gly Leu Gly Val Asp His Ile Phe Ile
            515                 520                 525

Val Gly Pro Ser Ile Leu Phe Ser Ala Cys Ser Thr Ala Gly Ser Phe
            530                 535                 540

Phe Ala Ala Ala Phe Ile Pro Val Pro Ala Leu Lys Val Phe Cys Leu
545                 550                 555                 560

Gln Ala Ala Ile Val Met Cys Ser Asn Leu Ala Ala Ala Leu Leu Val
            565                 570                 575

Phe Pro Ala Met Ile Ser Leu Asp Leu Arg Arg Thr Ala Gly Arg
            580                 585                 590

Ala Asp Ile Phe Cys Cys Cys Phe Pro Val Trp Lys Glu Gln Pro Lys
            595                 600                 605

Val Ala Pro Pro Val Leu Pro Leu Asn Asn Asn Gly Arg Gly Ala
            610                 615                 620

Arg His Pro Lys Ser Cys Asn Asn Asn Arg Val Pro Leu Pro Ala Gln
625                 630                 635                 640

Asn Pro Leu Leu Glu Gln Arg Ala Asp Ile Pro Gly Ser Ser His Ser
            645                 650                 655

Leu Ala Ser Phe Ser Leu Ala Thr Phe Ala Phe Gln His Tyr Thr Pro
            660                 665                 670

Phe Leu Met Arg Ser Trp Val Lys Phe Leu Thr Val Met Gly Phe Leu
            675                 680                 685

Ala Ala Leu Ile Ser Ser Leu Tyr Ala Ser Thr Arg Leu Gln Asp Gly
            690                 695                 700

Leu Asp Ile Ile Asp Leu Val Pro Lys Asp Ser Asn Glu His Lys Phe
705                 710                 715                 720

Leu Asp Ala Gln Thr Arg Leu Phe Gly Phe Tyr Ser Met Tyr Ala Val
            725                 730                 735

Thr Gln Gly Asn Phe Glu Tyr Pro Thr Gln Gln Leu Leu Arg Asp
            740                 745                 750

Tyr His Asp Ser Phe Arg Val Pro His Val Ile Lys Asn Asp Asn Gly
            755                 760                 765

Gly Leu Pro Asp Phe Trp Leu Leu Phe Ser Glu Trp Leu Gly Asn
            770                 775                 780

Leu Gln Lys Ile Phe Asp Glu Glu Tyr Arg Asp Gly Arg Leu Thr Lys
785                 790                 795                 800

Glu Cys Trp Phe Pro Asn Ala Ser Ser Asp Ala Ile Leu Ala Tyr Lys
            805                 810                 815

Leu Ile Val Gln Thr Gly His Val Asp Asn Pro Val Asp Lys Glu Leu
            820                 825                 830

Val Leu Thr Asn Arg Leu Val Asn Ser Asp Gly Ile Ile Asn Gln Arg
            835                 840                 845

Ala Phe Tyr Asn Tyr Leu Ser Ala Trp Ala Thr Asn Asp Val Phe Ala
            850                 855                 860

Tyr Gly Ala Ser Gln Gly Lys Leu Tyr Pro Glu Pro Arg Gln Tyr Phe
865                 870                 875                 880

His Gln Pro Asn Glu Tyr Asp Leu Lys Ile Pro Lys Ser Leu Pro Leu
            885                 890                 895

Val Tyr Ala Gln Met Pro Phe Tyr Leu His Gly Leu Thr Asp Thr Ser
            900                 905                 910

Gln Ile Lys Thr Leu Ile Gly His Ile Arg Asp Leu Ser Val Lys Tyr
```

```
                915                 920                 925
Glu Gly Phe Gly Leu Pro Asn Tyr Pro Ser Gly Ile Pro Phe Ile Phe
930                 935                 940
Trp Glu Gln Tyr Met Thr Leu Arg Ser Ser Leu Ala Met Ile Leu Ala
945                 950                 955                 960
Cys Val Leu Ala Ala Leu Val Leu Ser Val Ser Leu Leu Leu Leu Ser
                965                 970                 975
Val Trp Ala Ala Val Leu Val Ile Leu Ser Val Leu Ala Ser Leu Ala
            980                 985                 990
Gln Ile Phe Gly Ala Met Thr Leu Leu Gly Ile Lys Leu Ser Ala Ile
        995                 1000                1005
Pro Ala Val Ile Leu Ile Leu Ser Val Gly Met Met Leu Cys Phe
    1010                1015                1020
Asn Val Leu Ile Ser Leu Gly Phe Met Thr Ser Val Gly Asn Arg
    1025                1030                1035
Gln Arg Arg Val Gln Leu Ser Met Gln Met Ser Leu Gly Pro Leu
    1040                1045                1050
Val His Gly Met Leu Thr Ser Gly Val Ala Val Phe Met Leu Ser
    1055                1060                1065
Thr Ser Pro Phe Glu Phe Val Ile Arg His Phe Cys Trp Leu Leu
    1070                1075                1080
Leu Val Leu Cys Val Gly Ala Cys Asn Ser Leu Leu Val Phe
    1085                1090                1095
Pro Ile Leu Leu Ser Met Val Gly Pro Glu Ala Glu Leu Val Pro
    1100                1105                1110
Leu Glu His Pro Asp Arg Ile Ser Thr Pro Ser Pro Leu Pro Val
    1115                1120                1125
Arg Ser Ser Lys Arg Ser Gly Lys Ser Tyr Val Gln Gly Ser
    1130                1135                1140
Arg Ser Ser Arg Gly Ser Cys Gln Lys Ser His His His His His
    1145                1150                1155
Lys Asp Leu Asn Asp Pro Ser Leu Thr Thr Ile Thr Glu Glu Pro
    1160                1165                1170
Gln Ser Trp Lys Ser Ser Asn Ser Ser Ile Gln Met Pro Asn Asp
    1175                1180                1185
Trp Thr Tyr Gln Pro Arg Glu Gln Arg Pro Ala Ser Tyr Ala Ala
    1190                1195                1200
Pro Pro Pro Ala Tyr His Lys Ala Ala Ala Gln Gln His His Gln
    1205                1210                1215
His Gln Gly Pro Pro Thr Thr Pro Pro Pro Pro Phe Pro Thr Ala
    1220                1225                1230
Tyr Pro Pro Glu Leu Gln Ser Ile Val Val Gln Pro Glu Val Thr
    1235                1240                1245
Val Glu Thr Thr His Ser Asp Ser Asn Thr Thr Lys Val Thr Ala
    1250                1255                1260
Thr Ala Asn Ile Lys Val Glu Leu Ala Met Pro Gly Arg Ala Val
    1265                1270                1275
Arg Ser Tyr Asn Phe Thr Ser
    1280                1285

<210> SEQ ID NO 7
<211> LENGTH: 345
<212> TYPE: DNA
<213> ORGANISM: Anopheles gambiae
<220> FEATURE:
```

```
<221> NAME/KEY: modified_base
<222> LOCATION: (114)..(114)
<223> OTHER INFORMATION: a, c, t, g, unknown or other
<220> FEATURE:
<221> NAME/KEY: modified_base
<222> LOCATION: (225)..(225)
<223> OTHER INFORMATION: a, c, t, g, unknown or other
<220> FEATURE:
<221> NAME/KEY: modified_base
<222> LOCATION: (261)..(261)
<223> OTHER INFORMATION: a, c, t, g, unknown or other

<400> SEQUENCE: 7
aaggtccatc agctttggat acaggaaggt ggttcgctcg agcatgagct agcctacacg      60
cagaaatcgc tcggcgagat ggactcctcc acgcaccagc tgctaatcca aacncccaaa    120
gatatggacg cctcgatact gcacccgaac gcgctactga cgcacctgga cgtggtgaag    180
aaagcgatct cggtgacggt gcacatgtac gacatcacgt ggagnctcaa ggacatgtgc    240
tactcgccca gcataccgag nttcgatacg cactttatcg agcagatctt cgagaacatc    300
ataccgtgcg cgatcatcac gccgctggat tgcttttggg aggga                     345

<210> SEQ ID NO 8
<211> LENGTH: 115
<212> TYPE: PRT
<213> ORGANISM: Anopheles gambiae
<220> FEATURE:
<221> NAME/KEY: MOD_RES
<222> LOCATION: (75)..(75)
<223> OTHER INFORMATION: Any amino acid
<220> FEATURE:
<221> NAME/KEY: MOD_RES
<222> LOCATION: (87)..(87)
<223> OTHER INFORMATION: Any amino acid

<400> SEQUENCE: 8

Lys Val His Gln Leu Trp Ile Gln Glu Gly Gly Ser Leu Glu His Glu
1               5                   10                  15

Leu Ala Tyr Thr Gln Lys Ser Leu Gly Glu Met Asp Ser Ser Thr His
            20                  25                  30

Gln Leu Leu Ile Gln Thr Pro Lys Asp Met Asp Ala Ser Ile Leu His
        35                  40                  45

Pro Asn Ala Leu Leu Thr His Leu Asp Val Val Lys Lys Ala Ile Ser
    50                  55                  60

Val Thr Val His Met Tyr Asp Ile Thr Trp Xaa Leu Lys Asp Met Cys
65                  70                  75                  80

Tyr Ser Pro Ser Ile Pro Xaa Phe Asp Thr His Phe Ile Glu Gln Ile
                85                  90                  95

Phe Glu Asn Ile Ile Pro Cys Ala Ile Ile Thr Pro Leu Asp Cys Phe
            100                 105                 110

Trp Glu Gly
        115

<210> SEQ ID NO 9
<211> LENGTH: 5187
<212> TYPE: DNA
<213> ORGANISM: Mus musculus

<400> SEQUENCE: 9
gggtctgtca cccggagccg gagtccccgg cggccagcag cgtcctcgcg agccgagcgc      60
ccaggcgcgc ccggagcccg cggcggcggg ggcaacatgg cctcggctgg taacgccgcc    120
ggggccctgg gcaggcaggc cggcggcggg aggcgcagac ggaccggggg accgcaccgc    180
```

-continued

```
gccgcgccgg accgggacta tctgcaccgg cccagctact gcgacgccgc cttcgctctg    240
gagcagattt ccaaggggaa ggctactggc cggaaagcgc cgctgtggct gagagcgaag    300
tttcagagac tcttatttaa actgggttgt tacattcaaa agaactgcgg caagttttg     360 gttgtgggtc tcctcatatt tggggccttc gctgtgggat taaaggcagc taatctcgag    420
accaacgtgg aggagctgtg ggtggaagtt ggtggacgag tgagtcgaga attaaattat    480
acccgtcaga agataggaga agaggctatg tttaatcctc aactcatgat acagactcca    540
aaagaagaag gcgctaatgt tctgaccaca gaggctctcc tgcaacacct ggactcagca    600
ctccaggcca gtcgtgtgca cgtctacatg tataacaggc aatggaagtt ggaacatttg    660
tgctacaaat caggggaact tatcacggag acaggttaca tggatcagat aatagaatac    720 cttaccctt gcttaatcat tacacccttg gactgcttct gggaagggc aaagctacag      780 tccgggacag catacctcct aggtaagcct cctttacggt ggacaaactt tgacccttg     840 gaattcctag aagagttaaa gaaaataaac taccaagtgg acagctggga ggaaatgctg    900
aataaagccg aagttggcca tgggtacatg gaccggcctt gcctcaaccc agccgaccca    960
gattgccctg ccacagcccc taacaaaaat tcaaccaaac ctcttgatgt ggcccttgtt   1020
ttgaatggtg gatgtcaagg tttatccagg aagtatatgc attggcagga ggagttgatt   1080
gtgggtggta ccgtcaagaa tgccactgga aaacttgtca cgctcacgc cctgcaaacc    1140 atgttccagt taatgactcc caagcaaatg tatgaacact caggggcta cgactatgtc    1200 tctcacatca actggaatga agacagggca gccgccatcc tggaggcctg gcagaggact   1260
tacgtggagg tggttcatca aagtgtcgcc ccaaactcca ctcaaaaggt gcttcccttc   1320
acaaccacga ccctggacga catcctaaaa tccttctctg atgtcagtgt catccgagtg   1380
gccagcggct acctactgat gcttgcctat gcctgtttaa ccatgctgcg ctgggactgc   1440
tccaagtccc agggtgccgt ggggctggct ggcgtcctgt tggttgcgct gtcagtggct   1500
gcaggattgg gcctctgctc cttgattggc atttcttta atgctgcgac aactcaggtt    1560
ttgccgtttc ttgctcttgg tgttggtgtg gatgatgtct tcctcctggc ccatgcattc   1620
agtgaaacag gacagaataa gaggattcca tttgaggaca ggactgggga gtgcctcaag   1680
cgcaccggag ccagcgtggc cctcacctcc atcagcaatg tcaccgcctt cttcatggcc   1740
gcattgatcc ctatccctgc cctgcgagcg ttctccctcc aggctgctgt ggtggtggta   1800
ttcaattttg ctatggttct gctcatttt cctgcaattc tcagcatgga tttatacaga    1860
cgtgaggaca aagattgga tattttctgc tgtttcacaa gcccctgtgt cagcagggtg    1920
attcaagttg agccacaggc ctacacagag cctcacagta acaccggta cagcccccca    1980 cccccataca ccagccacag cttcgcccac gaaacccata tcactatgca gtccaccgtt   2040
cagctccgca cagagtatga ccctcacacg cacgtgtact acaccaccgc cgagccacgc   2100
tctgagatct ctgtacagcc tgttaccgtc acccaggaca acctcagctg tcagagtccc   2160
gagagcacca gctctaccag ggacctgctc tcccagttct cagactccag cctccactgc   2220
ctcgagcccc cctgcaccaa gtggacactc tcttcgtttg cagagaagca ctatgctcct   2280
ttcctcctga acccaaagc caaggttgtg gtaatccttc ttttcctggg cttgctgggg   2340
gtcagccttt atgggaccac ccgagtgaga gacgggctgg acctcacgga cattgttccc   2400
cgggaaacca gagaatatga cttcatagct gcccagttca agtacttctc tttctacaac   2460
atgtatatag tcacccagaa agcagactac ccgaatatcc agcacctact ttacgacctt   2520
cataagagtt tcagcaatgt gaagtatgtc atgctggagg agaacaagca acttccccaa   2580
```

```
atgtggctgc actactttag agactggctt caaggacttc aggatgcatt tgacagtgac    2640
tgggaaactg ggaggatcat gccaaacaat tataaaaatg gatcagatga cggggtcctc    2700
gcttacaaac tcctggtgca gactggcagc cgagacaagc ccatcgacat tagtcagttg    2760
actaaacagc gtctggtaga cgcagatggc atcattaatc cgagcgcttt ctacatctac    2820
ctgaccgctt gggtcagcaa cgaccctgta gcttacgctg cctcccaggc caacatccgg    2880
cctcaccggc cggagtgggt ccatgacaaa gccgactaca tgccagagac caggctgaga    2940
atcccagcag cagagcccat cgagtacgct cagttcccct tctacctcaa cggcctacga    3000
gacacctcag actttgtgga agccatgaaa aaagtgagag tcatctgtaa caactatacg    3060
agcctgggac tgtccagcta ccccaatggc taccccttcc tgttctggga gcaatacatc    3120
agcctgcgcc actggctgct gctatccatc agcgtggtgc tggcctgcac gtttctagtg    3180
tgcgcagtct tcctcctgaa ccctggacg gccgggatca ttgtcatggt cctggctctg    3240
atgaccgttg agctctttgg catgatgggc ctcattggga tcaagctgag tgctgtgcct    3300
gtggtcatcc tgattgcatc tgttggcatc ggagtggagt tcaccgtcca cgtggctttg    3360
gcctttctga cagccattgg ggacaagaac cacagggcta tgctcgctct ggaacacatg    3420
tttgctcccg ttctggacgg tgctgtgtcc actctgctgg gtgtactgat gcttgcaggg    3480
tccgaatttg atttcattgt cagatacttc tttgccgtcc tggccattct caccgtcttg    3540
ggggttctca atggactggt tctgctgcct gtcctcttat ccttctttgg accgtgtcct    3600
gaggtgtctc cagccaatgg cctaaaccga ctgcccactc cttcgcctga ccgcctcca    3660 agtgtcgtcc ggtttgccgt gcctcctggt cacacgaaca atgggtctga ttcctccgac    3720
tcggagtaca gctctcagac cacggtgtct ggcatcagtg aggagctcag gcaatacgaa    3780
gcacagcagg gtgccggagg ccctgcccac caagtgattg tggaagccac agaaaaccct    3840
gtctttgccc ggtccactgt ggtccatccg gactccagac atcagcctcc cttgaccct    3900 cggcaacagc cccacctgga ctctggctcc ttgtccctg gacggcaagg ccagcagcct    3960
cgaagggatc cccctagaga aggcttgcgg ccaccccct acagaccgcg cagagacgct    4020
tttgaaattt ctactgaagg gcattctggc cctagcaata gggaccgctc agggcccgt    4080 ggggccgtt ctcacaaccc tcggaaccca acgtccaccg ccatgggcag ctctgtgccc    4140
agctactgcc agcccatcac cactgtgacg gcttctgctt cggtgactgt tgctgtgcat    4200
cccccgcctg gacctgggcg caaccccga ggggggccct gtccaggcta tgagagctac    4260
cctgagactg atcacgggt atttgaggat cctcatgtgc cttttcatgt caggtgtgag    4320
aggagggact caaaggtgga ggtcatagag ctacaggacg tggaatgtga ggagaggccg    4380 tggggagca gctccaactg agggtaatta aaatctgaag caaagaggcc aaagattgga    4440
aagccccgcc cccacctctt tccagaactg cttgaagaga actgcttgga attatgggaa    4500
ggcagttcat tgttactgta actgattgta ttattkkgtg aaatatttct ataaatattt    4560
aaraggtgta cacatgtaat atacatggaa atgctgtaca gtctatttcc tggggcctct    4620
ccactcctgc cccagagtgg ggagaccaca ggggccctt ccctgtgta cattggtctc    4680 tgtgccacaa ccaagcttaa cttagttta aaaaaaatct cccagcatat gtcgctgctg    4740
cttaaatatt gtataattta cttgtataat tctatgcaaa tattgcttat gtaataggat    4800
tatttgtaaa ggtttctgtt taaaatattt taaatttgca tatcacaacc ctgtggtagg    4860
atgaattgtt actgttaact tttgaacacg ctatgcgtgg taattgttta acgagcagac    4920
atgaagaaaa caggttaatc ccagtggctt ctctagggg agttgtatat ggttcgcatg    4980
```

-continued

```
ggtggatgtg tgtgtgcatg tgactttcca atgtactgta ttgtggtttg ttgttgttgt    5040
tgctgttgtt gttcattttg gtgttttttgg ttgctttgta tgatcttagc tctggcctag   5100
gtgggctggg aagtccagg tcttttttctg tcgtgatgct ggtggaaagg tgaccccaat    5160
catctgtcct attctctggg actattc                                        5187
```

<210> SEQ ID NO 10
<211> LENGTH: 1434
<212> TYPE: PRT
<213> ORGANISM: Mus musculus

<400> SEQUENCE: 10

```
Met Ala Ser Ala Gly Asn Ala Gly Ala Leu Gly Arg Gln Ala Gly
1               5                   10                  15

Gly Gly Arg Arg Arg Thr Gly Gly Pro His Arg Ala Ala Pro Asp
                20                  25                  30

Arg Asp Tyr Leu His Arg Pro Ser Tyr Cys Asp Ala Ala Phe Ala Leu
            35                  40                  45

Glu Gln Ile Ser Lys Gly Lys Ala Thr Gly Arg Lys Ala Pro Leu Trp
    50                  55                  60

Leu Arg Ala Lys Phe Gln Arg Leu Leu Phe Lys Leu Gly Cys Tyr Ile
65                  70                  75                  80

Gln Lys Asn Cys Gly Lys Phe Leu Val Val Gly Leu Leu Ile Phe Gly
                85                  90                  95

Ala Phe Ala Val Gly Leu Lys Ala Ala Asn Leu Glu Thr Asn Val Glu
            100                 105                 110

Glu Leu Trp Val Glu Val Gly Gly Arg Val Ser Arg Glu Leu Asn Tyr
        115                 120                 125

Thr Arg Gln Lys Ile Gly Glu Glu Ala Met Phe Asn Pro Gln Leu Met
    130                 135                 140

Ile Gln Thr Pro Lys Glu Glu Gly Ala Asn Val Leu Thr Thr Glu Ala
145                 150                 155                 160

Leu Leu Gln His Leu Asp Ser Ala Leu Gln Ala Ser Arg Val His Val
                165                 170                 175

Tyr Met Tyr Asn Arg Gln Trp Lys Leu Glu His Leu Cys Tyr Lys Ser
            180                 185                 190

Gly Glu Leu Ile Thr Glu Thr Gly Tyr Met Asp Gln Ile Ile Glu Tyr
        195                 200                 205

Leu Tyr Pro Cys Leu Ile Ile Thr Pro Leu Asp Cys Phe Trp Glu Gly
    210                 215                 220

Ala Lys Leu Gln Ser Gly Thr Ala Tyr Leu Leu Gly Lys Pro Pro Leu
225                 230                 235                 240

Arg Trp Thr Asn Phe Asp Pro Leu Glu Phe Leu Glu Glu Leu Lys Lys
                245                 250                 255

Ile Asn Tyr Gln Val Asp Ser Trp Glu Glu Met Leu Asn Lys Ala Glu
            260                 265                 270

Val Gly His Gly Tyr Met Asp Arg Pro Cys Leu Asn Pro Ala Asp Pro
        275                 280                 285

Asp Cys Pro Ala Thr Ala Pro Asn Lys Asn Ser Thr Lys Pro Leu Asp
    290                 295                 300

Val Ala Leu Val Leu Asn Gly Gly Cys Gln Gly Leu Ser Arg Lys Tyr
305                 310                 315                 320

Met His Trp Gln Glu Glu Leu Ile Val Gly Gly Thr Val Lys Asn Ala
                325                 330                 335

Thr Gly Lys Leu Val Ser Ala His Ala Leu Gln Thr Met Phe Gln Leu
```

```
                    340             345             350
Met Thr Pro Lys Gln Met Tyr Glu His Phe Arg Gly Tyr Asp Tyr Val
                355             360             365

Ser His Ile Asn Trp Asn Glu Asp Arg Ala Ala Ile Leu Glu Ala
    370             375             380

Trp Gln Arg Thr Tyr Val Glu Val Val His Gln Ser Val Ala Pro Asn
385             390             395             400

Ser Thr Gln Lys Val Leu Pro Phe Thr Thr Thr Leu Asp Asp Ile
                405             410             415

Leu Lys Ser Phe Ser Asp Val Ser Val Ile Arg Val Ala Ser Gly Tyr
                420             425             430

Leu Leu Met Leu Ala Tyr Ala Cys Leu Thr Met Leu Arg Trp Asp Cys
                435             440             445

Ser Lys Ser Gln Gly Ala Val Gly Leu Ala Gly Val Leu Leu Val Ala
                450             455             460

Leu Ser Val Ala Ala Gly Leu Gly Leu Cys Ser Leu Ile Gly Ile Ser
465             470             475             480

Phe Asn Ala Ala Thr Thr Gln Val Leu Pro Phe Leu Ala Leu Gly Val
                485             490             495

Gly Val Asp Asp Val Phe Leu Leu Ala His Ala Phe Ser Glu Thr Gly
                500             505             510

Gln Asn Lys Arg Ile Pro Phe Glu Asp Arg Thr Gly Glu Cys Leu Lys
                515             520             525

Arg Thr Gly Ala Ser Val Ala Leu Thr Ser Ile Ser Asn Val Thr Ala
                530             535             540

Phe Phe Met Ala Ala Leu Ile Pro Ile Pro Ala Leu Arg Ala Phe Ser
545             550             555             560

Leu Gln Ala Ala Val Val Val Phe Asn Phe Ala Met Val Leu Leu
                565             570             575

Ile Phe Pro Ala Ile Leu Ser Met Asp Leu Tyr Arg Arg Glu Asp Arg
                580             585             590

Arg Leu Asp Ile Phe Cys Cys Phe Thr Ser Pro Cys Val Ser Arg Val
                595             600             605

Ile Gln Val Glu Pro Gln Ala Tyr Thr Glu Pro His Ser Asn Thr Arg
                610             615             620

Tyr Ser Pro Pro Pro Tyr Thr Ser His Ser Phe Ala His Glu Thr
625             630             635             640

His Ile Thr Met Gln Ser Thr Val Gln Leu Arg Thr Glu Tyr Asp Pro
                645             650             655

His Thr His Val Tyr Tyr Thr Thr Ala Glu Pro Arg Ser Glu Ile Ser
                660             665             670

Val Gln Pro Val Thr Val Thr Gln Asp Asn Leu Ser Cys Gln Ser Pro
                675             680             685

Glu Ser Thr Ser Ser Thr Arg Asp Leu Leu Ser Gln Phe Ser Asp Ser
                690             695             700

Ser Leu His Cys Leu Glu Pro Pro Cys Thr Lys Trp Thr Leu Ser Ser
705             710             715             720

Phe Ala Glu Lys His Tyr Ala Pro Phe Leu Leu Lys Pro Lys Ala Lys
                725             730             735

Val Val Val Ile Leu Leu Phe Leu Gly Leu Leu Gly Val Ser Leu Tyr
                740             745             750

Gly Thr Thr Arg Val Arg Asp Gly Leu Asp Leu Thr Asp Ile Val Pro
                755             760             765
```

Arg Glu Thr Arg Glu Tyr Asp Phe Ile Ala Ala Gln Phe Lys Tyr Phe
770             775                 780

Ser Phe Tyr Asn Met Tyr Ile Val Thr Gln Lys Ala Asp Tyr Pro Asn
785             790                 795                 800

Ile Gln His Leu Leu Tyr Asp Leu His Lys Ser Phe Ser Asn Val Lys
            805                 810                 815

Tyr Val Met Leu Glu Glu Asn Lys Gln Leu Pro Gln Met Trp Leu His
            820                 825                 830

Tyr Phe Arg Asp Trp Leu Gln Gly Leu Gln Asp Ala Phe Asp Ser Asp
            835                 840                 845

Trp Glu Thr Gly Arg Ile Met Pro Asn Asn Tyr Lys Asn Gly Ser Asp
850                 855                 860

Asp Gly Val Leu Ala Tyr Lys Leu Leu Val Gln Thr Gly Ser Arg Asp
865             870                 875                 880

Lys Pro Ile Asp Ile Ser Gln Leu Thr Lys Gln Arg Leu Val Asp Ala
            885                 890                 895

Asp Gly Ile Ile Asn Pro Ser Ala Phe Tyr Ile Tyr Leu Thr Ala Trp
            900                 905                 910

Val Ser Asn Asp Pro Val Ala Tyr Ala Ala Ser Gln Ala Asn Ile Arg
            915                 920                 925

Pro His Arg Pro Glu Trp Val His Asp Lys Ala Asp Tyr Met Pro Glu
930                 935                 940

Thr Arg Leu Arg Ile Pro Ala Ala Glu Pro Ile Glu Tyr Ala Gln Phe
945             950                 955                 960

Pro Phe Tyr Leu Asn Gly Leu Arg Asp Thr Ser Asp Phe Val Glu Ala
            965                 970                 975

Ile Glu Lys Val Arg Val Ile Cys Asn Asn Tyr Thr Ser Leu Gly Leu
            980                 985                 990

Ser Ser Tyr Pro Asn Gly Tyr Pro Phe Leu Phe Trp Glu Gln Tyr Ile
            995                 1000                1005

Ser Leu Arg His Trp Leu Leu Leu Ser Ile Ser Val Val Leu Ala
    1010            1015                1020

Cys Thr Phe Leu Val Cys Ala Val Phe Leu Leu Asn Pro Trp Thr
    1025            1030                1035

Ala Gly Ile Ile Val Met Val Leu Ala Leu Met Thr Val Glu Leu
    1040            1045                1050

Phe Gly Met Met Gly Leu Ile Gly Ile Lys Leu Ser Ala Val Pro
    1055            1060                1065

Val Val Ile Leu Ile Ala Ser Val Gly Ile Gly Val Glu Phe Thr
    1070            1075                1080

Val His Val Ala Leu Ala Phe Leu Thr Ala Ile Gly Asp Lys Asn
    1085            1090                1095

His Arg Ala Met Leu Ala Leu Glu His Met Phe Ala Pro Val Leu
    1100            1105                1110

Asp Gly Ala Val Ser Thr Leu Leu Gly Val Leu Met Leu Ala Gly
    1115            1120                1125

Ser Glu Phe Asp Phe Ile Val Arg Tyr Phe Phe Ala Val Leu Ala
    1130            1135                1140

Ile Leu Thr Val Leu Gly Val Leu Asn Gly Leu Val Leu Leu Pro
    1145            1150                1155

Val Leu Leu Ser Phe Phe Gly Pro Cys Pro Glu Val Ser Pro Ala
    1160            1165                1170

Asn Gly Leu Asn Arg Leu Pro Thr Pro Ser Pro Glu Pro Pro Pro
    1175            1180                1185

```
Ser Val Val Arg Phe Ala Val Pro Pro Gly His Thr Asn Asn Gly
    1190            1195                1200

Ser Asp Ser Ser Asp Ser Glu Tyr Ser Ser Gln Thr Thr Val Ser
    1205            1210                1215

Gly Ile Ser Glu Glu Leu Arg Gln Tyr Glu Ala Gln Gln Gly Ala
    1220            1225                1230

Gly Gly Pro Ala His Gln Val Ile Val Glu Ala Thr Glu Asn Pro
    1235            1240                1245

Val Phe Ala Arg Ser Thr Val His Pro Asp Ser Arg His Gln
    1250            1255                1260

Pro Pro Leu Thr Pro Arg Gln Gln Pro His Leu Asp Ser Gly Ser
    1265            1270                1275

Leu Ser Pro Gly Arg Gln Gln Gln Pro Arg Arg Asp Pro Pro
    1280            1285                1290

Arg Glu Gly Leu Arg Pro Pro Tyr Arg Pro Arg Arg Asp Ala
    1295            1300                1305

Phe Glu Ile Ser Thr Glu Gly His Ser Gly Pro Ser Asn Arg Asp
    1310            1315                1320

Arg Ser Gly Pro Arg Gly Ala Arg Ser His Asn Pro Arg Asn Pro
    1325            1330                1335

Thr Ser Thr Ala Met Gly Ser Ser Val Pro Ser Tyr Cys Gln Pro
    1340            1345                1350

Ile Thr Thr Val Thr Ala Ser Ala Ser Val Thr Val Ala Val His
    1355            1360                1365

Pro Pro Pro Gly Pro Gly Arg Asn Pro Arg Gly Gly Pro Cys Pro
    1370            1375                1380

Gly Tyr Glu Ser Tyr Pro Glu Thr Asp His Gly Val Phe Glu Asp
    1385            1390                1395

Pro His Val Pro Phe His Val Arg Cys Glu Arg Arg Asp Ser Lys
    1400            1405                1410

Val Glu Val Ile Glu Leu Gln Asp Val Glu Cys Glu Glu Arg Pro
    1415            1420                1425

Trp Gly Ser Ser Ser Asn
    1430

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Ile Thr Pro Leu Asp Cys Phe Trp Glu Gly
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Ile Val Gly Gly
1               5
```

```
<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Phe Phe Trp Glu Gln Tyr
1               5

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (25)..(25)
<223> OTHER INFORMATION: a, c, t, g, unknown or other

<400> SEQUENCE: 14
ggacgaattc aargtncayc arytntgg                                        28

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: a, c, t, g, unknown or other

<400> SEQUENCE: 15
ggacgaattc cytcccaraa rcantc                                          26

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 16
ggacgaattc ytngantgyt tytggga                                         27

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
```

```
        primer
<220> FEATURE:
<221> NAME/KEY: modified_base
<222> LOCATION: (20)..(20)
<223> OTHER INFORMATION: inosine

<400> SEQUENCE: 17
cataccagcc aagcttgtcn ggccartgca t                              31

<210> SEQ ID NO 18
<211> LENGTH: 5288
<212> TYPE: DNA
<213> ORGANISM: Homo sapiens

<400> SEQUENCE: 18
gaattccggg gaccgcaagg agtgccgcgg aagcgcccga aggacaggct cgctcggcgc    60
gccggctctc gctcttccgc gaactggatg tgggcagcgg cggccgcaga gacctcggga   120
cccccgcgca atgtggcaat ggaaggcgca gggtctgact ccccggcagc ggccgcggcc   180
gcagcggcag cagcgcccgc cgtgtgagca gcagcagcgg ctggtctgtc aaccggagcc   240
cgagcccgag cagcctgcgg ccagcagcgt cctcgcaagc cgagcgccca ggcgcgccag   300
gagcccgcag cagcggcagc agcgcgccgg ccgcccggg aagcctccgt ccccgcggcg   360
gcggcggcgg cggcggcggc aacatggcct cggctggtaa cgccgccgag ccccaggacc   420
gcggcggcgg cggcagcggc tgtatcggtg ccccgggacg gccggctgga ggcgggaggc   480
gcagacggac gggggggctg cgccgtgctg ccgcgccgga ccgggactat ctgcaccggc   540
ccagctactg cgacgccgcc ttcgctctgg agcagatttc caaggggaag gctactggcc   600
ggaaagcgcc actgtggctg agagcgaagt ttcagagact cttatttaaa ctgggttgtt   660
acattcaaaa aaactgcggc aagttcttgg ttgtgggcct cctcatattt ggggccttcg   720
cggtgggatt aaaagcagcg aacctcgaga ccaacgtgga ggagctgtgg gtggaagttg   780
gaggacgagt aagtcgtgaa ttaaattata ctcgccagaa gattggagaa gaggctatgt   840
ttaatcctca actcatgata cagaccccta agaagaaagg tgctaatgtc ctgaccacag   900
aagcgctcct acaacacctg gactcggcac tccaggccag ccgtgtccat gtatacatgt   960
acaacaggca gtggaaattg aacatttgt gttacaaatc aggagagctt atcacagaaa  1020
caggttacat ggatcagata atagaatatc tttacccttg tttgattatt acacctttgg  1080
actgcttctg ggaaggggcg aaattacagt ctgggacagc atacctccta ggtaaacctc  1140 cttttgcggtg gacaaacttc gacccttttgg aattcctgga agagttaaag aaaataaact  1200
atcaagtgga cagctgggag gaaatgctga ataaggctga ggttggtcat ggttacatgg  1260
accgcccctg cctcaatccg gccgatccag actgccccgc cacagccccc aacaaaaatt  1320
caaccaaacc tcttgatatg gcccttgttt tgaatggtgg atgtcatggc ttatccagaa  1380
agtatatgca ctggcaggag gagttgattg tgggtggcac agtcaagaac agcactggaa  1440
aactcgtcag cgcccatgcc ctgcagacca tgttccagtt aatgactccc aagcaaatgt  1500
acgagcactt caaggggtac gagtatgtct cacacatcaa ctggaacgag acaaagcgg   1560 cagccatcct ggaggcctgg cagaggacat atgtggaggt ggttcatcag agtgtcgcac  1620
agaactccac tcaaaaggtg ctttccttca ccaccgacac cctggacgac atcctgaaat  1680
ccttctctga cgtcagtgtc atccgcgtgg ccagcggcta cttactcatg ctcgcctatg  1740
cctgtctaac catgctgcgc tgggactgct ccaagtccca gggtgccgtg gggctggctg  1800
gcgtcctgct ggttgcactg tcagtggctg caggactggg cctgtgctca ttgatcggaa  1860
```

```
tttcctttaa cgctgcaaca actcaggttt tgccatttct cgctcttggt gttggtgtgg   1920
atgatgtttt tcttctggcc cacgccttca gtgaaacagg acagaataaa agaatccctt   1980
ttgaggacag gaccggggag tgcctgaagc gcacaggagc cagcgtggcc ctcacgtcca   2040
tcagcaatgt cacagccttc ttcatggccg cgttaatccc aattcccgct ctgcgggcgt   2100
tctccctcca ggcagcggta gtagtggtgt tcaattttgc catggttctg ctcattttc   2160 ctgcaattct cagcatggat ttatatcgac gcgaggacag gagactggat attttctgct   2220
gttttacaag cccctgcgtc agcagagtga ttcaggttga acctcaggcc tacaccgaca   2280
cacacgacaa tacccgctac agccccccac ctccctacag cagccacagc tttgcccatg   2340
aaacgcagat taccatgcag tccactgtcc agctccgcac ggagtacgac ccccacacgc   2400
acgtgtacta caccaccgct gagccgcgct ccgagatctc tgtgcagccc gtcaccgtga   2460
cacaggacac cctcagctgc cagagcccag agagcaccag ctccacaagg gacctgctct   2520
cccagttctc cgactccagc ctccactgcc tcgagccccc ctgtacgaag tggacactct   2580
catcttttgc tgagaagcac tatgctcctt tcctcttgaa accaaaagcc aaggtagtgg   2640
tgatcttcct ttttctgggc ttgctggggg tcagcctta tggcaccacc cgagtgagag   2700
acgggctgga ccttacggac attgtacctc gggaaaccag agaatatgac tttattgctg   2760
cacaattcaa atactttct ttctacaaca tgtatatagt cacccagaaa gcagactacc   2820
cgaatatcca gcacttactt tacgacctac acaggagttt cagtaacgtg aagtatgtca   2880
tgttggaaga aaacaaacag cttcccaaaa tgtggctgca ctacttcaga gactggcttc   2940
agggacttca ggatgcattt gacagtgact gggaaaccgg gaaaatcatg ccaaacaatt   3000
acaagaatgg atcagacgat ggagtccttg cctacaaact cctggtgcaa accggcagcc   3060
gcgataagcc catcgacatc agccagttga ctaaacagcg tctggtggat gcagatggca   3120
tcattaatcc cagcgctttc tacatctacc tgacggcttg ggtcagcaac gaccccgtcg   3180
cgtatgctgc ctcccaggcc aacatccggc acaccgacc agaatgggtc cacgacaaag   3240
ccgactacat gcctgaaaca aggctgagaa tcccggcagc agagcccatc gagtatgccc   3300
agttcccttt ctacctcaac gggttgcggg acacctcaga ctttgtggag gcaattgaaa   3360
aagtaaggac catctgcagc aactatacga gcctggggct gtccagttac cccaacggct   3420 acccttcct cttctgggag cagtacatcg gcctccgcca ctggctgctg ctgttcatca   3480
gcgtggtgtt ggcctgcaca ttcctcgtgt gcgctgtctt ccttctgaac ccctggacgg   3540
ccgggatcat tgtgatggtc ctggcgctga tgacggtcga gctgttcggc atgatgggcc   3600
tcatcggaat caagctcagt gccgtgcccg tggtcatcct gatcgcttct gttggcatag   3660
gagtggagtt caccgttcac gttgctttgg cctttctgac ggccatcggc gacaagaacc   3720
gcagggctgt gcttgccctg agcacatgt ttgcacccgt cctggatggc gccgtgtcca   3780
ctctgctggg agtgctgatg ctggcgggat ctgagttcga cttcattgtc aggtatttct   3840
ttgctgtgct ggcgatcctc accatcctcg gcgttctcaa tgggctggtt ttgcttcccg   3900
tgcttttgtc tttctttgga ccatatcctg aggtgtctcc agccaacggc ttgaaccgcc   3960
tgcccacacc ctcccctgag ccaccccca gcgtggtccg cttcgccatg ccgccggcc   4020 acacgcacag cgggtctgat tcctccgact cggagtatag ttcccagacg acagtgtcag   4080
gcctcagcga ggagcttcgg cactacgagg cccagcaggg cgcgggaggc cctgcccacc   4140
aagtgatcgt ggaagccaca gaaaacccg tcttcgccca ctccactgtg gtccatcccg   4200
aatccaggca tcacccaccc tcgaacccga gacagcagcc ccacctggac tcagggtccc   4260
```

```
tgcctcccgg acggcaaggc cagcagcccc gcagggaccc cccagagaaa ggcttgtggc    4320 caccccctcta cagaccgcgc agagacgctt ttgaaatttc tactgaaggg cattctggcc    4380
ctagcaatag ggcccgctgg ggccctcgcg gggcccgttc tcacaaccct cggaacccag    4440
cgtccactgc catgggcagc tccgtgcccg gctactgcca gcccatcacc actgtgacgg    4500
cttctgcctc cgtgactgtc gccgtgcacc cgccgcctgt ccctgggcct gggcggaacc    4560
cccgaggggg actctgccca ggctaccctg agactgacca cggcctgttt gaggaccccc    4620
acgtgccttt ccacgtccgg tgtgagagga gggattcgaa ggtggaagtc attgagctgc    4680
aggacgtgga atgcgaggag aggccccggg gaagcagctc caactgaggg tgattaaaat    4740
ctgaagcaaa gaggccaaag attggaaacc cccaccccc acctctttcc agaactgctt    4800
gaagagaact ggttggagtt atggaaaaga tgccctgtgc caggacagca gttcattgtt    4860
actgtaaccg attgtattat tttgttaaat atttctataa atatttaaga gatgtacaca    4920
tgtgtaatat aggaaggaag gatgtaaagt ggtatgatct ggggcttctc cactcctgcc    4980
ccagagtgtg gaggccacag tggggcctct ccgtatttgt gcatgggct ccgtgccaca    5040 accaagcttc attagtctta aatttcagca tatgttgctg ctgcttaaat attgtataat    5100
ttacttgtat aattctatgc aaatattgct tatgtaatag gattattttg taaaggtttc    5160
tgtttaaaat attttaaatt tgcatatcac aaccctgtgg tagtatgaaa tgttactgtt    5220
aactttcaaa cacgctatgc gtgataattt ttttgtttaa tgagcagata tgaagaaagc    5280
ccggaatt                                                              5288

<210> SEQ ID NO 19
<211> LENGTH: 1447
<212> TYPE: PRT
<213> ORGANISM: Homo sapiens

<400> SEQUENCE: 19

Met Ala Ser Ala Gly Asn Ala Ala Glu Pro Gln Asp Arg Gly Gly Gly
1               5                   10                  15

Gly Ser Gly Cys Ile Gly Ala Pro Gly Arg Pro Ala Gly Gly Gly Arg
            20                  25                  30

Arg Arg Arg Thr Gly Gly Leu Arg Ala Ala Ala Pro Asp Arg Asp
        35                  40                  45

Tyr Leu His Arg Pro Ser Tyr Cys Asp Ala Ala Phe Ala Leu Glu Gln
    50                  55                  60

Ile Ser Lys Gly Lys Ala Thr Gly Arg Lys Ala Pro Leu Trp Leu Arg
65                  70                  75                  80

Ala Lys Phe Gln Arg Leu Leu Phe Lys Leu Gly Cys Tyr Ile Gln Lys
                85                  90                  95

Asn Cys Gly Lys Phe Leu Val Val Gly Leu Leu Ile Phe Gly Ala Phe
            100                 105                 110

Ala Val Gly Leu Lys Ala Ala Asn Leu Glu Thr Asn Val Glu Glu Leu
        115                 120                 125

Trp Val Glu Val Gly Gly Arg Val Ser Arg Glu Leu Asn Tyr Thr Arg
    130                 135                 140

Gln Lys Ile Gly Glu Glu Ala Met Phe Asn Pro Gln Leu Met Ile Gln
145                 150                 155                 160

Thr Pro Lys Glu Glu Gly Ala Asn Val Leu Thr Thr Glu Ala Leu Leu
                165                 170                 175

Gln His Leu Asp Ser Ala Leu Gln Ala Ser Arg Val His Val Tyr Met
            180                 185                 190
```

```
Tyr Asn Arg Gln Trp Lys Leu Glu His Leu Cys Tyr Lys Ser Gly Glu
            195                 200                 205

Leu Ile Thr Glu Thr Gly Tyr Met Asp Gln Ile Ile Glu Tyr Leu Tyr
        210                 215                 220

Pro Cys Leu Ile Ile Thr Pro Leu Asp Cys Phe Trp Glu Gly Ala Lys
225                 230                 235                 240

Leu Gln Ser Gly Thr Ala Tyr Leu Leu Gly Lys Pro Pro Leu Arg Trp
                245                 250                 255

Thr Asn Phe Asp Pro Leu Glu Phe Leu Glu Glu Leu Lys Lys Ile Asn
            260                 265                 270

Tyr Gln Val Asp Ser Trp Glu Glu Met Leu Asn Lys Ala Glu Val Gly
        275                 280                 285

His Gly Tyr Met Asp Arg Pro Cys Leu Asn Pro Ala Asp Pro Asp Cys
    290                 295                 300

Pro Ala Thr Ala Pro Asn Lys Asn Ser Thr Lys Pro Leu Asp Met Ala
305                 310                 315                 320

Leu Val Leu Asn Gly Gly Cys His Gly Leu Ser Arg Lys Tyr Met His
                325                 330                 335

Trp Gln Glu Glu Leu Ile Val Gly Gly Thr Val Lys Asn Ser Thr Gly
            340                 345                 350

Lys Leu Val Ser Ala His Ala Leu Gln Thr Met Phe Gln Leu Met Thr
        355                 360                 365

Pro Lys Gln Met Tyr Glu His Phe Lys Gly Tyr Glu Tyr Val Ser His
    370                 375                 380

Ile Asn Trp Asn Glu Asp Lys Ala Ala Ile Leu Glu Ala Trp Gln
385                 390                 395                 400

Arg Thr Tyr Val Glu Val Val His Gln Ser Val Ala Gln Asn Ser Thr
                405                 410                 415

Gln Lys Val Leu Ser Phe Thr Thr Thr Leu Asp Asp Ile Leu Lys
            420                 425                 430

Ser Phe Ser Asp Val Ser Val Ile Arg Val Ala Ser Gly Tyr Leu Leu
        435                 440                 445

Met Leu Ala Tyr Ala Cys Leu Thr Met Leu Arg Trp Asp Cys Ser Lys
    450                 455                 460

Ser Gln Gly Ala Val Gly Leu Ala Gly Val Leu Leu Val Ala Leu Ser
465                 470                 475                 480

Val Ala Ala Gly Leu Gly Leu Cys Ser Leu Ile Gly Ile Ser Phe Asn
                485                 490                 495

Ala Ala Thr Thr Gln Val Leu Pro Phe Leu Ala Leu Gly Val Gly Val
            500                 505                 510

Asp Asp Val Phe Leu Leu Ala His Ala Phe Ser Glu Thr Gly Gln Asn
        515                 520                 525

Lys Arg Ile Pro Phe Glu Asp Arg Thr Gly Glu Cys Leu Lys Arg Thr
    530                 535                 540

Gly Ala Ser Val Ala Leu Thr Ser Ile Ser Asn Val Thr Ala Phe Phe
545                 550                 555                 560

Met Ala Ala Leu Ile Pro Ile Pro Ala Leu Arg Ala Phe Ser Leu Gln
                565                 570                 575

Ala Ala Val Val Val Phe Asn Phe Ala Met Val Leu Leu Ile Phe
            580                 585                 590

Pro Ala Ile Leu Ser Met Asp Leu Tyr Arg Arg Glu Asp Arg Leu
        595                 600                 605

Asp Ile Phe Cys Cys Phe Thr Ser Pro Cys Val Ser Arg Val Ile Gln
    610                 615                 620
```

```
Val Glu Pro Gln Ala Tyr Thr Asp Thr His Asp Asn Thr Arg Tyr Ser
625                 630                 635                 640

Pro Pro Pro Pro Tyr Ser Ser His Ser Phe Ala His Glu Thr Gln Ile
                645                 650                 655

Thr Met Gln Ser Thr Val Gln Leu Arg Thr Glu Tyr Asp Pro His Thr
            660                 665                 670

His Val Tyr Tyr Thr Thr Ala Glu Pro Arg Ser Glu Ile Ser Val Gln
            675                 680                 685

Pro Val Thr Val Thr Gln Asp Thr Leu Ser Cys Gln Ser Pro Glu Ser
        690                 695                 700

Thr Ser Ser Thr Arg Asp Leu Leu Ser Gln Phe Ser Asp Ser Ser Leu
705                 710                 715                 720

His Cys Leu Glu Pro Pro Cys Thr Lys Trp Thr Leu Ser Ser Phe Ala
                725                 730                 735

Glu Lys His Tyr Ala Pro Phe Leu Leu Lys Pro Lys Ala Lys Val Val
            740                 745                 750

Val Ile Phe Leu Phe Leu Gly Leu Gly Val Ser Leu Tyr Gly Thr
            755                 760                 765

Thr Arg Val Arg Asp Gly Leu Asp Leu Thr Asp Ile Val Pro Arg Glu
770                 775                 780

Thr Arg Glu Tyr Asp Phe Ile Ala Ala Gln Phe Lys Tyr Phe Ser Phe
785                 790                 795                 800

Tyr Asn Met Tyr Ile Val Thr Gln Lys Ala Asp Tyr Pro Asn Ile Gln
                805                 810                 815

His Leu Leu Tyr Asp Leu His Arg Ser Phe Ser Asn Val Lys Tyr Val
                820                 825                 830

Met Leu Glu Glu Asn Lys Gln Leu Pro Lys Met Trp Leu His Tyr Phe
                835                 840                 845

Arg Asp Trp Leu Gln Gly Leu Gln Asp Ala Phe Asp Ser Asp Trp Glu
850                 855                 860

Thr Gly Lys Ile Met Pro Asn Asn Tyr Lys Asn Gly Ser Asp Asp Gly
865                 870                 875                 880

Val Leu Ala Tyr Lys Leu Leu Val Gln Thr Gly Ser Arg Asp Lys Pro
                885                 890                 895

Ile Asp Ile Ser Gln Leu Thr Lys Gln Arg Leu Val Asp Ala Asp Gly
                900                 905                 910

Ile Ile Asn Pro Ser Ala Phe Tyr Ile Tyr Leu Thr Ala Trp Val Ser
                915                 920                 925

Asn Asp Pro Val Ala Tyr Ala Ala Ser Gln Ala Asn Ile Arg Pro His
930                 935                 940

Arg Pro Glu Trp Val His Asp Lys Ala Asp Tyr Met Pro Glu Thr Arg
945                 950                 955                 960

Leu Arg Ile Pro Ala Ala Glu Pro Ile Glu Tyr Ala Gln Phe Pro Phe
                965                 970                 975

Tyr Leu Asn Gly Leu Arg Asp Thr Ser Asp Phe Val Glu Ala Ile Glu
            980                 985                 990

Lys Val Arg Thr Ile Cys Ser Asn Tyr Thr Ser Leu Gly Leu Ser Ser
            995                 1000                1005

Tyr Pro Asn Gly Tyr Pro Leu Phe Trp Glu Gln Tyr Ile Gly
    1010                1015                1020

Leu Arg His Trp Leu Leu Leu Phe Ile Ser Val Val Leu Ala Cys
    1025                1030                1035

Thr Phe Leu Val Cys Ala Val Phe Leu Leu Asn Pro Trp Thr Ala
```

```
            1040                1045                1050

Gly  Ile  Ile  Val  Met  Val  Leu  Ala  Leu  Met  Thr  Val  Glu  Leu  Phe
     1055                1060                1065

Gly  Met  Met  Gly  Leu  Ile  Gly  Ile  Lys  Leu  Ser  Ala  Val  Pro  Val
     1070                1075                1080

Val  Ile  Leu  Ile  Ala  Ser  Val  Gly  Ile  Gly  Val  Glu  Phe  Thr  Val
     1085                1090                1095

His  Val  Ala  Leu  Ala  Phe  Leu  Thr  Ala  Ile  Gly  Asp  Lys  Asn  Arg
     1100                1105                1110

Arg  Ala  Val  Leu  Ala  Leu  Glu  His  Met  Phe  Ala  Pro  Val  Leu  Asp
     1115                1120                1125

Gly  Ala  Val  Ser  Thr  Leu  Leu  Gly  Val  Leu  Met  Leu  Ala  Gly  Ser
     1130                1135                1140

Glu  Phe  Asp  Phe  Ile  Val  Arg  Tyr  Phe  Phe  Ala  Val  Leu  Ala  Ile
     1145                1150                1155

Leu  Thr  Ile  Leu  Gly  Val  Leu  Asn  Gly  Leu  Val  Leu  Leu  Pro  Val
     1160                1165                1170

Leu  Leu  Ser  Phe  Phe  Gly  Pro  Tyr  Pro  Glu  Val  Ser  Pro  Ala  Asn
     1175                1180                1185

Gly  Leu  Asn  Arg  Leu  Pro  Thr  Pro  Ser  Pro  Glu  Pro  Pro  Pro  Ser
     1190                1195                1200

Val  Val  Arg  Phe  Ala  Met  Pro  Pro  Gly  His  Thr  His  Ser  Gly  Ser
     1205                1210                1215

Asp  Ser  Ser  Asp  Ser  Glu  Tyr  Ser  Ser  Gln  Thr  Thr  Val  Ser  Gly
     1220                1225                1230

Leu  Ser  Glu  Glu  Leu  Arg  His  Tyr  Glu  Ala  Gln  Gln  Gly  Ala  Gly
     1235                1240                1245

Gly  Pro  Ala  His  Gln  Val  Ile  Val  Glu  Ala  Thr  Glu  Asn  Pro  Val
     1250                1255                1260

Phe  Ala  His  Ser  Thr  Val  Val  His  Pro  Glu  Ser  Arg  His  His  Pro
     1265                1270                1275

Pro  Ser  Asn  Pro  Arg  Gln  Gln  Pro  His  Leu  Asp  Ser  Gly  Ser  Leu
     1280                1285                1290

Pro  Pro  Gly  Arg  Gln  Gly  Gln  Pro  Arg  Arg  Asp  Pro  Pro  Arg
     1295                1300                1305

Glu  Gly  Leu  Trp  Pro  Pro  Leu  Tyr  Arg  Pro  Arg  Arg  Asp  Ala  Phe
     1310                1315                1320

Glu  Ile  Ser  Thr  Glu  Gly  His  Ser  Gly  Pro  Ser  Asn  Arg  Ala  Arg
     1325                1330                1335

Trp  Gly  Pro  Arg  Gly  Ala  Arg  Ser  His  Asn  Pro  Arg  Asn  Pro  Ala
     1340                1345                1350

Ser  Thr  Ala  Met  Gly  Ser  Ser  Val  Pro  Gly  Tyr  Cys  Gln  Pro  Ile
     1355                1360                1365

Thr  Thr  Val  Thr  Ala  Ser  Ala  Ser  Val  Thr  Val  Ala  Val  His  Pro
     1370                1375                1380

Pro  Pro  Val  Pro  Gly  Pro  Gly  Arg  Asn  Pro  Arg  Gly  Gly  Leu  Cys
     1385                1390                1395

Pro  Gly  Tyr  Pro  Glu  Thr  Asp  His  Gly  Leu  Phe  Glu  Asp  Pro  His
     1400                1405                1410

Val  Pro  Phe  His  Val  Arg  Cys  Glu  Arg  Arg  Asp  Ser  Lys  Val  Glu
     1415                1420                1425

Val  Ile  Glu  Leu  Gln  Asp  Val  Glu  Cys  Glu  Glu  Arg  Pro  Arg  Gly
     1430                1435                1440
```

Ser Ser  Ser Asn
    1445

<210> SEQ ID NO 20
<211> LENGTH: 11
<212> TYPE: DNA
<213> ORGANISM: Homo sapiens

<400> SEQUENCE: 20
atatccagca c                                                        11

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctgagcagat ttcccaggtc                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cctcagacag acctttcctc                                               20

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gagtttgcag tgatgttgct attc                                          24

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
accgccttac ctgctgctc                                                19

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgcactaatt ttcttattac agtgag                                        26

<210> SEQ ID NO 26

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
taaggcacac tactggggtg                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaacacccca gtagtgtgcc                                                 20

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgagtcctag agaagtcaca gacatc                                          26

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggctcttttc atggtctcgt c                                               21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgttttgctc tccacccttc                                                 20

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcactggatt ttaacaaggc atg                                             23

<210> SEQ ID NO 32
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 32
agggcataga ttgtcctcgg                                                20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tgggaatact gatgatgtgc c                                              21

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cataaccagc gagtctgcac                                                20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
catttgggca tttcgcattc                                                20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
accaaaccaa actccagccc                                                20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgcccccatt gttctgcttg                                                20

<210> SEQ ID NO 38
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 38
ggacagcaga taaatggctc c                                              21

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcatctcgca tgtctaatgc cac                                            23

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aagctgtgat gtccccaaag                                                20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gaccatgtcc agtgcagctc                                                20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgttcaggat caccacagcc                                                20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agtcctctga ttgggcggag                                                20

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 44
ccattctgca cccaatcaaa ag                                              22

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aaaatggcag aatgaaagca cc                                              22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ctgatgaact ccaaaggttc tg                                              22

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggaagagtca gtggtgctcc                                                 20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cgccaaagac cgaaaggac                                                  19

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agggtccttc tggctgcgag                                                 20

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gctgtcaagc agcctccac                   19

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gctctcaagg cagaagtgtg                   20

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggaaggcacc tctgtaagtt c                 21

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gctcctaacc tgtgcccttc                   20

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gaatttgact tccacaaagc cc                22

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cgcccactga ccactgtgtg                   20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gagccagagg aaatgggttg                   20

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
agcatttacc aggtgaagtc c                                              21

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ttgcacacgc ctgcttac                                                  18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgttcccgtt tcctcttg                                                  18

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcacaggaaa cacagcattc                                                20

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcaggtaaat ggacaagaac ac                                             22

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
actaccacgg tgggaagacc                                                20

```
<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cccttctaac ccaccctcac                                                    20

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gacacatcag ccttgctc                                                      18
```